United States Patent
Stanton et al.

(10) Patent No.: US 11,413,348 B2
(45) Date of Patent: *Aug. 16, 2022

(54) LOW MOLECULAR WEIGHT CATIONIC LIPIDS FOR OLIGONUCLEOTIDE DELIVERY

(71) Applicant: SIRNA THERAPEUTICS, INC., Cambridge, MA (US)

(72) Inventors: Matthew G. Stanton, Marlton, NJ (US); Brian W. Budzik, Perkiomenville, PA (US); Gregory L. Beutner, Green Brook, NJ (US); Hongbiao Liao, Bridgewater, NJ (US)

(73) Assignee: SIRNA THEREPEUTICS, INC., Cambridge, MA (US)

( * ) Notice: Subject to any disclaimer, the term of this patent is extended or adjusted under 35 U.S.C. 154(b) by 4 days.

This patent is subject to a terminal disclaimer.

(21) Appl. No.: 16/741,100

(22) Filed: Jan. 13, 2020

(65) Prior Publication Data

US 2020/0222540 A1 Jul. 16, 2020

Related U.S. Application Data

(63) Continuation of application No. 15/591,818, filed on May 10, 2017, now Pat. No. 10,576,155, which is a continuation of application No. 13/823,830, filed as application No. PCT/US2011/052328 on Sep. 20, 2011, now Pat. No. 9,669,097.

(60) Provisional application No. 61/514,270, filed on Aug. 2, 2011, provisional application No. 61/384,486, filed on Sep. 20, 2010.

(51) Int. Cl.
| | |
|---|---|
| *A61K 47/18* | (2017.01) |
| *C07C 211/08* | (2006.01) |
| *C07C 211/04* | (2006.01) |
| *C07C 211/17* | (2006.01) |
| *C07C 211/21* | (2006.01) |
| *C12N 15/88* | (2006.01) |
| *C07D 207/06* | (2006.01) |
| *A61K 48/00* | (2006.01) |
| *A61K 45/00* | (2006.01) |

(52) U.S. Cl.
CPC ............ *A61K 47/18* (2013.01); *C07C 211/04* (2013.01); *C07C 211/08* (2013.01); *C07C 211/17* (2013.01); *C07C 211/21* (2013.01); *C07D 207/06* (2013.01); *C12N 15/88* (2013.01); *A61K 45/00* (2013.01); *A61K 48/00* (2013.01)

(58) Field of Classification Search
CPC ........ B65H 2402/412; B65H 2701/376; B65H 75/364; G02B 6/4463; H02G 1/083; H02G 1/085; A61K 45/00; A61K 47/18; A61K 48/00; A61P 43/00; C07C 211/04; C07C 211/08; C07C 211/17; C07C 211/21; C07D 207/06; C12N 15/88
See application file for complete search history.

(56) References Cited

U.S. PATENT DOCUMENTS

| | | | |
|---|---|---|---|
| 3,532,762 A * | 10/1970 | Teisseire | ............... C07C 11/21 585/251 |
| 4,431,836 A | 2/1984 | Arena | |
| 8,518,907 B2 | 8/2013 | Brown et al. | |
| 8,835,623 B2 | 9/2014 | Brown et al. | |
| 9,029,341 B2 | 5/2015 | Bartz et al. | |
| 9,233,997 B2 | 1/2016 | Ason | |
| 9,447,420 B2 | 9/2016 | Brown | |
| 9,494,290 B2 | 10/2016 | Bartz | |
| 9,669,097 B2 | 6/2017 | Stanton | |
| 9,850,491 B2 | 12/2017 | Brown | |
| 9,879,262 B2 | 1/2018 | Bartz | |
| 10,576,155 B2 * | 3/2020 | Stanton | ................ C12N 15/88 |
| 2006/0083780 A1 | 4/2006 | Heyes et al. | |
| 2006/0240554 A1 | 10/2006 | Chen et al. | |
| 2008/0020058 A1 | 1/2008 | Chen et al. | |
| 2009/0263407 A1 | 10/2009 | Dande et al. | |
| 2009/0285881 A1 | 11/2009 | Dande et al. | |
| 2010/0055168 A1 | 3/2010 | Dande et al. | |
| 2010/0055169 A1 | 3/2010 | Dande et al. | |
| 2010/0063131 A1 | 3/2010 | Takeuchi et al. | |
| 2010/0063135 A1 | 3/2010 | Dande et al. | |
| 2010/0076055 A1 | 3/2010 | Dande et al. | |

(Continued)

FOREIGN PATENT DOCUMENTS

| | | |
|---|---|---|
| WO | 2001/44160 A2 | 6/2001 |
| WO | 2009/086558 A1 | 7/2009 |

(Continued)

OTHER PUBLICATIONS

Kitatsuji et al. (1971, Yakugaku Zasshi, 91(7), pp. 713-720). (Year: 1971).*

(Continued)

*Primary Examiner* — Kara R McMillian
(74) *Attorney, Agent, or Firm* — Nixon Peabody LLP; David S. Resnick; Ravinderjit Braich

(57) ABSTRACT

The instant invention provides for novel cationic lipids that can be used in combination with other lipid components such as cholesterol and PEG-lipids to form lipid nanoparticles with oligonucleotides. It is an object of the instant invention to provide a cationic lipid scaffold that demonstrates enhanced efficacy along with lower liver toxicity as a result of lower lipid levels in the liver. The present invention employs low molecular weight cationic lipids with one short lipid chain to enhance the efficiency and tolerability of in vivo delivery of siRNA.

25 Claims, 7 Drawing Sheets

Specification includes a Sequence Listing.

(56) References Cited

U.S. PATENT DOCUMENTS

| | | |
|---|---|---|
| 2010/0099738 A1 | 4/2010 | Hansen et al. |
| 2010/0104629 A1 | 4/2010 | Dande et al. |
| 2010/0215582 A1 | 8/2010 | Isoda et al. |
| 2013/0165500 A1 | 6/2013 | Ason et al. |
| 2014/0343126 A1 | 11/2014 | Brown et al. |
| 2018/0030454 A1 | 2/2018 | Brown |
| 2018/0100154 A1 | 4/2018 | Ason |
| 2018/0195071 A1 | 7/2018 | Bartz |

FOREIGN PATENT DOCUMENTS

| | | |
|---|---|---|
| WO | 2009/127060 A1 | 10/2009 |
| WO | 2009/132131 A1 | 10/2009 |
| WO | 2010/042877 A1 | 4/2010 |
| WO | 2010/054384 A1 | 5/2010 |
| WO | 2010/054401 A1 | 5/2010 |
| WO | 2010/054405 A1 | 5/2010 |
| WO | 2010/054406 A1 | 5/2010 |
| WO | 2012/018754 A2 | 2/2012 |
| WO | 2012/024170 A2 | 2/2012 |
| WO | 2012/027467 A1 | 3/2012 |

OTHER PUBLICATIONS

Germon et al. (Bulletin de la Societe Chimique de France (1984), (9-10, Pt. 2), 377-89). (Year: 1984).*

Cocker et al. (Journal of the Chemical Society, Perkin Transactions 1: Organic and Bio-Organic Chemistry (1972-1999) (1984), (10) , 2241-3) (Year: 1984).*

Hasiak (Bulletin de la Societe Chimique de France (1974), (9-10, Pt. 2), pp. 2015-2022) (Year: 1974).*

Tagmazyan et al. (Zhurnal Organicheskoi Khimii (1974), 10(4), 740-5). (Year: 1974).*

Glacet et al. (Comptes Rendus des Seances de l'Academie des Sciences, Serie C: Sciences Chimiques (1967), 264(24), pp. 1988-1991). (Year: 1967).*

Brown et al., "Mass Spectrometry in Structural and Stereochemical Problems—CLXXI: Factors Governing the Preferential Loss of Small vs. Large Radicals in The α-FISSION Of Aliphatic Amines", Organic Mass Spectrometry 2:625-630 (1969).

Hammermum et al., "Competing Simple Cleavage Reactions: The Elimination of Alkyl Radicals from Amine Radical Cations", Journal of the American Chemical Society 127:6466-6475 (2005).

Kitatsuji et al., "Studies on the Components in NTU Shale Oil. IV. The Hofmann Degradation of Open-Chain Quaternary Ammonium Compounds", Yakugaku Zasshi: Journal of the Pharmaceutical Society of Japan 91 (7):732-739 (1971).

Semple et al., "Rational design of cationic lipids for siRNA delivery", Nature Biotechnology 28(2):172-176 (2010).

* cited by examiner

LOW MOLECULAR WEIGHT CATIONIC LIPIDS FOR OLIGONUCLEOTIDE DELIVERY

CROSS REFERENCE TO RELATED APPLICATIONS

This application is a Continuation Application of U.S. Ser. No. 15/591,818 filed May 10, 2017, which is a Continuation Application of U.S. Ser. No. 13/823,830 filed Mar. 15, 2013, now U.S. Pat. No. 9,669,097 issued on Jun. 6, 2017, which is a 371 National Phase Entry of International Patent Application No. PCT/US2011/052328 filed on Sep. 20, 2011, which claims benefit under 35 U.S.C. § 119(e) of U.S. Provisional Patent Application Ser. No. 61/514,270 filed on Aug. 2, 2011 and U.S. Provisional patent application Ser. No. 61/384,486 filed on Sep. 20, 2010, the contents of all of which are incorporated herein by reference in their entireties.

REFERENCE TO SEQUENCE LISTING SUBMITTED ELECTRONICALLY

The sequence listing of the present application is being submitted electronically via EFS-Web as an ASCII formatted sequence listing with a file name "051058-081221-SEQ.txt", creation date of May 10, 2017 and a size of 11,561 bytes. This sequence listing submitted via EFS-Web is part of the specification and is herein incorporated by reference in its entirety.

BACKGROUND OF THE INVENTION

The present invention relates to novel cationic lipids that can be used in combination with other lipid components such as cholesterol and PEG-lipids to form lipid nanoparticles with oligonucleotides, to facilitate the cellular uptake and endosomal escape, and to knockdown target mRNA both in vitro and in vivo.

Cationic lipids and the use of cationic lipids in lipid nanoparticles for the delivery of oligonucleotides, in particular siRNA and mRNA, have been previously disclosed. Lipid nanoparticles and use of lipid nanoparticles for the delivery of oligonucleotides, in particular siRNA and miRNA, has been previously disclosed. Oligonucleotides (including siRNA and miRNA) and the synthesis of oligonucleotides has been previously disclosed. (See US patent applications: US 2006/0083780, US 2006/0240554, US 2008/0020058, US 2009/0263407 and US 2009/0285881 and PCT patent applications: WO 2009/086558, WO2009/127060, WO2009/132131, WO2010/042877, WO2010/054384, WO2010/054401, WO2010/054405 and WO2010/054406). See also Semple S. C. et al., Rational design of cationic lipids for siRNA delivery, *Nature Biotechnology*, 2010, 28, 172-176.

Other cationic lipids are disclosed in US patent applications: US 2009/0263407, US 2009/0285881, US 2010/0055168, US 2010/0055169, US 2010/0063135, US 2010/0076055, US 2010/0099738 and US 2010/0104629.

Traditional cationic lipids such as CLinDMA and DLinDMA have been employed for siRNA delivery to liver but suffer from non-optimal delivery efficiency along with liver toxicity at higher doses. It is an object of the instant invention to provide a cationic lipid scaffold that demonstrates enhanced efficacy along with lower liver toxicity as a result of lower lipid levels in the liver. The present invention employs low molecular weight cationic lipids with one short lipid chain to enhance the efficiency and tolerability of in vivo delivery of siRNA.

SUMMARY OF THE INVENTION

The instant invention provides for novel cationic lipids that can be used in combination with other lipid components such as cholesterol and PEG-lipids to form lipid nanoparticles with oligonucleotides. It is an object of the instant invention to provide a cationic lipid scaffold that demonstrates enhanced efficacy along with lower liver toxicity as a result of lower lipid levels in the liver. The present invention employs low molecular weight cationic lipids with one short lipid chain to enhance the efficiency and tolerability of in vivo delivery of siRNA.

DETAILED DESCRIPTION OF THE INVENTION

Figure 1:
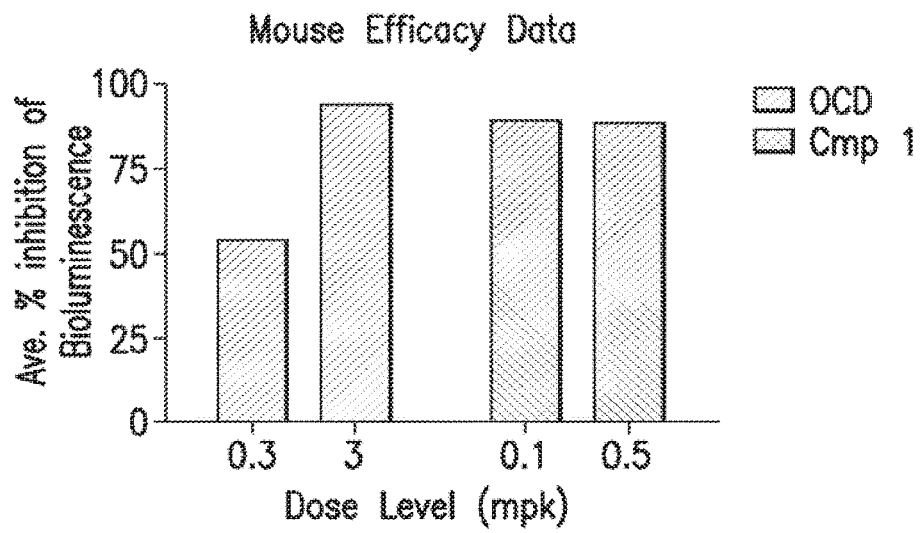
FIG. 1: LNP (Compound 1) efficacy in mice.

The various aspects and embodiments of the invention are directed to the utility of novel cationic lipids useful in lipid nanoparticles to deliver oligonucleotides, in particular, siRNA and miRNA, to any target gene. (See US patent applications: US 2006/0083780, US 2006/0240554, US 2008/0020058, US 2009/0263407 and US 2009/0285881 and PCT patent applications: WO 2009/086558, WO2009/127060, WO2009/132131, WO2010/042877, WO2010/054384, WO2010/054401, WO2010/054405 and WO2010/054406). See also Semple S. C. et al., Rational design of cationic lipids for siRNA delivery, *Nature Biotechnology*, 2010, 28, 172-176.

The cationic lipids of the instant invention are useful components in a lipid nanoparticle for the delivery of oligonucleotides, specifically siRNA and miRNA.

In a first embodiment of this invention, the cationic lipids are illustrated by the Formula A:

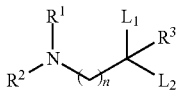

R¹ and R² are independently selected from H, ($C_1$-$C_6$) alkyl, heterocyclyl, and polyamine, wherein said alkyl, heterocyclyl and polyamine are optionally substituted with one to three substituents selected from R', or R¹ and R² can be taken together with the nitrogen to which they are attached to form a monocyclic heterocycle with 4-7 members optionally containing, in addition to the nitrogen, one or two additional heteroatoms selected from N, O and S, said monocyclic heterocycle is optionally substituted with one to three substituents selected from R';

R³ is independently selected from H and ($C_1$-$C_6$)alkyl, said alkyl optionally substituted with one to three substituents selected from R';

R' is independently selected from halogen, R", OR", SR", CN, $CO_2$R" or CON(R")$_2$;

R" is independently selected from H and ($C_1$-$C_6$)alkyl, wherein said alkyl is optionally substituted with halogen and OH;

n is 0, 1, 2, 3, 4 or 5;

$L_1$ is selected from $C_4$-$C_{24}$ alkyl and $C_4$-$C_{24}$ alkenyl, said alkyl and alkenyl are optionally substituted with one or more substituents selected from R'; and $L_2$ is selected from $C_3$-$C_9$ alkyl and $C_3$-$C_9$ alkenyl, said alkyl and alkenyl are optionally substituted with one or more substituents selected from R';

or any pharmaceutically acceptable salt or stereoisomer thereof.

In a second embodiment, the invention features a compound having Formula A, wherein:
R¹ and R² are each methyl;
R³ is H;
n is 0;
$L_1$ is selected from $C_4$-$C_{24}$ alkyl and $C_4$-$C_{24}$ alkenyl; and
$L_2$ is selected from $C_3$-$C_9$ alkyl and $C_3$-$C_9$ alkenyl;
or any pharmaceutically acceptable salt or stereoisomer thereof.

In a third embodiment, the invention features a compound having Formula A, wherein:
R¹ and R² are each methyl;
R³ is H;
n is 2;
$L_1$ is selected from $C_4$-$C_{24}$ alkyl and $C_4$-$C_{24}$ alkenyl; and
$L_2$ is selected from $C_3$-$C_9$ alkyl and $C_3$-$C_9$ alkenyl;
or any pharmaceutically acceptable salt or stereoisomer thereof.

Specific cationic lipids are:
(20Z,23Z)—N,N-dimethylnonacosa-20,23-dien-10-amine (Compound 1);
(17Z,20Z)—N,N-dimethylhexacosa-17,20-dien-9-amine (Compound 2);
(16Z,19Z)—N,N-dimethylpentacosa-16,19-dien-8-amine (Compound 3);
(13Z,16Z)—N,N-dimethyldocosa-13,16-dien-5-amine (Compound 4);
(12Z,15Z)—N,N-dimethylhenicosa-12,15-dien-4-amine (Compound 5);
(14Z,17Z)—N,N-dimethyltricosa-14,17-dien-6-amine (Compound 6);
(15Z,18Z)—N,N-dimethyltetracosa-15,18-dien-7-amine (Compound 7);
(18Z,21Z)—N,N-dimethylheptacosa-18,21-dien-10-amine (Compound 8);
(15Z,18Z)—N,N-dimethyltetracosa-15,18-dien-5-amine (Compound 9);
(14Z,17Z)—N,N-dimethyltricosa-14,17-dien-4-amine (Compound 10);
(19Z,22Z)—N,N-dimethyloctacosa-19,22-dien-9-amine (Compound 11);
(18Z,21Z)—N,N-dimethylheptacosa-18,21-dien-8-amine (Compound 12);
(17Z,20Z)—N,N-dimethylhexacosa-17,20-dien-7-amine (Compound 13);
(16Z,19Z)—N,N-dimethylpentacosa-16,19-dien-6-amine (Compound 14);
(22Z,25Z)—N,N-dimethylhentriaconta-22,25-dien-10-amine (Compound 15);
(21Z,24Z)—N,N-dimethyltriaconta-21,24-dien-9-amine (Compound 16);
(18Z)—N,N-dimethylheptacos-18-en-10-amine (Compound 17);
(17Z)—N,N-dimethylhexacos-17-en-9-amine (Compound 18);
(19Z,22Z)—N,N-dimethyloctacosa-19,22-dien-7-amine (Compound 19); and
N,N-dimethylheptacosa-10-amine (Compound 20);
(20Z,23Z)—N-ethyl-N-methylnonacosa-20,23-dien-10-amine (Compound 21);
1-[(11Z,14Z)-1-nonylicosa-11,14-dien-1-yl]pyrrolidine (Compound 22);
(20Z)—N,N-dimethylheptacos-20-en-10-amine (Compound 23);
(15Z)—N,N-dimethylheptacos-15-en-10-amine (Compound 24);
(14Z)—N,N-dimethylnonacos-14-en-10-amine (Compound 25);
(17Z)—N,N-dimethylnonacos-17-en-10-amine (Compound 26);
(24Z)—N,N-dimethyltritriacont-24-en-10-amine (Compound 27);
(20Z)—N,N-dimethylnonacos-20-en-10-amine (Compound 28);
(22Z)—N,N-dimethylhentriacont-22-en-10-amine (Compound 29);
(16Z)—N,N-dimethylpentacos-16-en-8-amine (Compound 30);
(12Z,15Z)—N,N-dimethyl-2-nonylhenicosa-12,15-dien-1-amine (Compound 31);
(13Z,16Z)—N,N-dimethyl-3-nonyldocosa-13,16-dien-1-amine (Compound 32);
N,N-dimethyl-1-[(1S,2R)-2-octylcyclopropyl]hepladecan-8-amine (Compound 33);
1-[(1S,2R)-2-hexylcyclopropyl]-N,N-dimethylnonadecan-10-amine (Compound 34);
N,N-dimethyl-1-[(1S,2R)-2-octylcyclopropyl]nonadecan-10-amine (Compound 35);
N,N-dimethyl-21-[(1S,2R)-2-octylcyclopropyl]henicosan-10-amine (Compound 36);
N,N-dimethyl-[(1S,2S)-2-{[(1R,2R)-2-pentylcyclopropyl]methyl}cyclopropyl]nonadecan-10-amine (Compound 37);
N,N-dimethyl-1-[(1S,2R)-2-octylcyclopropyl]hexadecan-8-amine (Compound 38);

N,N-dimethyl-1-[(1R,2S)-2-undecylcyclopropyl]tetradecan-5-amine (Compound 39);

N,N-dimethyl-3-{7-[(1S,2R)-2-octylcyclopropyl]heptyl}dodecan-1-amine (Compound 40)

1-[(1R,2S)-2-heptylcyclopropyl]-N,N-dimethyloctadecan-9-amine (Compound 41);

1-[(1S,2R)-2-decylcyclopropyl]-N,N-dimethylpentadecan-6-amine (Compound 42);

N,N-dimethyl-1-[(1S,2R)-2-octylcyclopropyl]pentadecan-8-amine (Compound 43); and (11E,20Z,23Z)—N,N-dimethylnonacosa-11,20,23-trien-10-amine (Compound 44);

or any pharmaceutically acceptable salt or stereoisomer thereof.

In another embodiment, the cationic lipids disclosed are useful in the preparation of lipid nanoparticles.

In another embodiment, the cationic lipids disclosed are useful components in a lipid nanoparticle for the delivery of oligonucleotides.

In another embodiment, the cationic lipids disclosed are useful components in a lipid nanoparticle for the delivery of siRNA and miRNA.

In another embodiment, the cationic lipids disclosed are useful components in a lipid nanoparticle for the delivery of siRNA.

The cationic lipids of the present invention may have asymmetric centers, chiral axes, and chiral planes (as described in: E. L. Eliel and S. H. Wilen, Stereochemistry of Carbon Compounds, John Wiley & Sons, New York, 1994, pages 1119-1190), and occur as racemates, racemic mixtures, and as individual diastereomers, with all possible isomers and mixtures thereof, including optical isomers, being included in the present invention. In addition, the cationic lipids disclosed herein may exist as tautomers and both tautomeric forms are intended to be encompassed by the scope of the invention, even though only one tautomeric structure is depicted.

It is understood that substituents and substitution patterns on the cationic lipids of the instant invention can be selected by one of ordinary skill in the art to provide cationic lipids that are chemically stable and that can be readily synthesized by techniques known in the art, as well as those methods set forth below, from readily available starting materials. If a substituent is itself substituted with more than one group, it is understood that these multiple groups may be on the same carbon or on different carbons, so long as a stable structure results.

It is understood that one or more Si atoms can be incorporated into the cationic lipids of the instant invention by one of ordinary skill in the art to provide cationic lipids that are chemically stable and that can be readily synthesized by techniques known in the art from readily available starting materials.

In the compounds of Formula A, the atoms may exhibit their natural isotopic abundances, or one or more of the atoms may be artificially enriched in a particular isotope having the same atomic number, but an atomic mass or mass number different from the atomic mass or mass number predominantly found in nature. The present invention is meant to include all suitable isotopic variations of the compounds of Formula A. For example, different isotopic forms of hydrogen (H) include protium ($^1$H) and deuterium ($^2$H). Protium is the predominant hydrogen isotope found in nature. Enriching for deuterium may afford certain therapeutic advantages, such as increasing in vivo half-life or reducing dosage requirements, or may provide a compound useful as a standard for characterization of biological samples. Isotopically-enriched compounds within Formula A can be prepared without undue experimentation by conventional techniques well known to those skilled in the art or by processes analogous to those described in the Scheme and Examples herein using appropriate isotopically-enriched reagents and/or intermediates.

As used herein, "alkyl" means a straight chain, cyclic or branched saturated aliphatic hydrocarbon having the specified number of carbon atoms.

As used herein, "alkenyl" means a straight chain, cyclic or branched unsaturated aliphatic hydrocarbon having the specified number of carbon atoms including but not limited to diene, triene and tetraene unsaturated aliphatic hydrocarbons.

Examples of a cyclic "alkyl" or "alkenyl" include:

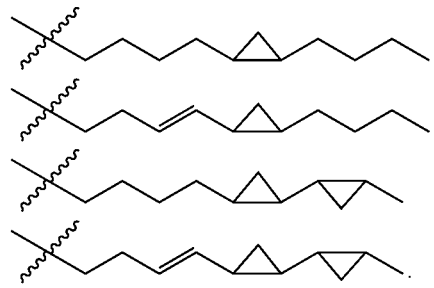

As used herein, "heterocyclyl" or "heterocycle" means a 4- to 10-membered aromatic or nonaromatic heterocycle containing from 1 to 4 heteroatoms selected from the group consisting of O, N and S, and includes bicyclic groups. "Heterocyclyl" therefore includes, the following: benzoinimidazolyl, benzofuranyl, benzofurazanyl, benzopyrazolyl, benzotriazolyl, benzothiophenyl, benzoxazolyl, carbazolyl, carbolinyl, cinnolinyl, furanyl, imidazolyl, indolinyl, indolyl, indolazinyl, indazolyl, isobenzofuranyl, isoindolyl, isoquinolyl, isothiazolyl, isoxazolyl, naphthpyridinyl, oxadiazolyl, oxazolyl, oxazoline, isoxazoline, oxetanyl, pyranyl, pyrazinyl, pyrazolyl, pyridazinyl, pyridopyridinyl, pyridazinyl, pyridyl, pyrimidyl, pyrrolyl, quinazolinyl, quinolyl, quinoxalinyl, tetrahydropyranyl, tetrazolyl, tetrazolopyridyl, thiadiazolyl, thiazolyl, thienyl, triazolyl, azetidinyl, 1,4-dioxanyl, hexahydroazepinyl, piperazinyl, piperidinyl, pyrrolidinyl, morpholinyl, thiomorpholinyl, dihydrobenzoimidazolyl, dihydrobenzofuranyl, dihydrobenzothiophenyl, dihydrobenzoxazolyl, dihydrofuranyl, dihydroimidazolyl, dihydroindolyl, dihydroisooxazolyl, dihydroisothiazolyl, dihydrooxadiazolyl, dihydrooxazolyl, dihydropyrazinyl, dihydropyrazolyl, dihydropyridinyl, dihydropyrimidinyl, dihydropyrrolyl, dihydroquinolinyl, dihydrotetrazolyl, dihydrothiadiazolyl, dihydrothiazolyl, dihydrothienyl, dihydrotriazolyl, dihydroazetidinyl, methylenedioxybenzoyl, tetrahydrofuranyl, and tetrahydrothienyl, and N-oxides thereof all of which are optionally substituted with one to three substituents selected from R".

As used herein, "polyamine" means compounds having two or more amino groups. Examples include putrescine, cadaverine, spermidine, and spermine.

As used herein, "halogen" means Br, Cl, F and I.

In an embodiment of Formula A, $R^1$ and $R^2$ are independently selected from H and $(C_1$-$C_6)$alkyl, wherein said alkyl is optionally substituted with one to three substituents selected from R', or $R^1$ and $R^2$ can be taken together with the nitrogen to which they are attached to form a monocyclic heterocycle with 4-7 members optionally containing, in addition to the nitrogen, one or two additional heteroatoms selected from N, O and S, said monocyclic heterocycle is optionally substituted with one to three substituents selected from R'.

In an embodiment of Formula A, $R^1$ and $R^2$ are independently selected from H, methyl, ethyl and propyl, wherein said methyl, ethyl and propyl are optionally substituted with one to three substituents selected from R', or $R^1$ and $R^2$ can be taken together with the nitrogen to which they are attached to form a monocyclic heterocycle with 4-7 members optionally containing, in addition to the nitrogen, one or two additional heteroatoms selected from N, O and S, said monocyclic heterocycle is optionally substituted with one to three substituents selected from R'.

In an embodiment of Formula A, $R^1$ and $R^2$ are independently selected from H, methyl, ethyl and propyl.

In an embodiment of Formula A, $R^1$ and $R^2$ are each methyl.

In an embodiment of Formula A, $R^3$ is independently selected from: H and methyl.

In an embodiment of Formula A, $R^3$ is H.

In an embodiment of Formula A, R' is R".

In an embodiment of Formula A, R" is independently selected from H, methyl, ethyl and propyl, wherein said methyl, ethyl and propyl are optionally substituted with one or more halogen and OH.

In on embodiment of Formula A, R" is independently selected from H, methyl, ethyl and propyl.

In an embodiment of Formula A, n is 0, 1, 2 or 3.

In an embodiment of Formula A, n is 0, 1 or 2.

In an embodiment of Formula A, n is 0, 1 or 2.

In an embodiment of Formula A, n is 0.

In an embodiment of Formula A, n is 2.

In an embodiment of Formula A, $L_1$ is selected from $C_4$-$C_{24}$ alkyl and $C_4$-$C_{24}$ alkenyl, which are optionally substituted with halogen and OH.

In an embodiment of Formula A, $L_1$ is selected from $C_4$-$C_{24}$ alkyl and $C_4$-$C_{24}$ alkenyl.

In an embodiment of Formula A, $L_1$ is selected from $C_4$-$C_{24}$ alkenyl.

In an embodiment of Formula A, $L_1$ is selected from $C_{12}$-$C_{24}$ alkenyl.

In an embodiment of Formula A, $L_1$ is $C_{19}$ alkenyl.

In an embodiment of Formula A, $L_1$ is:

In an embodiment of Formula A, $L_1$ is:

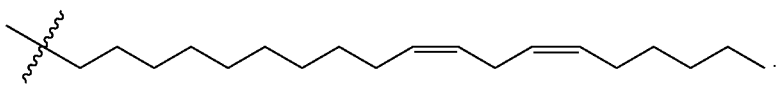

In an embodiment of Formula A, $L_2$ is selected from $C_3$-$C_9$ alkyl and $C_3$-$C_9$ alkenyl, which are optionally substituted with halogen and OH.

In an embodiment of Formula A, $L_2$ is selected from $C_5$-$C_9$ alkyl and $C_5$-$C_9$ alkenyl, which are optionally substituted with halogen and OH.

In an embodiment of Formula A, $L_2$ is selected from $C_7$-$C_9$ alkyl and $C_7$-$C_9$ alkenyl, which are optionally substituted with halogen and OH.

In an embodiment of Formula A, $L_2$ is selected from $C_3$-$C_9$ alkyl and $C_3$-$C_9$ alkenyl.

In an embodiment of Formula A, $L_2$ is selected from $C_5$-$C_9$ alkyl and $C_5$-$C_9$ alkenyl.

In an embodiment of Formula A, $L_2$ is selected from $C_7$-$C_9$ alkyl and $C_7$-$C_9$ alkenyl.

In an embodiment of Formula A, $L_2$ is $C_3$-$C_9$ alkyl.

In an embodiment of Formula A, $L_2$ is $C_5$-$C_9$ alkyl.

In an embodiment of Formula A, $L_2$ is $C_7$-$C_9$ alkyl.

In an embodiment of Formula A, $L_2$ is $C_9$ alkyl.

In an embodiment of Formula A, $L_1$ is selected from $C_4$-$C_{24}$ alkyl and $C_4$-$C_{24}$ alkenyl, said alkyl and alkenyl are optionally substituted with one or more substituents selected from R'; and $L_2$ is selected from $C_3$-$C_9$ alkyl and $C_3$-$C_9$ alkenyl, said alkyl and alkenyl are optionally substituted with one or more substituents selected from R'.

In an embodiment of Formula A, $L_1$ is selected from $C_{12}$-$C_{24}$ alkenyl, said alkenyl is optionally substituted with one or more substituents selected from R'; and $L_2$ is selected from $C_5$-$C_9$ alkyl, said alkyl is optionally substituted with one or more substituents selected from R'.

In an embodiment of Formula A, $L_1$ is selected from $C_{19}$ alkenyl, said alkenyl is optionally substituted with one or more substituents selected from R'; and $L_2$ is selected from $C_7$-$C_9$ alkyl, said alkyl is optionally substituted with one or more substituents selected from R'.

In an embodiment of Formula A, $L_1$ is selected from $C_{19}$ alkenyl, said alkenyl is optionally substituted with one or more substituents selected from R'; and $L_2$ is selected from $C_9$ alkyl, said alkyl is optionally substituted with one or more substituents selected from R'.

In an embodiment of Formula A, $L_1$ is selected from a straight chain $C_{19}$ alkenyl, said alkenyl is optionally substituted with one or more substituents selected from R'; and $L_2$ is selected from a straight chain $C_9$ alkyl, said alkyl is optionally substituted with one or more substituents selected from R'.

In an embodiment of Formula A, "heterocyclyl" is pyrolidine, piperidine, morpholine, imidazole or piperazine.

In an embodiment of Formula A, "monocyclic heterocyclyl" is pyrolidine, piperidine, morpholine, imidazole or piperazine.

In an embodiment of Formula A, "polyamine" is putrescine, cadaverine, spermidine or spermine.

In an embodiment, "alkyl" is a straight chain saturated aliphatic hydrocarbon having the specified number of carbon atoms.

In an embodiment, "alkenyl" is a straight chain unsaturated aliphatic hydrocarbon having the specified number of carbon atoms.

Included in the instant invention is the free form of cationic lipids of Formula A, as well as the pharmaceutically acceptable salts and stereoisomers thereof. Some of the isolated specific cationic lipids exemplified herein are the protonated salts of amine cationic lipids. The term "free form" refers to the amine cationic lipids in non-salt form. The encompassed pharmaceutically acceptable salts not only include the isolated salts exemplified for the specific cationic lipids described herein, but also all the typical pharmaceutically acceptable salts of the free form of cationic lipids of Formula A. The free form of the specific salt cationic lipids described may be isolated using techniques known in the art. For example, the free form may be regenerated by heating the salt with a suitable dilute aqueous base solution such as dilute aqueous NaOH, potassium carbonate, ammonia and sodium bicarbonate. The free forms may differ from their respective salt forms somewhat in certain physical properties, such as solubility in polar solvents, but the acid and base salts are otherwise pharmaceutically equivalent to their respective free forms for purposes of the invention.

The pharmaceutically acceptable salts of the instant cationic lipids can be synthesized from the cationic lipids of this invention which contain a basic or acidic moiety by conventional chemical methods. Generally, the salts of the basic cationic lipids are prepared either by ion exchange chromatography or by reacting the free base with stoichiometric amounts or with an excess of the desired salt-forming inorganic or organic acid in a suitable solvent or various combinations of solvents. Similarly, the salts of the acidic compounds are formed by reactions with the appropriate inorganic or organic base.

Thus, pharmaceutically acceptable salts of the cationic lipids of this invention include the conventional non-toxic salts of the cationic lipids of this invention as formed by reacting a basic instant cationic lipids with an inorganic or organic acid. For example, conventional non-toxic salts include those derived from inorganic acids such as hydrochloric, hydrobromic, sulfuric, sulfamic, phosphoric, nitric and the like, as well as salts prepared from organic acids such as acetic, propionic, succinic, glycolic, stearic, lactic, malic, tartaric, citric, ascorbic, pamoic, maleic, hydroxymaleic, phenylacetic, glutamic, benzoic, salicylic, sulfanilic, 2-acetoxy-benzoic, fumaric, toluenesulfonic, methanesulfonic, ethane disulfonic, oxalic, isethionic, trifluoroacetic (TFA) and the like.

When the cationic lipids of the present invention are acidic, suitable "pharmaceutically acceptable salts" refers to salts prepared form pharmaceutically acceptable non-toxic bases including inorganic bases and organic bases. Salts derived from inorganic bases include aluminum, ammonium, calcium, copper, ferric, ferrous, lithium, magnesium, manganic salts, manganous, potassium, sodium, zinc and the like. Particularly preferred are the ammonium, calcium, magnesium, potassium and sodium salts. Salts derived from pharmaceutically acceptable organic non-toxic bases include salts of primary, secondary and tertiary amines, substituted amines including naturally occurring substituted amines, cyclic amines and basic ion exchange resins, such as arginine, betaine caffeine, choline, N,N¹-dibenzylethylenediamine, diethylamine, 2-diethylaminoethanol, 2-dimethylaminoethanol, ethanolamine, ethylenediamine, N-ethylmorpholine, N-ethylpiperidine, glucamine, glucosamine, histidine, hydrabamine, isopropylamine, lysine, methylglucamine, morpholine, piperazine, piperidine, polyamine resins, procaine, purines, theobromine, triethylamine, trimethylamine tripropylamine, tromethamine and the like.

The preparation of the pharmaceutically acceptable salts described above and other typical pharmaceutically acceptable salts is more fully described by Berg et al., "Pharmaceutical Salts," *J. Pharm. Sci.*, 1977:66:1-19.

It will also be noted that the cationic lipids of the present invention are potentially internal salts or zwitterions, since under physiological conditions a deprotonated acidic moiety in the compound, such as a carboxyl group, may be anionic, and this electronic charge might then be balanced off internally against the cationic charge of a prolonated or alkylated basic moiety, such as a quaternary nitrogen atom.

EXAMPLES

Examples provided are intended to assist in a further understanding of the invention. Particular materials employed, species and conditions are intended to be further illustrative of the invention and not limitative of the reasonable scope thereof. The reagents utilized in synthesizing the cationic lipids are either commercially available or are readily prepared by one of ordinary skill in the art.

Synthesis of the novel cationic lipids is a linear process starting from lipid acid (I). Coupling to N,O-dimethyl hydroxylamine gives the Weinreb amide II. Grignard addition generates ketone III. Titanium mediated reductive amination gives final products of type IV.

GENERAL SCHEME 1

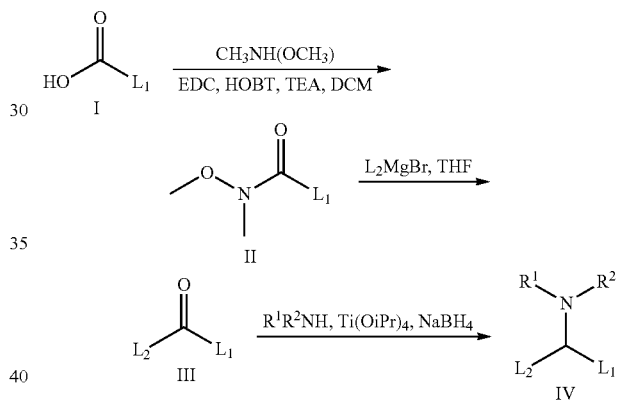

Synthesis of the single carbon homologated cationic lipids V is a linear process starting from lipid ketone (III). Conversion of the ketone to the nitrile (V) is accomplished via treatment with TOSMIC and potassium tert-butoxide. Reduction of the nitrile to the primary amine followed by reductive amination provides final cationic lipids VI.

GENERAL SCHEME 2

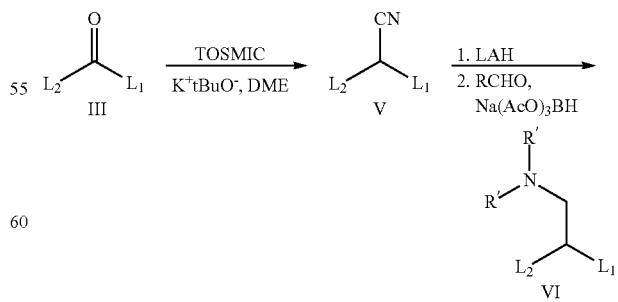

Synthesis of two carbon homologated cationic lipids IX is a linear process starting from lipid ketone (III). Conversion of the ketone to the α,β-unsaturated amide VII is accomplished under Peterson conditions. Conjugate reduction of the α,β-unsaturation is performed using LS-Selectride to give amide VIII. Reduction of the amide with lithium aluminum hydride provides final cationic lipids IX.

Cyclopropyl containing lipids are prepared according to General Scheme 4. Unsaturated Weinreb amides II are subjected to Simmons-Smith cyclopropanation conditions to give cyclopropyl containing Weinreb amides X. These are carried on to final products as outlined in General Schemes 1-3.

Synthesis of allylic amine cationic lipids XVI is a linear process starting with aldehyde XI. Addition of t-butyl aceate generates β-hydroxy ester XII. Conversion of the hydroxyl functionality to a fluoro group followed by acid treatment generates β-fluoro acid XIII. Conversion of the acid to the Weinreb amide followed by Grignard addition gives the β-fluoro ketone XV. Reductive amination results in simultaneous elimination to generate the desired allylic amine XVI.

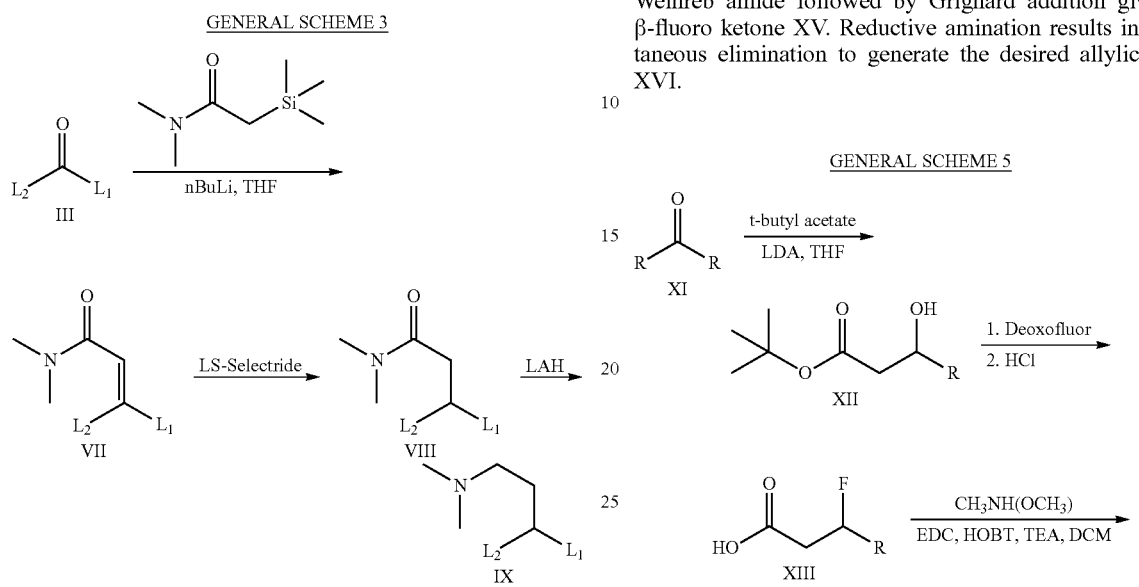

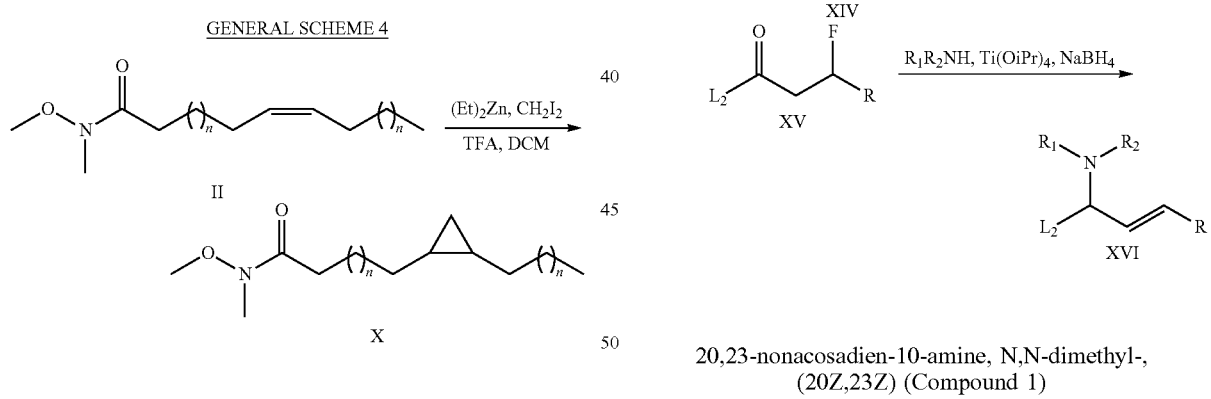

20,23-nonacosadien-10-amine, N,N-dimethyl-, (20Z,23Z) (Compound 1)

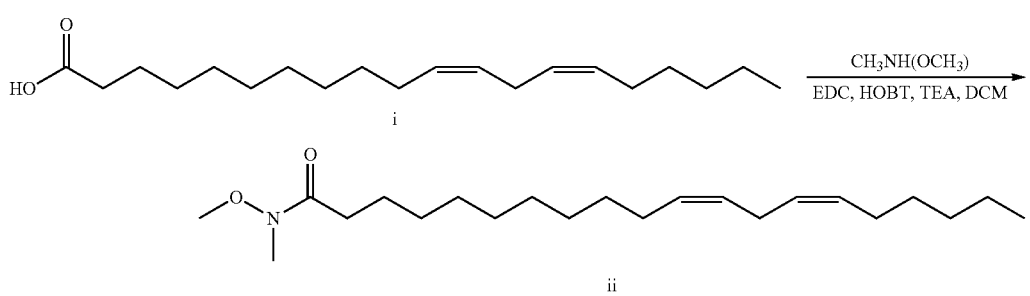

11,14-Eicosadienoic acid, (11Z,14Z)—(50 g, 162 mmol), N,O-Dimethylhydroxylamine hydrochloride (31.6 g, 324 mmol), HOAt (44.1 g, 324 mmol), Et$_3$N (45.2 ml, 324 mmol), and EDC (62.1 g, 324 mmol) were mixed in DCM (810 mL) and stirred overnight at ambient temperature. Reaction was then washed 5×700 mL water, then washed 1×600 mL 1 M NaOH, dried with sodium sulfate, filtered through celite and evaporated to obtain 53.06 g (93%) 11,14-eicosadienamide, N-methoxy-N-methyl-, (11Z,14Z) as a clear golden oil. $^1$H NMR (400 MHz, CDCl$_3$) δ 5.35 (m, 4H), 3.68 (s, 3H), 3.18 (s, 3H), 2.77 (m, 2H), 2.41 (t, J=7 Hz, 2H), 2.05 (m, 4H), 1.63 (m, 2H), 1.40-1.26 (m, 18H), 0.89 (t, J=7 Hz, 3H).

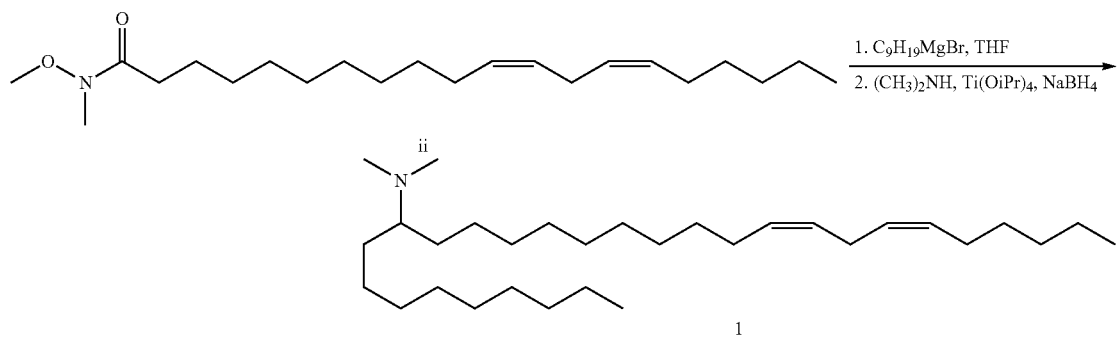

11,14-eicosadienamide, N-methoxy-N-methyl-, (11Z, 14Z)—1 (4 g, 11.38 mmol) was dissolved in dry THF (50.0 ml) in a 250 mL flask then 1 M nonylmagnesium bromide (22.76 ml, 22.76 mmol) was added under nitrogen at ambient temperature. After 10 min, the reaction was slowly quenched with excess sat. aq NH$_4$Cl. The reaction was washed into a separatory funnel with hexane and water, shaken, the lower aqueous layer discarded, the upper layer dried with sodium sulfate, filtered, and evaporated to give crude ketone as a golden oil. To the above crude ketone was added dimethylamine (2 M in THF) (14.22 ml, 28.4 mmol) followed by Ti(O-i-Pr)$_4$ (6.67 ml, 22.76 mmol) and let stir overnight. The next day, added EtOH (50 ml) followed by NaBH$_4$ (0.646 g, 17.07 mmol). After 5 min of stirring, directly injected entire reaction onto a 40 g silica column that was in line with a 330 g silica column. Eluted 10 min 100% DCM, then 30 min 0-15% MeOH/DCM, collected 20,23-nonacosadien-10-amine, N,N-dimethyl-, (20Z,23Z) (J) (2.45 g, 5.47 mmol, 48.1% yield) as a faintly golden oil. $^1$H NMR (400 MHz, CDCl$_3$) δ 5.35 (m, 4H), 2.78 (m, 2H), 2.23 (m, 1H), 2.21 (s, 6H), 2.05 (m, 4H), 1.45-1.16 (m, 38H), 0.89 (m, 6H) HRMS calcd for C$_{31}$H$_{61}$N 448.4877, found 448.4872.

Compounds 2-30 are novel cationic lipids and were prepared according to the General Scheme 1 above.

| Compound | Structure | HRMS |
|---|---|---|
| 2 | 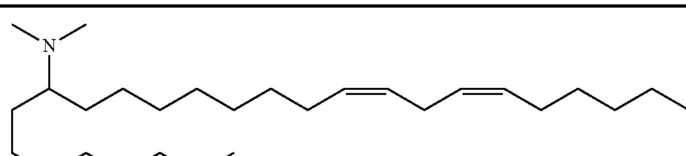 | calcd C28H56N 406.4407, found 406.4405. |
| 3 | 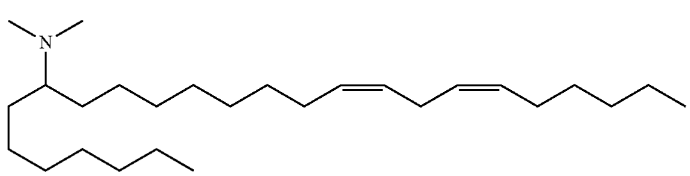 [SMILES: CCCCC/C=C\C/C=C\CCCCCCCC(CCCCCCC)N(C)C] | calcd C24H54N 392.4251, found 392.4250 |
| 4 | 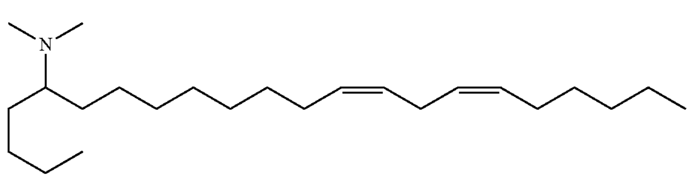 [SMILES: CCCCC/C=C\C/C=C\CCCCCCCC(CCCC)N(C)C] | calcd C24H48N 350.3781, found 350.3770. |

-continued

| Compound | Structure | HRMS |
|---|---|---|
| 5 | 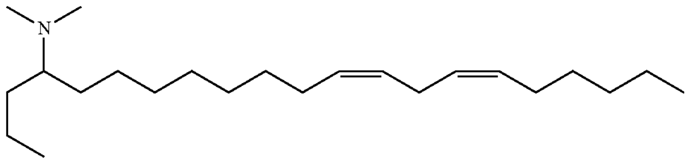 [SMILES: CCCCC/C=C\C/C=C\CCCCCCCC(CCC)N(C)C] | calcd C23H46N 336.3625, found 336.3613. |
| 6 | 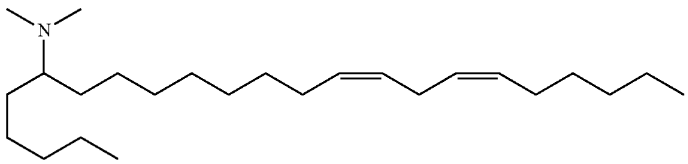 [SMILES: CCCCC/C=C\C/C=C\CCCCCCCC(CCCCC)N(C)C] | calcd C25H50N 364.3938, found 364.3941 |
| 7 | 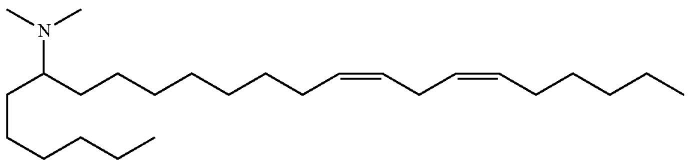 | calcd C26H52N 378.4094, found 378.4081. |
| 8 | 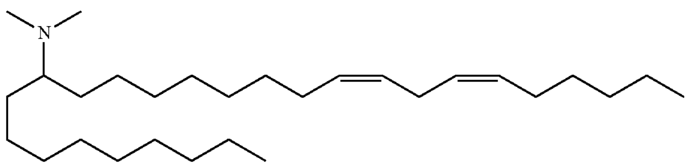 [SMILES: CCCCC/C=C\C/C=C\CCCCCCCC(CCCCCCCCC)N(C)C] | calcd C29H58N 420.4564, found 420.4562. |
| 9 | 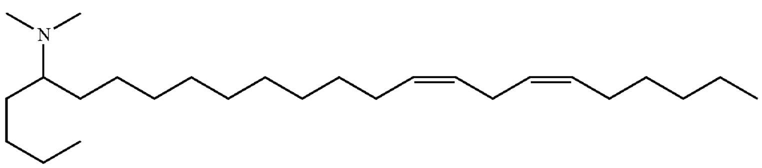 [SMILES: CCCCC/C=C\C/C=C\CCCCCCCCCC(CCCC)N(C)C] | calcd C26H52N 378.4094, found 378.4089. |
| 10 | 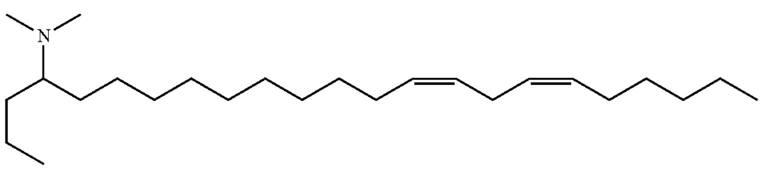 [SMILES: CCCCC/C=C\C/C=C\CCCCCCCCCC(CCC)N(C)C] | calcd C25H50N 364.3938, found 364.3931. |
| 11 | 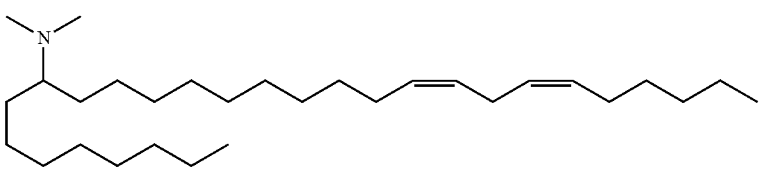 [SMILES: CCCCC/C=C\C/C=C\CCCCCCCCCC(CCCCCCCC)N(C)C] | calcd C30H60N 434.4720, found 434.4717. |
| 12 | 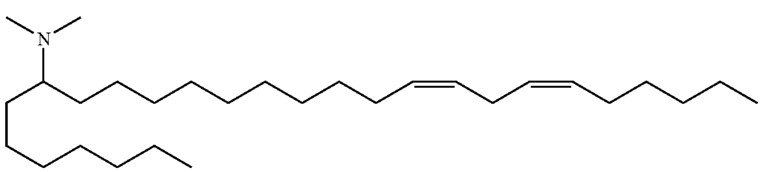 [SMILES: CCCCC/C=C\C/C=C\CCCCCCCCCC(CCCCCCC)N(C)C] | calcd C29H58N 420.4564, found 420.4561. |
| 13 | 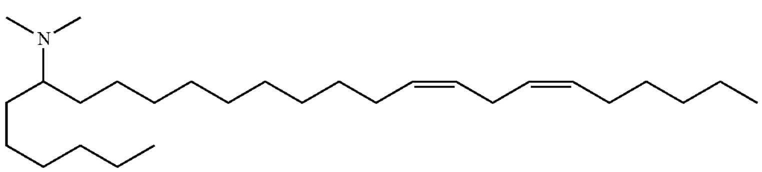 [SMILES: CCCCC/C=C\C/C=C\CCCCCCCCCC(CCCCCC)N(C)C] | calcd C28H56N 406.4407, found 406.4404. |

-continued

| Compound | Structure | HRMS |
|---|---|---|
| 14 | 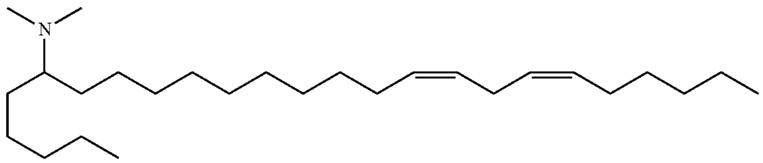 [SMILES: CCCCC/C=C\C/C=C\CCCCCCCCCC(CCCCC)N(C)C] | calcd C27H54N 392.4251, found 392.4245 |
| 15 | 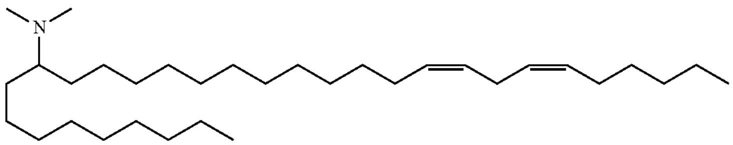 [SMILES: CCCCC/C=C\C/C=C\CCCCCCCCCCCC(CCCCCCCCC)N(C)C] | calcd C33H66N 476.5190, found 476.5196. |
| 16 | 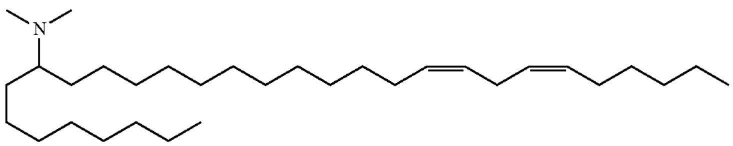 [SMILES: CCCCC/C=C\C/C=C\CCCCCCCCCCCC(CCCCCCCC)N(C)C] | calcd C32H64N 462.5033, found 462.5045. |
| 17 | 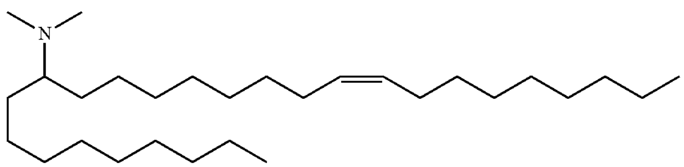 [SMILES: CCCCCCCC/C=C\CCCCCCCC(CCCCCCCCC)N(C)C] | calcd C29H59N 422.4720, found 422.4726. |
| 18 | 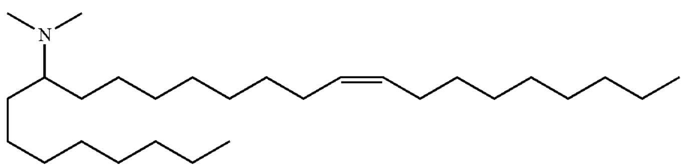 [SMILES: CCCCCCCC/C=C\CCCCCCCC(CCCCCCCC)N(C)C] | calcd C28H57N 408.4564, found 408.4570. |
| 19 | 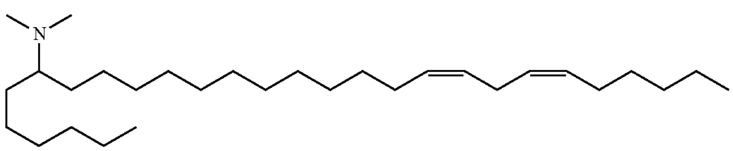 [SMILES: CCCCC/C=C\C/C=C\CCCCCCCCCCCC(CCCCCC)N(C)C] | calcd C30H59N 434.4720, found 434.4729 |
| 20 | 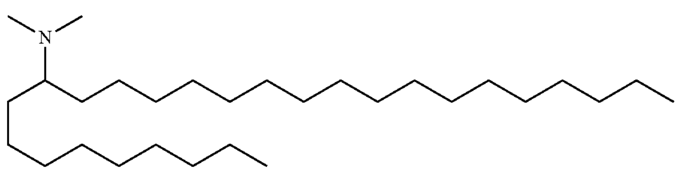 [SMILES: CCCCCCCCCCCCCCCCCC(CCCCCCCCC)N(C)C] | calcd C29H61N 424.4877, found 424.4875 |
| 21 | 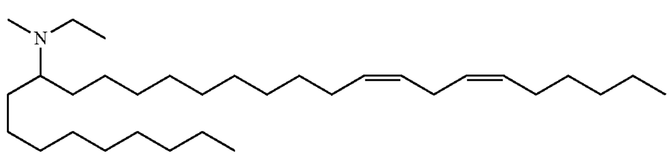 [SMILES: CCCCC/C=C\C/C=C\CCCCCCCCCC(CCCCCCCCC)N(C)CC] | calcd C32H64N 462.5033, found 462.5023. |
| 22 | 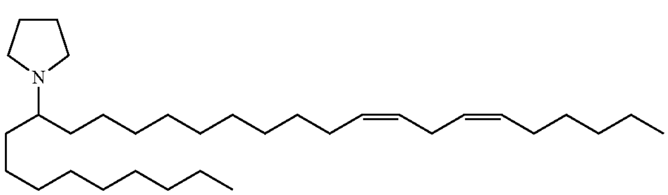 [SMILES: CCCCC/C=C\C/C=C\CCCCCCCCCC(CCCCCCCCC)N1CCCC1] | calcd C33H64N 474.5033, found 474.5033. |

-continued
| Compound | Structure | HRMS |
|---|---|---|
| 23 | 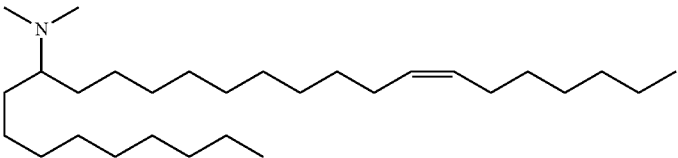 [SMILES: CCCCCC/C=C\CCCCCCCCCC(CCCCCCCCC)N(C)C] | calcd C29H60N 422.4720, found 422.4716. |
| 24 | 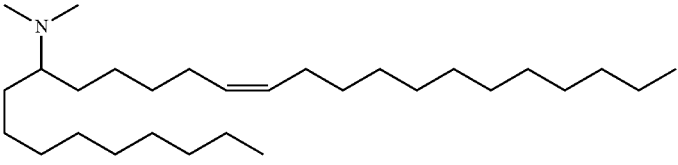 [SMILES: CCCCCCCCCCC/C=C\CCCCC(CCCCCCCCC)N(C)C] | calcd C29H60N 422.4720, found 422.4718. |
| 25 | 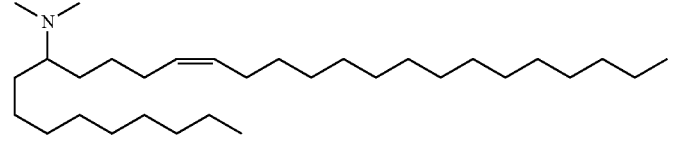 [SMILES: CCCCCCCCCCCCCC/C=C\CCCC(CCCCCCCCC)N(C)C] | calcd C31H64N 450.5033, found 450.5031. |
| 26 | 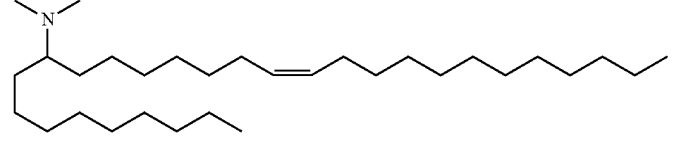 [SMILES: CCCCCCCCCCC/C=C\CCCCCCC(CCCCCCCCC)N(C)C] | calcd C31H64N 450.5033, found 450.5034. |
| 27 | 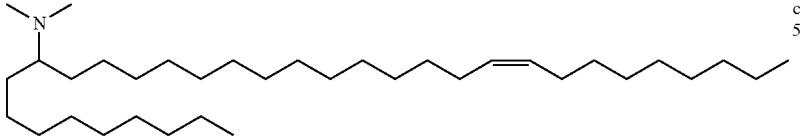 | calcd C35H72N 506.5659, found 506.5635. |
| 28 | 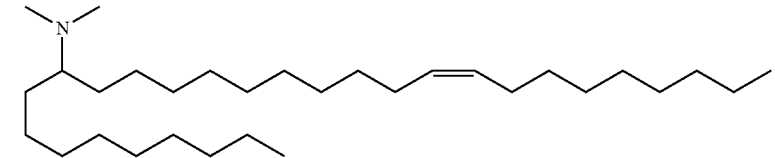 [SMILES: CCCCCCCC/C=C\CCCCCCCCCC(CCCCCCCCC)N(C)C] | calcd C31H64N 450.5033, found 450.5037. |
| 29 | 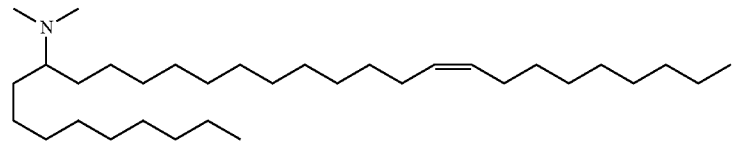 [SMILES: CCCCCCCC/C=C\CCCCCCCCCCCC(CCCCCCCCC)N(C)C] | calcd C33H68N 478.5346, found 478.5358. |
| 30 | 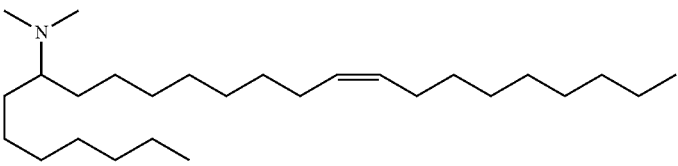 [SMILES: CCCCCCCC/C=C\CCCCCCCC(CCCCCCC)N(C)C] | calcd C27H56N 394.4407, found 394.4407. |

(12Z,15Z)—N,N-dimethyl-2-nonylhenicosa-12,15-dien-1-amine (Compound 31)

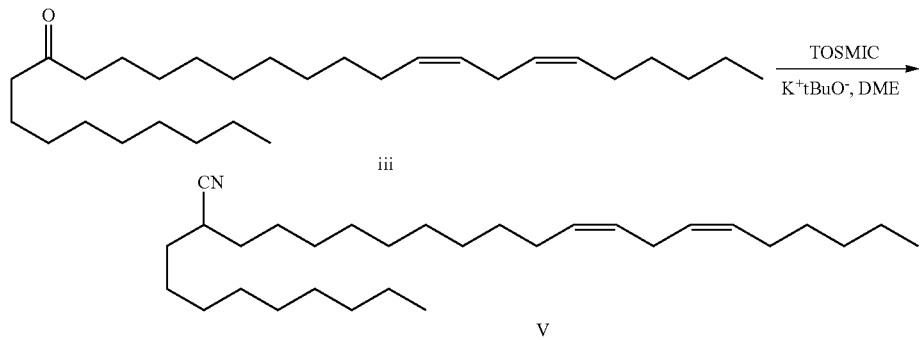

A solution of ketone iii (4.0 g, 9.55 mmol), TOSMIC (2.4 g, 12.4 mmol) in dimethoxyethane (45 mL) was cooled to 0° C. and treated with potassium tert-butoxide (19.1 mmol, 19.1 mL of a 1M solution in rBuOH). After 90 minutes, the reaction was partitioned between hexanes and water. The organics were washed with water, dried over sodium sulfate, filtered and evaporated in vacuo. This material was purified by flash chromatography (0-5% EtOAc/hexanes) to give desired product (containing ~20% of s.m.). This mixture was carried into next step as is. LC/MS (M+H)=430.6.

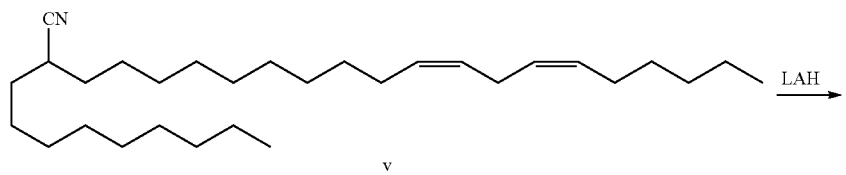

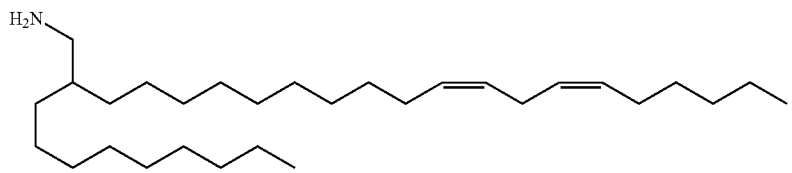

Lithium aluminum hydride (23.9 mmol, 23.9 mL of a 1M solution in THF) was added directly to nitrile v (3.42 g, 8 mmol) at ambient temperature and the reaction was stirred for 20 minutes. The reaction was diluted with 100 mL THF, cooled to 0° C. and carefully quenched with sodium sulfate decahydrate solution. The solids were filtered off and washed with THF. The filtrate was evaporated in vacuo and carried directly into next reaction crude.

LC/MS (M+H)=434.6.

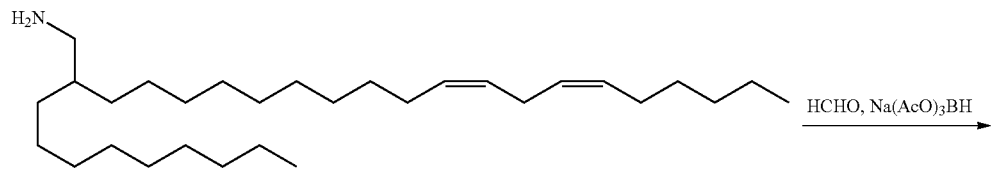

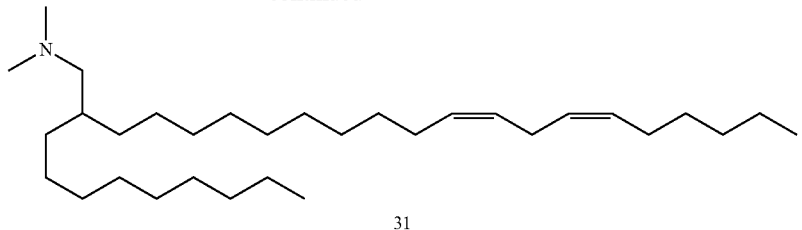

31

A solution of primary amine (3.45 g, 6.2 mmol) in dichloroethane (100 mL) was treated with formaldehyde (1.6 mL, 21.7 mmol) followed by sodium triacetoxyborohydride (6.6 g, 31 mmol). After 5 minutes, the reaction was partitioned between dichloromethane and 1N NaOH. The organics were dried over sodium sulfate, filtered and evaporated in vacuo. The crude mixture was purified by reverse phase preparative chromatography (C8 column) to provide (12Z,15Z)—N,N-dimethyl-2-nonylhenicosa-12,15-dien-1-amine. HRMS calc'd 462.5033, found 462.5026. $^1$H NMR (400 MHz, CDCl$_3$) δ 5.35 (m, 4H), 2.78 (2H, t, J=5.6 Hz), 2.18 (s, 6H), 2.05 (m, 6H), 1.3 (m, 39H), 0.89 (m, 6H).

(13Z,16Z)—N,N-dimethyl-3-noanyldocosa-13,16-dien-1-amine (Compound 32)

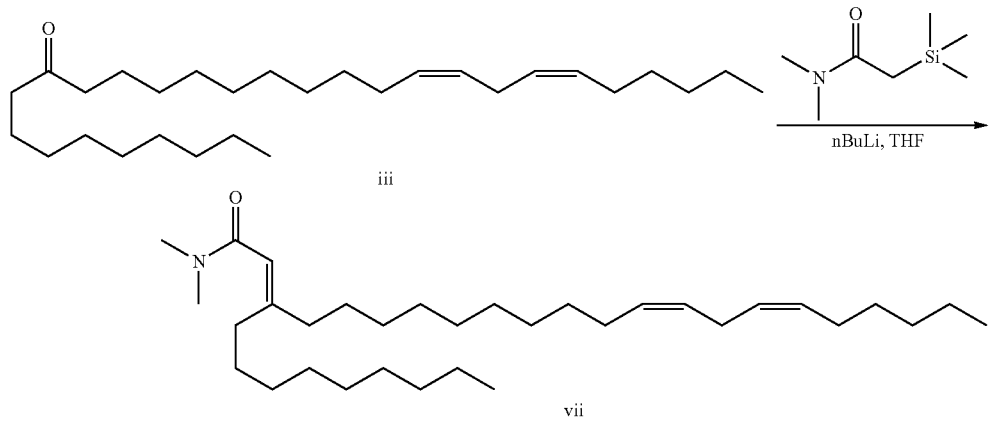

The silyl amide Peterson reagent (3.1 g, 16.7 mmol) was dissolved in THF (35 mL) and cooled to −63° C. To this solution was added nBuLi (16.7 mmol, 6.7 mL of a 2.5M solution). The reaction was warmed to ambient temperature for 30 minutes. The ketone (5.0 g, 11.9 mmol) was dissolved in THF (25 mL) in a second flask. The ketone solution was transferred to the Peterson reagent over 30 minutes while maintaining the temperature between −60° C. and −40° C. The reaction was warmed to −40° C. for 1 hour, then warmed to 0° C. for 30 minutes. The reaction was quenched with sodium bicarbonate, diluted with additional water and partitioned between water/hexanes. The organics were washed with brine, dried over sodium sulfate, filtered and evaporated in vacuo. Purification by flash chromatography (0-40% MTBE/hexanes) gave α,β-unsatured amide vii. $^1$H NMR (400 MHz, CDCl$_3$) δ 5.75 (s, 1H), 5.36 (m, 4H), 3.01 (s, 3H), 2.99 (s, 3H), 2.78 (t, 2H), 2.28 (t, 2H), 2.05 (m, 6H), 1.35 (m, 34H), 0.89 (m, 6H).

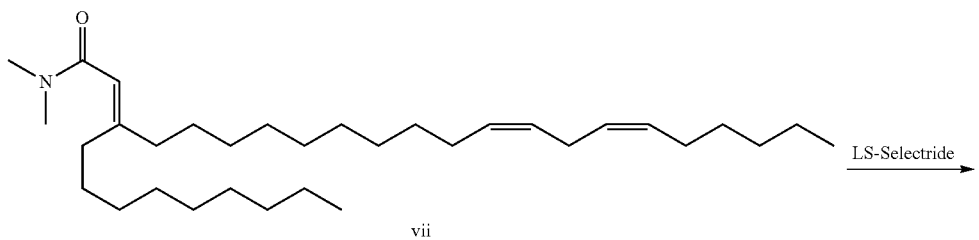

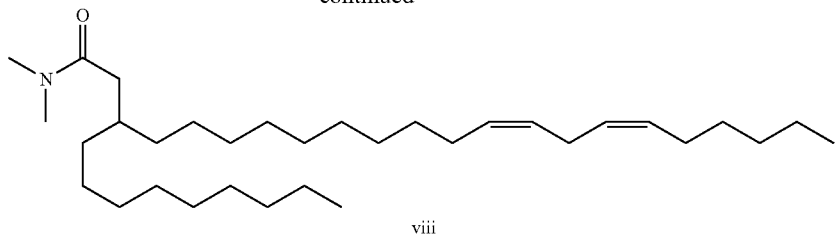

α,β-unsatured amide vii (1 g, 2.1 mmol) and LS-Selectride (4.1 mmol, 4.1 mL, of a 1M solution) were combined in a sealed tube and heated to 60° C. for 24 hours. The reaction was cooled to ambient temperature and partitioned between ammonium chloride solution and heptane. The organics were dried over sodium sulfate, filtered and evaporated in vacuo to give amide viii. This intermediate was carried directly into next reaction crude.

An alternative conjugate reduction of α,β-unsatured amide vii involves the use of a copper hydride reduction:

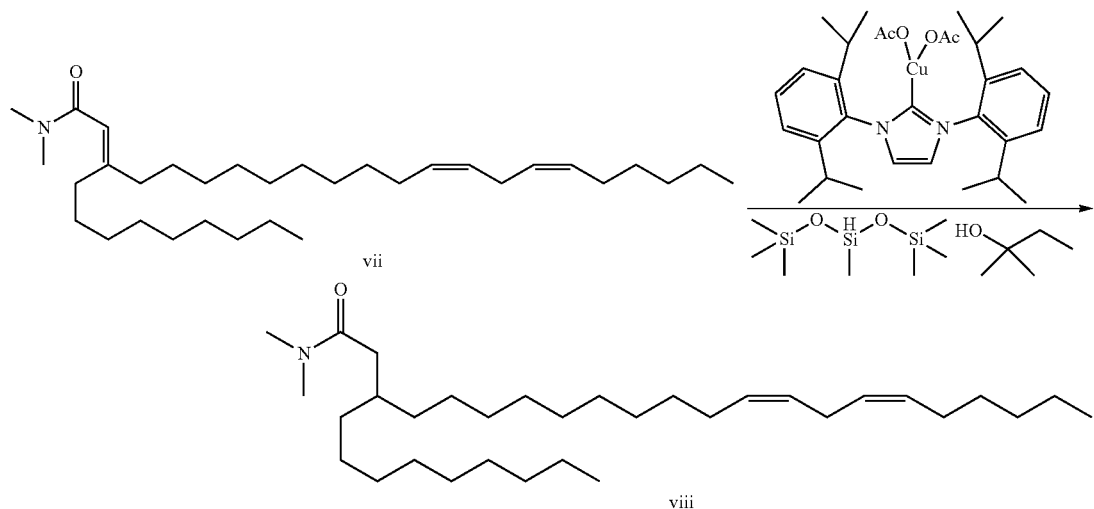

In a 5 L RB, the Copper catalyst (9.77 g, 17.13 mmol) was dissolved in toluene (1713 ml) under nitrogen. To this was added the PMHS, from Aldrich (304 ml, 1371 mmol) in a single portion. The reaction was aged for 5 minutes. To the solutions was added the α,β-unsatured amide vii (167.16 g, 343 mmol). To this mixture was then added the t-amyl alcohol (113 ml, 1028 mmol) over 3 h via syringe pump. After addition complete, to the solution was added ~1700 ml 20% NH4OH to rxn in small portions. Caution: there is vigorous effervescence and foaming in the beginning of the quench and it must be closely monitored and the ammonium hydroxide added slowly in small portions. The reaction was partitioned between water and hexanes. The organics were filtered through celite and evaporated in vacuo. The resulting rubber solid material was pulverized using a mechanical stirrer in hexanes to give small particulates which were then filtered and washed with hexanes. The organics were then evaporated in vacuo and purified by flash chromatography (silica, 0-15% ethyl acetate/hexanes) to give desired amide viii. LC/MS (M+H)=490.7.

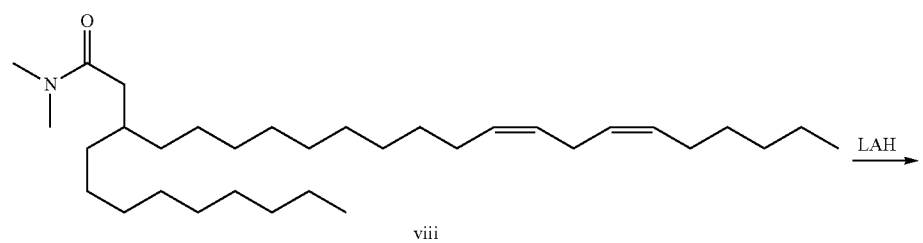

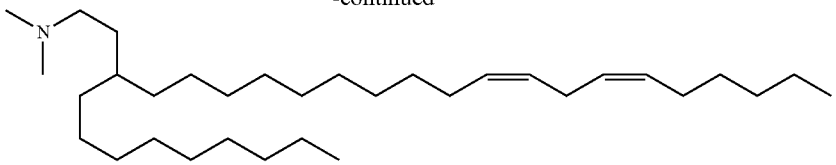

32

To a solution of amide viii (2.85 g, 5.8 mmol) was added lithium aluminum hydride (8.7 mmol, 8.7 mL of a 1M solution). The reaction was stirred at ambient temperature for 10 minutes then quenched by slow addition of sodium sulfate decahydrate solution. The solids were filtered and washed with THF and the filtrate evaporated in vacuo. The crude mixture was purified by reverse phase preparative chromatography (C8 column) to provide (13Z,16Z)—N,N-dimethyl-3-nonyldocosa-13,16-dien-1-amine (Compound 32) as an oil. HRMS (M+H) calc'd 476.5190, found 476.5189. $^1$H NMR (400 MHz, CDCl$_3$) δ 5.37 (m, 4H), 2.78 (t, 2H), 2.42 (m, 8H), 2.05 (q, 4H), 1.28 (m, 41H), 0.89 (m, 6H).

N,N-dimethyl-1-(2-octylcyclopropyl)heptadecan-8-amine (Compound 33)

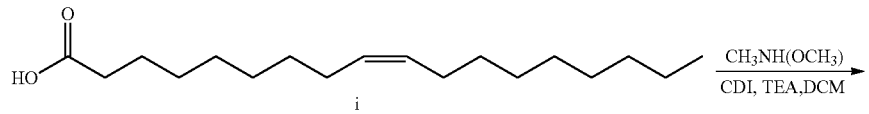

i

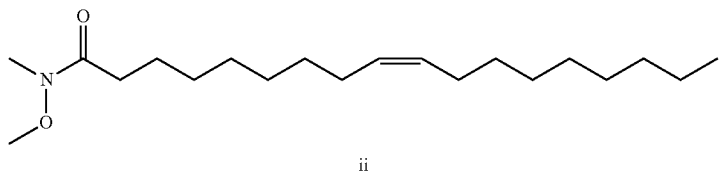

ii

To a solution of oleic acid (1 g, 3.5 mmol) in DCM (500 mL) cooled to 0° C. was added CDI (0.63 g, 3.9 mmol). The reaction was warmed to ambient temperature for 30 minutes before cooling to 0° C. and treating first with triethylamine (0.39 g, 3.9 mmol) and then dimethyl hydroxylamine hydrochloride (0.38 g, 3.9 mmol). After 1 hour the reaction was partitioned between water and heptane. The organics were dried over magnesium sulfate, filtered and evaporate in vacuo to give crude Weinreb amide ii which was carried directly into next reaction.

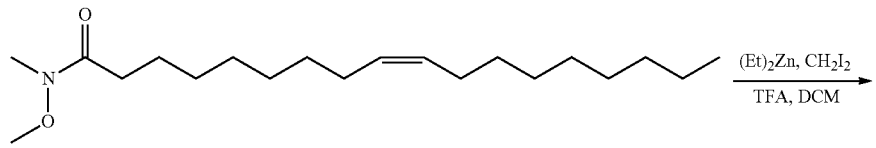

ii

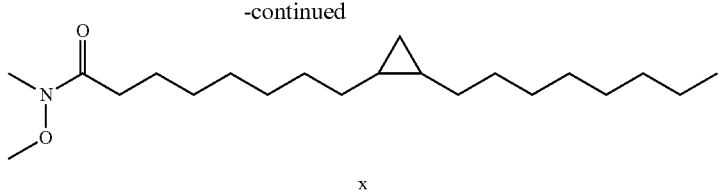

x

A solution of diethylzine (70.3 mmol, 70.3 ml, of a 1M solution) in dichloromethane (130 mL) was cooled to −1° C. and treated dropwise with TFA (8.0 g, 70.3 mmol). After 30 minutes, diiodomethane (18.8 g, 70.3 mmol) was added and this was aged for 30 minutes in the ice bath. To this solution was added Weinreb amide ii (7.6 g, 23.4 mmol). The reaction was warmed to ambient temperature, and stirred for 1 hour. The reaction was quenched with ammonium chloride solution (100 mL) and organic layer partitioned off, washed with 10% sodium thiosulfate, dried over magnesium sulfate, filtered and evaporated in vacuo. Purification was flash chromatography (0-30% MTBE/heptane) gave desired product x. $^1$H NMR (400 MHz, CHCl$_3$) δ 3.72 (s, 3H), 3.22 (s, 3H), 2.48 (t, 2H), 1.65 (m, 2H), 1.39 (m, 22H), 1.18 (m, 2H), 0.91 (t, 3H), 0.68 (m, 2H), 0.59 (m, 1H), −0.32 (m, 1H).

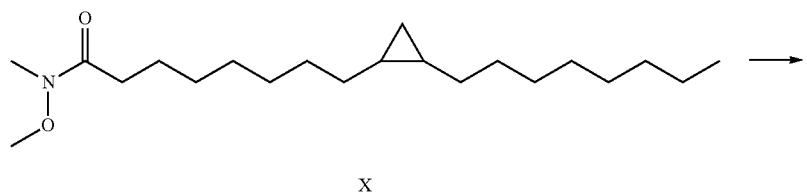

X

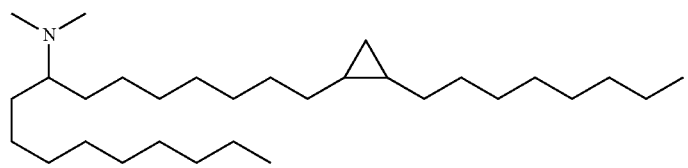

33

Conversion of Weinreb amide x to Compound 33 was carried out in a manner analogous to that described for Compound 1 above (nonyl Grignard addition followed by reductive animation). LC/MS (M+H)=436.6. $^1$H NMR (400 MHz, CDCl$_3$) δ 2.25 (s, 6H), 1.30 (m, 45H), 0.91 (m, 6H), 0.68 (m, 2H), 0.59 (m, 1H), −0.31 (m, 1H).

Compounds 34-43 are novel cationic lipids and were prepared according to General Schemes 1-4 above.

| Compound | Structure | HRMS |
|---|---|---|
| 34 | 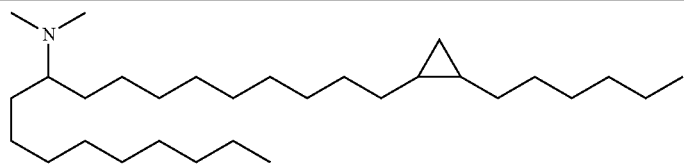 [SMILES: CCCCCCCCCC(CCCCCCCCCC1CC1CCCCCC)N(C)C] | calcd C30H62N 436.4877, found 436.4872. |

-continued

| Compound | Structure | HRMS |
|---|---|---|
| 35 | 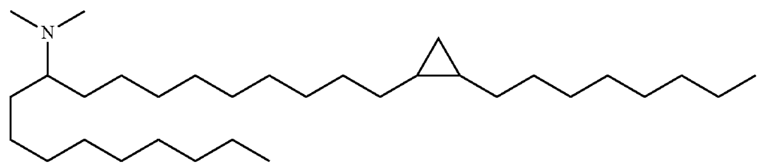 [SMILES: CCCCCCCCCC(CCCCCCCCCC1CC1CCCCCCCC)N(C)C] | calcd C32H66N 464.5190, found 464.5186. |
| 36 | 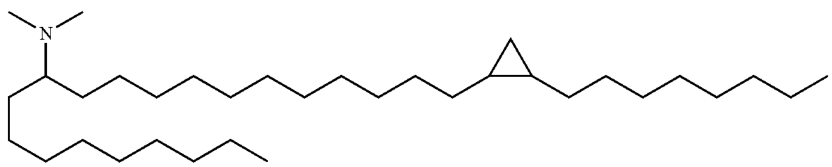 [SMILES: CCCCCCCCCC(CCCCCCCCCCCC1CC1CCCCCCCC)N(C)C] | calcd C34H70N 492.5503, found 492.5496. |
| 37 | 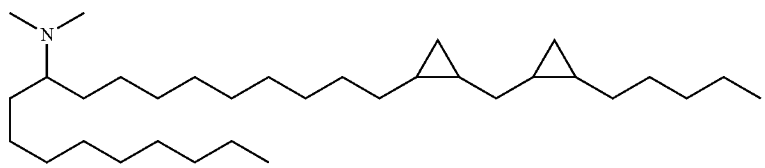 [SMILES: CCCCCCCCCC(CCCCCCCCCC1CC1CC1CC1CCCCC)N(C)C] | calcd C33H66N 476.5109, found 476.5174. |
| 38 | 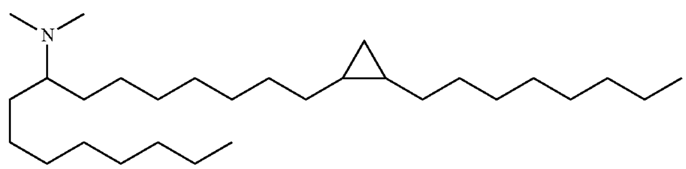 [SMILES: CCCCCCCCC1CC1CCCCCCCC(CCCCCCCC)N(C)C] | calcd C29H60N 422.4720, found 422.4701. |
| 39 | 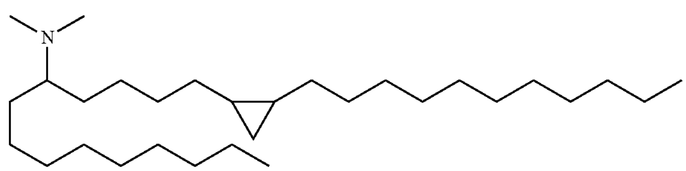 [SMILES: CCCCCCCCCCCC1CC1CCCCC(CCCCCCCCC)N(C)C] | calcd C30H62N 436.4877, found 436.4880. |
| 40 | 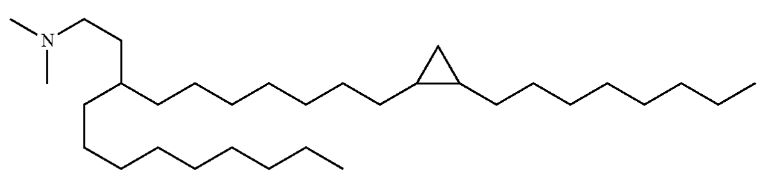 [SMILES: CCCCCCCCCC(CCCCCCCC1CC1CCCCCCCC)CCN(C)C] | calcd C32H66N 464.5190, found 464.5199. |
| 41 | 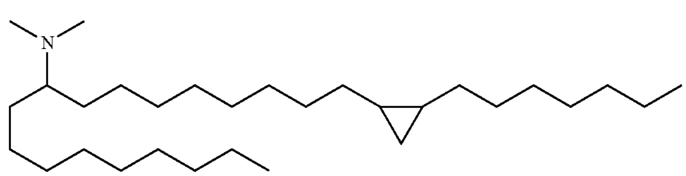 [SMILES: CCCCCCCCCC(CCCCCCCCC1CC1CCCCCCC)N(C)C] | calcd C30H62N 436.4877, found 436.4877. |
| 42 | 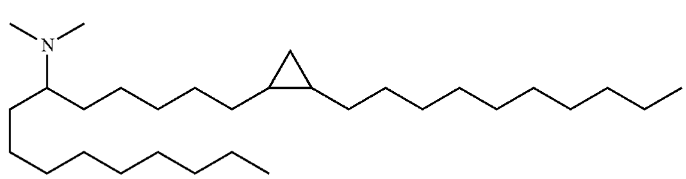 [SMILES: CCCCCCCCCCC1CC1CCCCCC(CCCCCCCCC)N(C)C] | calcd C30H62N 436.4877, found 436.4875. |
| 43 | 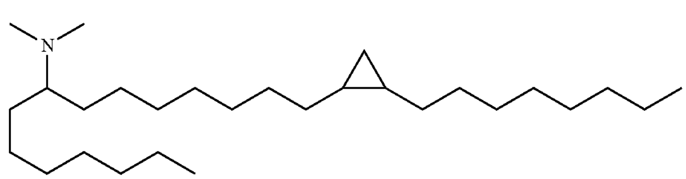 [SMILES: CCCCCCCCC1CC1CCCCCCCC(CCCCCCC)N(C)C] | LC/MS (M + H) 408.6. |

(11E,20Z,23Z)—N,N-dimethylnonacosa-11,20,23-trien-10-amine (Compound 44)

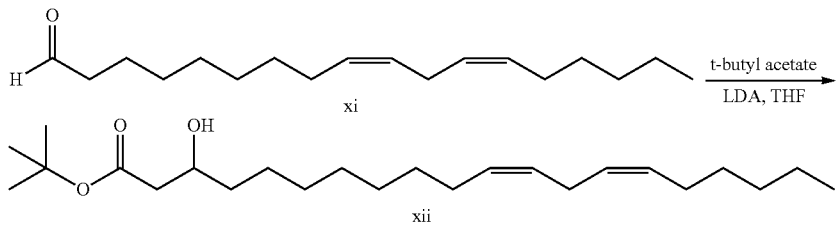

To a solution of LDA (95 mmol, 47.5 mL of a 2M solution) in THF (127 mL) cooled to −78° C. was added t-butyl acetate. The reaction was stirred for 15 minutes followed by addition of aldehyde xi. The reaction was immediately quenched with ammonium chloride solution, warmed to ambient temperature and partitioned between water/pentane. The organics were dried over sodium sulfate, filtered and evaporated in vacuo. LC/MS (M+H−tBu)= 325.4.

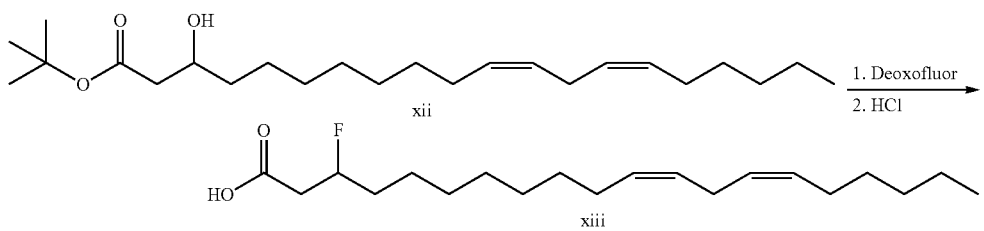

Hydroxy ketone xii (7 g, 18.4 mmol) was dissolved in dichloromethane (150 mL) and cooled to 0° C. and treated with deoxofluor (7.3 g, 33.1 mmol). The reaction was warmed to ambient temperature with stirring for 16 hours followed by quenching with sodium bicarbonate solution. The reaction was partitioned and the organics dried over sodium sulfide, filtered and evaporate in vacuo. Flash column chromotagraphy (0-5% ethyl acetate/hexanes) gave the β-fluoro ester.

Fluoro ester intermediate (6 g, 15.6 mmol) in dichloromethane was treated with hydrogen chloride (157 mmol, 39.2 mL of a 4M solution in dioxane) and the reaction was stirred at ambient temperature for 16 hours. The reaction was evaporated in vacuo to give desired β-fluoro acid xiii. LC/MS (M+H)=327.3.

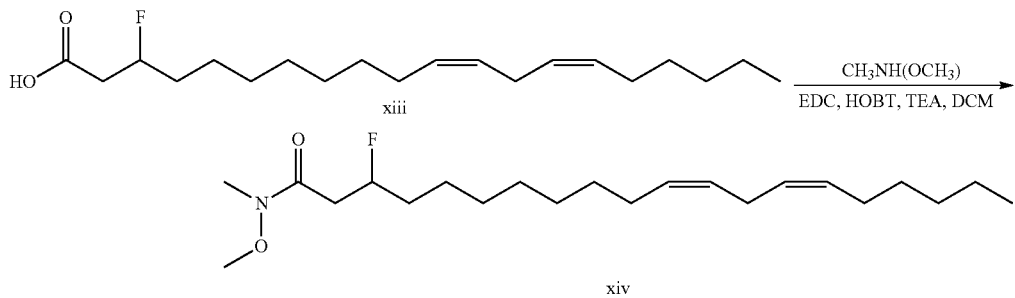

Fluoro carboxylic acid xiii (5.1 g, 15.7 mmol), EDC (6.0 g, 31.4 mmol), N,O-dimethylhydroxylamine hydrochloride (3.1 g, 31.4 mmol), trimethylamine (4.0 g, 39.2 mmol), and HOAt (4.3 g, 31.4 mmol) were combined in DCM (78 mL) and stirred at ambient temperature for 16 hours. The reaction was partitioned between water/DCM and the organics were washed with water (3×) and NaOH solution (1×), dried over sodium sulfate, filtered and evaporated in vacuo. Crude material was purified by reverse phase preparative chromatography to give desired Weinreb amide xiv. LC/MS (M+H)= 370.4.

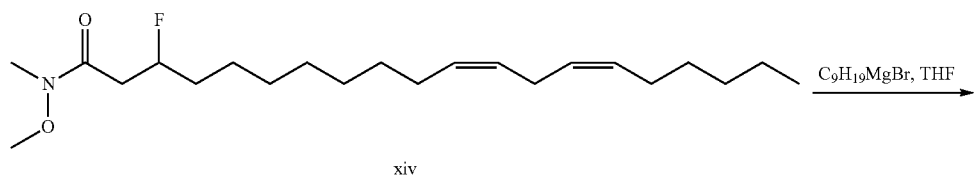

xiv

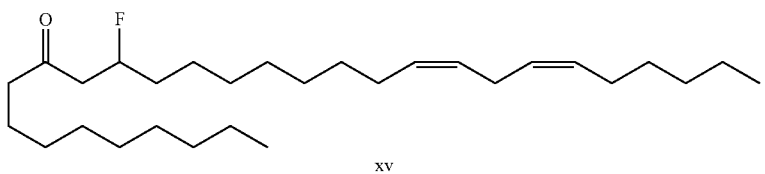

xv

A solution of Weinreb amide xiv (4.3 g, 11.7 mmol) in THF (50 mL) was treated with nonylmagnesium bromide (23.4 mmol, 23.4 mL of a 1M solution) at ambient temperature. The reaction was quenched with ammonium chloride solution after 1 hour and partitioned between water and pentane. The organics were dried over sodium sulfate, filtered and evaporated in vacuo. This material was carried into next step crude.

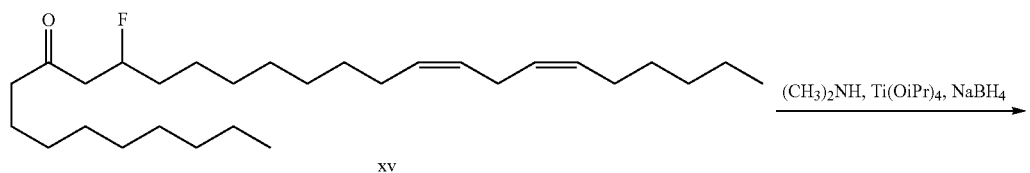

xv

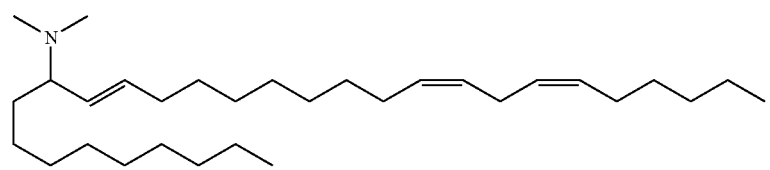

44

Ketone xv (5.1 g, 11.7 mmol) was treated with dimethylamine (29.3 mmol, 14.7 mL of a 2M solution in THF) and titanium(IV) isopropoxide (6.7 g, 23.5 mmol) and the reaction was stirred at ambient temperature for 16 hours. To the reaction mixture was added ethanol (50 mL) followed by sodium borohydride (0.67 g, 17.6 mmol). The reaction was loaded directly onto a silica column and purified by flash chromatography (0-15% MeOH/DCM). The material required a second purification by preparative reverse phase chromatography to give (11E,20Z,23Z)—N,N-dimethyl-nonacosa-11,20,23-trien-10-amine. HRMS calc'd 446.4720, found 446.4724. $^1$H NMR (400 MHz, CDCl$_3$) δ 5.48 (m, 1H), 5.37 (m, 4H), 5.23 (m, 1H), 2.78 (t, 2H), 2.58 (m, 1H), 2.22 (s, 6H), 2.04 (m, 6H), 1.56 (m, 1H), 1.30 (m, 31H), 0.89 (m, 6H).

Compound 45 is DLinKC2DMA as described in *Nature Biotechnology,* 2010, 28, 172-176, WO 2010/042877 A1, WO 2010/048536 A2, WO 2010/088537 A2, and WO2009/127060 A1.

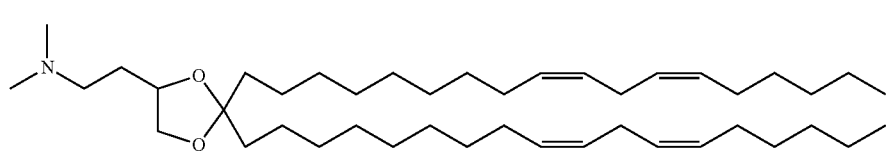

(45)

Compound 46 is MC3 as described in WO 2010/054401, and WO 2010/144740 A1.

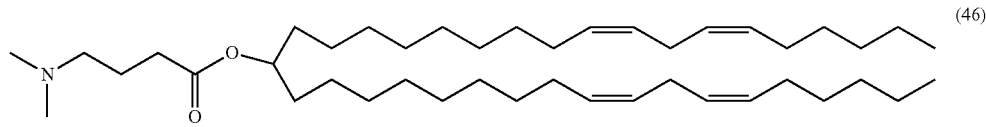 [SMILES: CCCCC/C=C\C/C=C\CCCCCCCCC(CCCCCCCC/C=C\C/C=C\CCCCC)OC(=O)CCCN(C)C]

(46)

LNP Compositions

The following lipid nanoparticle compositions (LNPs) of the instant invention are useful for the delivery of oligonucleotides, specifically siRNA and miRNA:
Cationic Lipid/Cholesterol/PEG-DMG 56.6/38/5.4;
Cationic Lipid/Cholesterol/PEG-DMG 60/38/2;
Cationic Lipid/Cholesterol/PEG-DMG 67.3/29/3.7;
Cationic Lipid/Cholesterol/PEG-DMG 49.3/47/3.7;
Cationic Lipid/Cholesterol/PEG-DMG 50.3/44.3/5.4;
Cationic Lipid/Cholesterol/PEG-C-DMA/DSPC 40/48/2/10;
Cationic Lipid/Cholesterol/PEG-DMG/DSPC 40/48/2/10; and
Cationic Lipid/Cholesterol/PEG-DMG/DSPC 58/30/2/10.

LNP Process Description:

The Lipid Nano-Particles (LNP) are prepared by an impinging jet process. The particles are formed by mixing lipids dissolved in alcohol with siRNA dissolved in a citrate buffer. The mixing ratio of lipids to siRNA are targeted at 45-55% lipid and 65-45% siRNA. The lipid solution contains a novel cationic lipid of the instant invention, a helper lipid (cholesterol), PEG (e.g. PEG-C-DMA, PEG-DMG) lipid, and DSPC at a concentration of 5-15 mg/mL with a target of 9-12 mg/mL in an alcohol (for example ethanol). The ratio of the lipids has a mole percent range of 25-98 for the cationic lipid with a target of 35-65, the helper lipid has a mole percent range from 0-75 with a target of 30-50, the PEG lipid has a mole percent range from 1-15 with a target of 1-6, and the DSPC has a mole percent range of 0-15 with a target of 0-12. The siRNA solution contains one or more siRNA sequences at a concentration range from 0.3 to 1.0 mg/mL with a target of 0.3-0.9 mg/mL in a sodium citrate buffered salt solution with pH in the range of 3.5-5. The two liquids are heated to a temperature in the range of 15-40° C., targeting 30-40° C., and then mixed in an impinging jet mixer instantly forming the LNP. The teeID has a range from 0.25 to 1.0 mm and a total flow rate from 10-600 mL/min. The combination of flow rate and tubing ID has effect of controlling the particle size of the LNPs between 30 and 200 nm. The solution is then mixed with a buffered solution at a higher pH with a mixing ratio in the range of 1:1 to 1:3 vol:vol but targeting 1:2 vol:vol. This buffered solution is at a temperature in the range of 15-40° C., targeting 30-40° C. The mixed LNPs are held from 30 minutes to 2 hrs prior to an anion exchange filtration step. The temperature during incubating is in the range of 15-40° C., targeting 30-40° C. After incubating the solution is filtered through a 0.8 um filter containing an anion exchange separation step. This process uses tubing IDs ranging from 1 mm ID to 5 mm ID and a flow rate from 10 to 2000 mL/min. The LNPs are concentrated and diafiltered via an ultrafiltration process where the alcohol is removed and the citrate buffer is exchanged for the final buffer solution such as phosphate buffered saline. The ultrafiltration process uses a tangential flow filtration format (TFF). This process uses a membrane nominal molecular weight cutoff range from 30-500 KD. The membrane format can be hollow fiber or flat sheet cassette. The TFF processes with the proper molecular weight cutoff retains the LNP in the retentate and the filtrate or permeate contains the alcohol; citrate buffer; final buffer wastes. The TFF process is a multiple step process with an initial concentration to a siRNA concentration of 1-3 mg/mL. Following concentration, the LNPs solution is diafiltered against the final buffer for 10-20 volumes to remove the alcohol and perform buffer exchange. The material is then concentrated an additional 1-3 fold. The final steps of the LNP process are to sterile filter the concentrated LNP solution and vial the product.

Analytical Procedure:

1) siRNA Concentration

The siRNA duplex concentrations are determined by Strong Anion-Exchange High-Performance Liquid Chromatography (SAX-HPLC) using Waters 2695 Alliance system (Water Corporation, Milford Mass.) with a 2996 PDA detector. The LNPs, otherwise referred to as RNAi Delivery Vehicles (RDVs), are treated with 0.5% Triton X-100 to free total siRNA and analyzed by SAX separation using a Dionex BioLC DNAPac PA 200 (4*250 mm) column with UV detection at 254 nm. Mobile phase is composed of A: 25 mM $NaClO_4$, 10 mM Tris, 20% EtOH, pH 7.0 and B: 250 mM $NaClO_4$, 10 mM Tris, 20% EtOH, pH 7.0 with liner gradient from 0-15 min and flow rate of 1 ml/min. The siRNA amount is determined by comparing to the siRNA standard curve.

2) Encapsulation Rate

Fluorescence reagent SYBR Gold is employed for RNA quantitation to monitor the encapsulation rate of RDVs. RDVs with or without Triton X-100 are used to determine the free siRNA and total siRNA amount The assay is performed using a SpectraMax M5e microplate spectrophotometer from Molecular Devices (Sunnyvale, Calif.). Samples are excited at 485 nm and fluorescence emission was measured at 530 nm. The siRNA amount is determined by comparing to the siRNA standard curve.

Encapsulation rate=(1−free siRNA/total siRNA)×100%

3) Particle Size and Polydispersity

RDVs containing 1 μg siRNA are diluted to a final volume of 3 ml with 1× PBS. The particle size and polydispersity of the samples is measured by a dynamic light scattering method using ZetaPALS instrument (Brookhaven Instruments Corporation, Holtsville, N.Y.). The scattered intensity is measured with He—Ne laser at 25° C. with a scattering angle of 90°.

4) Zeta Potential Analysis

RDVs containing 1 μg siRNA are diluted to a final volume of 2 ml with 1 mM Tris buffer (pH 7.4). Electrophoretic mobility of samples is determined using ZetaPALS instrument (Brookhaven Instruments Corporation, Holtsville, N.Y.) with electrode and He—Ne laser as a light source. The Smoluchowski limit is assumed in the calculation of zeta potentials.

5) Lipid Analysis

Individual lipid concentrations are determined by Reverse Phase High-Performance Liquid Chromatography (RP-HPLC) using Waters 2695 Alliance system (Water Corporation, Milford, Mass.) with a Corona charged aerosol detector (CAD) (ESA Biosciences, Inc, Chelmsford, Mass.). Individual lipids in RDVs are analyzed using an Agilent Zorbax SB-C18 (50×4.6 mm, 1.8 μm particle size) column with CAD at 60° C. The mobile phase is composed of A: 0.1% TFA in $H_2O$ and B: 0.1% TFA in IPA. The gradient changes from 60% mobile phase A and 40% mobile phase B from time 0 to 40% mobile phase A and 60% mobile phase B at 1.00 min; 40% mobile phase A and 60% mobile phase B from 1.00 to 5.00 min; 40% mobile phase A and 60% mobile phase B from 5.00 min to 25% mobile phase A and 75% mobile phase B at 10.00 min; 25% mobile phase A and 75% mobile phase B from 10.00 min to 5% mobile phase A and 95% mobile phase B at 15.00 min; and 5% mobile phase A and 95% mobile phase B from 15.00 to 60% mobile phase A and 40% mobile phase B at 20.00 min with flow rate of 1 ml/min. The individual lipid concentration is determined by comparing to the standard curve with all the lipid components in the RDVs with a quadratic curve fit. The molar percentage of each lipid is calculated based on its molecular weight.

General LNP Process Description for Compound 32 Formulations:

The lipid nanoparticles were prepared by an impinging jet process. The particles were formed by mixing lipids dissolved in alcohol with siRNA dissolved in a citrate buffer. The lipid solution contained a cationic lipid, a helper lipid (cholesterol), PEG (e.g. PEG-C-DMA, PEG-DMG) lipid, and DSPC at a concentration of 5-15 mg/mL with a target of 9-12 mg/mL in an alcohol (for example ethanol). The ratio of the lipids had a mole percent range of 25-98 for the cationic lipid with a target of 35-65, the helper lipid had a mole percent range from 0-75 with a target of 30-50, the PEG lipid has a mole percent range from 1-15 with a target of 1-6, and the DSPC had a mole percent range of 0-15 with a target of 0-12. The siRNA solution contained one or more siRNA sequences at a concentration range from 0.3 to 0.6 mg/mL with a target of 0.3-0.9 mg/mL, in a sodium citrate buffered salt solution with pH in the range of 3.5-5. The two solutions were heated to a temperature in the range of 15-40° C., targeting 30-40° C. and then mixed in an impinging jet mixer instantly forming the LNP. The teeID had a range from 0.25 to 1.0 mm and a total flow rate from 10-600 mL/minute. The combination of flow rate and tubing ID had the effect of controlling the particle size of the LNPs between 30 and 200 nm. The LNP suspension was then mixed with a buffered solution at a higher pH with a mixing ratio in the range of 1:1 to 1:3 vol:vol, but targeting 1:2 vol:vol. This buffered solution was at a temperature in the range of 15-40° C., targeting 30-40° C. This LNP suspension was further mixed with a buffered solution at a higher pH and with a mixing ratio in the range of 1:1 to 1:3 vol:vol, but targeting 1:2 vol:vol. The buffered solution was at a temperature in the range of 15-40° C., targeting 30-40° C. The mixed LNPs were held from 30 minutes to 2 hrs prior to an anion exchange filtration step. The temperature during incubating was in the range of 15-40° C., targeting 30-40° C. After incubating, the LNP suspension was filtered through a 0.8 um filter containing an anion exchange separation step. This process used tubing IDs ranging from 1 mm ID to 5 mm ID and a flow rate from 10 to 2000 mL/minute The LNPs were concentrated and diafiltered via an ultrafiltration process where the alcohol was removed and the citrate buffer was exchanged for the final buffer solution such as phosphate buffered saline. The ultrafiltration process used a tangential flow filtration format (TFF). This process used a membrane nominal molecular weight cutoff range from 30-500 KD. The membrane format was hollow fiber or flat sheet cassette. The TFF processes with the proper molecular weight cutoff retained the LNP in the retentate and the filtrate or permeate contained the alcohol; citrate buffer; and final buffer wastes. The TFF process is a multiple step process with an initial concentration to a siRNA concentration of 1-3 mg/mL. Following concentration, the LNP suspension was diafiltered against the final buffer for 10-20 volumes to remove the alcohol and perform buffer exchange. The material was then concentrated an additional 1-3 fold. The final steps of the LNP process were to sterile filter the concentrated LNP solution and vial the product.

Analytical Procedure:

siRNA Concentration

The siRNA duplex concentrations were determined by Strong Anion-Exchange High-Performance Liquid Chromatography (SAX-HPLC) using Waters 2695 Alliance system (Water Corporation, Milford Mass.) with a 2996 PDA detector. The LNPs, otherwise referred to as RNAi Delivery Vehicles (RDVs), were treated with 0.5% Triton X-100 to free total siRNA and analyzed by SAX separation using a Dionex BioLC DNAPac PA 200 (4*250 mm) column with UV detection at 254 nm. Mobile phase was composed of A: 25 mM $NaClO_4$, 10 mM Tris, 20% EtOH, pH 7.0 and B: 250 mM $NaClO_4$, 10 mM Tris, 20% EtOH, pH 7.0 with a liner gradient from 0-15 min and a flow rate of 1 ml/minute. The siRNA amount was determined by comparing to the siRNA standard curve.

Encapsulation Rate

Fluorescence reagent SYBR Gold was employed for RNA quantitation to monitor the encapsulation rate of RDVs. RDVs with or without Triton X-100 were used to determine the free siRNA and total siRNA amount. The assay is performed using a SpectraMax M5e microplate spectrophotometer from Molecular Devices (Sunnyvale, Calif.). Samples were excited at 485 nm and fluorescence emission was measured at 530 nm. The siRNA amount is determined by comparing to an siNA standard curve.

Encapsulation rate=(1−free siNA/total siNA)×100%

Particle Size and Polydispersity

RDVs containing 1 μg siRNA were diluted to a final volume of 3 ml with 1× PBS. The particle size and polydispersity of the samples was measured by a dynamic light scattering method using ZetaPALS instrument (Brookhaven Instruments Corporation, Holtsville, N.Y.). The scattered intensity was measured with He—Ne laser at 25° C. with a scattering angle of 90°.

Zeta Potential Analysis

RDVs containing 1 μg siRNA were diluted to a final volume of 2 ml with 1 mM Tris buffer (pH 7.4). Electrophoretic mobility of samples was determined using ZetaPALS instrument (Brookhaven Instruments Corporation, Holtsville, N.Y.) with electrode and He—Ne laser as a light source. The Smoluchowski limit was assumed in the calculation of zeta potentials.

Lipid Analysis

Individual lipid concentrations were determined by Reverse Phase High-Performance Liquid Chromatography (RP-HPLC) using Waters 2695 Alliance system (Water Corporation, Milford Mass.) with a Corona charged aerosol detector (CAD) (ESA Biosciences, Inc, Chelmsford, Mass.). Individual lipids in RDVs were analyzed using an Agilent Zorbax SB-C18 (50×4.6 mm, 1.8 μm particle size) column with CAD at 60° C. The mobile phase was composed of A: 0.1% TFA in $H_2O$ and B: 0.1% TFA in IPA. The gradient changed from 60% mobile phase A and 40% mobile phase B from time 0 to 40% mobile phase A and 60% mobile phase B at 1.00 min; 40% mobile phase A and 60% mobile phase B from 1.00 to 5.00 min; 40% mobile phase A and 60% mobile phase B from 5.00 min to 25% mobile phase A and 75% mobile phase B at 10.00 min; 25% mobile phase A and 75% mobile phase B from 10.00 min to 5% mobile phase A and 95% mobile phase B at 15.00 min; and 5% mobile phase A and 95% mobile phase B from 15.00 to 60% mobile phase A and 40% mobile phase B at 20.00 min with a flow rale of 1 ml/minute. The individual lipid concentration was determined by comparing to the standard curve with all the lipid components in the RDVs with a quadratic curve fit. The molar percentage of each lipid was calculated based on its molecular weight.

General LNP Preparation for Various Formulations in Table 1.

siRNA nanoparticle suspensions in Table 1 are prepared by dissolving siRNAs and/or carrier molecules in 20 mM sodium citrate buffer (pH 5.0) at a concentration of about 0.40 mg/mL. Lipid solutions are prepared by dissolving a mixture of cationic lipid (e.g., 32, see structure in Table 2), DSPC, Cholesterol, and PEG-DMG (ratios shown in Table 1) in absolute ethanol at a concentration of about 8 mg/mL. The nitrogen to phosphate ratio is approximate to 6:1.

Nearly equal volumes of siRNA/carrier and lipid solutions are delivered with two FPLC pumps at the same flow rates to a mixing T connector. A back pressure valve is used to adjust to the desired particle size. The resulting milky mixture is collected in a sterile glass bottle. This mixture is then diluted with an equal volume of citrate buffer, followed by equal volume of PBS (pH 7.4), and filtered through an ion-exchange membrane to remove any free siRNA/carrier in the mixture. Ultra filtration against PBS (7.4)) is employed to remove ethanol and to exchange buffer. The final LNP is obtained by concentrating to a desired volume and sterile filtered through a 0.2 μm filter. The obtained LNPs are characterized in term of particle size, Zeta potential, alcohol content, total lipid content, nucleic acid encapsulated, and total nucleic acid concentration.

LNP Manufacture Process

In a non-limiting example, LNP is prepared in bulk as follows. The process consists of (1) preparing a lipid solution; (2) preparing an siRNA/carrier solution; (3) mixing/particle formation; (4) incubation; (5) dilution; (6) ultrafiltration and concentration.

Preparation of Lipid Solution

2 L glass reagent bottles and measuring cylinders are depyrogenated. The lipids are warmed to room temperature. Into the glass reagent bottle is transferred 8.0 g of Compound 32 with a pipette and 1.2 g of DSPC, 3.5 g of Cholesterol, 0.9 g of PEG-DMG are added. To the mixture is added 1 L of ethanol. The reagent bottle is placed in heated water bath, at a temperature not exceeding 50° C. The lipid suspension is stirred with u stir bar. A thermocouple probe is put into the suspension through one neck of the round bottom flask with a sealed adapter. The suspension is heated at 30-40° C. until it became clear. The solution is allowed to cool to room temperature.

Preparation of siRNA/Carrier Solution

Into a sterile container, such as the Corning storage bottle, is weighed 0.4 g times the water correction factor (approximately 1.2) of siRNA-1 powder. The siRNA is transferred to a depyrogenated 2 L glass reagent bottle. The weighing container is rinsed 3× with citrate buffer (20 mM, pH 5.0) and the rinses are placed into the 2 L glass bottle, QS with citrate buffer to 1 L. The concentration of the siRNA solution is determined with a UV spectrometer using the following procedure. 20 μL is removed from the solution, diluted 50 times to 1000 μL, and the UV reading recorded at A260 nm after blanking with citrate buffer. This is repeated. If the readings for the two samples are consistent, an average is taken and the concentration is calculated based on the extinction coefficients of the siRNAs. If the final concentration is out of the range of 0.40±0.01 mg/mL, the concentration is adjusted by adding more siRNA/carrier powder, or adding more citrate buffer. This process is repeated for the second siRNA, if applicable.

Alternatively, if the siRNA/carrier solution comprised a single siRNA duplex and/or carrier instead of a cocktail of two or more siRNA duplexes and/or carriers, then the siRNA/carrier is dissolved in 20 mM citrate buffer (pH 5.0) to give a final concentration of 0.4 mg/mL.

The lipid and ethanol solutions are then sterile filtered through a Pall Acropak 20 0.8/0.2 µm sterile filter PN 12203 into a depyrogenated glass vessel using a Master Flex Peristaltic Pump Model 7520-40 to provide a sterile starting material for the encapsulation process. The filtration process is run at an 80 mL scale with a membrane area of 20 cm$^2$. The flow rate is 280 mL/minute. This process is scaleable by increasing the tubing diameter and the filtration area.

Particle Formation—Mixing Step

Using a two-barrel syringe driven pump (Harvard 33 Twin Syringe), the sterile lipid/ethanol solution and the sterile siRNA/carrier or siRNA/carrier cocktail/citrate buffer (20 mM citrate buffer, pH 5.0) solutions are mixed in a 0.5 mm ID T-mixer (Mixing Stage I) at equal, or nearly equal, flow rates. The resulting outlet LNP suspension is contained 40-50 vol % ethanol. When a 45 vol % ethanol outlet suspension is desired, the sterile lipid/ethanol and the sterile siRNA/carrier or siRNA/carrier cocktail/citrate buffer solutions are mixed at flow rates of 54 mL/min and 66 mL/min, respectively, such that the total flow rate of the mixing outlet is 120 mL/min.

Dilution

The outlet stream of Mixing Stage I is fed directly into a 4 mm ID T-mixer (Mixing Stage II), where it is diluted with a buffered solution at higher pH (20 mM sodium citrate, 300 mM sodium chloride, pH 6.0) at a ratio of 1:1 vol:vol %. This buffered solution is at a temperature in the range of 30-40° C., and is delivered to the 4 mm T-mixer via a peristaltic pump (Cole Parmer MusterFlex L/S 600 RPM) at a flow rate of 120 mL/min.

The outlet stream of Mixing Stage II is fed directly into a 6 mm ID T-mixer (Mixing Stage III), where it is diluted with a buffered solution at higher pH (PBS, pH 7.4) at a ratio of 1:1 vol:vol %. This buffered solution is at a temperature in the range of 15-25° C., and is delivered to the 6 mm T-mixer via peristaltic pump (Cole Parmer MasterFlex L/S 600 RPM) at a flow rate of 240 mL/min.

Incubation and Free siRNA Removal

The outlet stream of Mixing Stage III is held after mixing for 30 minute incubation. The incubation is conducted at temperature of 35-40° C. and the in-process suspension was protected from light. Following incubation, free (un-encapsulated) siRNA is removed via anion exchange with Mustang Q chromatography filters (capsules). Prior to use, the chromatography filters are pre-treated sequentially with flushes of 1N NaOH, 1M NaCl, and a final solution of 12.5 vol % ethanol in PBS. The pH of the final flush is checked to ensure pH<8. The incubated LNP stream is then filtered via Mustang Q filters via peristaltic pump (Cole Parmer MasterFlex L/S 600 RPM) at flow rate of approximately 100 mL/min. The filtered stream is received into a sterile glass container for ultrafiltration and concentration as follows.

Ultrafiltration, Concentration and Sterile Filtration

The ultrafiltration process is a timed process and the flow rates must be monitored carefully. This is a two step process; the first is a concentration step taking the diluted material and concentrating approximately 8-fold, to a concentration of approximately 0.3-0.6 mg/mL siRNA.

In the first step, a ring-stand with an ultrafiltration membrane 100 kDa PES (Spectrum Labs) installed is attached to a peristaltic pump (Spectrum KrosFloII System). 9.2 L of sterile distilled water is added to the reservoir; 3 L is drained to waste and the remainder is drained through permeate to waste. 5.3 L of 0.25 N sodium hydroxide is added to the reservoir with 1.5 L drained to waste and 3.1 L drained through permeate to waste. The remaining sodium hydroxide is held in the system for sanitization (at least 10 minutes), and then the pump is drained. 9.2 L of 70 (v/v) % isopropyl alcohol is added to the reservoir with 1.5 L drained to waste and the remainder drained through permeate to waste. 6 L of conditioning buffer (12.5% ethanol in phosphate buffered saline) is added with 1.5 L drained to waste and the remainder drained though the permeate until the waste is of neutral pH (7-8). A membrane flux value is recorded, and the pump is then drained.

The diluted LNP solution is placed into the reservoir to the 1.1 L mark. The pump is turned on at 2.3 L/min. After 5 minutes of recirculation, the permeate pump is turned on at 62.5 mL/min and the liquid level is constant at approximately 950 mL in the reservoir. The diluted LNP solution is concentrated from 9.8 L to 1.1 L in 140 minutes, and the pump is paused when all the diluted LNP solution has been transferred to the reservoir.

The second step is a diafiltration step exchanging the ethanol/aqueous buffer to phosphate buffered saline. During this step, approximately 10-20 diafiltration volumes of phosphate buffered saline are used. Following diafiltration, a second concentration is undertaken to concentrate the LNP suspension 3-fold to approximately 1-1.5 mg/mL siRNA. The concentrated suspension is collected into sterile, plastic PETG bottles. The final suspension is then filtered sequentially via Pall 0.45 um PES and Pall 0.2 um PES filters for terminal sterilization prior to vial filling.

In an embodiment, an LNP composition of the instant invention comprises, a cationic lipid of Formula A, cholesterol, DSPC and PEG-DMG.

In another embodiment, an LNP composition of the instant invention further comprises a cryoprotectant.

In another embodiment, the cryoprotectant is Sucrose, Trehalose, Raffinose, Stachyose, Verbascose, Mannitol, Glucose, Lactose, Maltose, Maltotriose-heptaose, Dextran, Hydroxyethyl Starch, Insulin, Sorbitol, Glycerol, Arginine, Histidine, Lysine, Proline, Dimethylsulfoxide or any combination thereof.

In another embodiment, the cryoprotectant is Sucrose.

In another embodiment, the cryoprotectant is Trehalose.

In another embodiment, the cryoprotectant is a combination of Sucrose and Trehalose.

In another embodiment, the LNP composition comprises, the cationic lipid (13Z,16Z)—N,N-dimethyl-3-nonyldocosa-13,16-dien-1-amine (Compound 32), cholesterol, DSPC and PEG-DMG.

The obtained LNPs are characterized in terms of particle size, Zeta potential, alcohol content, total lipid content, nucleic acid encapsulated, and total nucleic acid concentration.

One skilled in the art would readily appreciate that the present invention is well adapted to carry out the objects and obtain the ends and advantages mentioned, as well as those inherent therein. The methods and compositions described herein, as presently representative of preferred embodiments, are exemplary and are not intended as limitations on the scope of the invention. (Changes therein and other uses will occur to those skilled in the art, which are encompassed within the spirit of the invention, ore defined by the scope of the claims.

TABLE 1

Composition of Select Lipid Nanoparticle Formulations
LNP Identifier

| Lipid Components and Molar Ratios | | | | siRNA | N/P |
|---|---|---|---|---|---|
| 32 (58%) | Cholesterol (30%) | DSPC (10%) | PEG-DMG (2%) | SEQ ID 5/6 | 6 |
| 32 (58%) | Cholesterol (30%) | DSPC (10%) | PEG-DMG (2%) | SEQ ID 7/8 | 6 |
| 32 (58%) | Cholesterol (30%) | DSPC (10%) | PEG-DMG (2%) | SEQ ID 9/10 | 6 |

TABLE 2

Chemical Structures of Lipids in Formulations of Table 1.

| Lipid | Chemical Structure |
|---|---|
| 32 | *(structure shown)* |
| Cholesterol | *(structure shown)* |
| DSPC | *(structure shown)* |
| PEO-DMG | *(structure shown)* |

Utilizing the above described LNP process, specific LNPs with the following ratios were identified:

Nominal Composition:
Cationic Lipid/Cholesterol/PEG-DMG 60/38/2
Cationic Lipid/Cholesterol/PEG-DMG/DSPC 58/30/2/10
Luc siRNA (SEQ. ID. NO: 1)
5'-iB-AUAAGGCUAUGAAGAGAUAUU-iB 3'

(SEQ ID NO.: 2)
3'-UUUAUUCCGAUACUUCUCUAU-5'

AUGC—Ribose
iB—Inverted deoxy abasic
UC—2' Fluoro
AGT—2' Deoxy
AGU—2' OCH$_3$

Nominal Composition
Cationic Lipid/Cholesterol/PEG-DMG 60/38/2
Cationic Lipid/Cholesterol/PEG-DMG/DSPC 40/48/2/10
Cationic Lipid/Cholesterol/PEG-DMG/DSPC 58/30/2/10
ApoB siRNA (SEQ ID NO.: 3)
    5'-iB-CUUUAACAAUUCCUGAAAUTsT-iB-3'

(SEQ ID NO.: 4)
    3'-UsUGAAAUUGUUAAGGACUsUsUsA-5'

AUGC—Ribose
iB—Inverted deoxy abasic
UC—2' Fluoro
AGT—2' Deoxy
AGU—2' OCH₃
UsA—phophorothioate linkage
beta-caterin siRNA (SEQ ID NO.: 5)
    5'-iB-CUGUUGGAUUGAUUCGAAAUsU-iB-3'

(SEQ ID NO.: 6)
    3'-UsUGACAACCUAACUAAGCUUU-5'

AUGC—Ribose
iB—Inverted deoxy abasic
UC—2' Fluoro
AGT—2' Deoxy
AGU—2' OCH₃
UsA—phophorothioate linkage (SEQ ID NO.: 7)
    5'-iB-ACGACUAGUUCAGUUGCUUUsU-iB-3'

(SEQ ID NO.: 8)
    3'-UsUUGCUGAUCAAGUCAACGAA-5'

AUGC—Ribose
iB—Inverted deoxy abasic
UC—2' Fluoro
ACT—2' Deoxy
AGU—2' OCH₃
UsA—phophorothioate linkage (SEQ ID NO.: 9)
    5'-iB-ACGACUAGUUCAGUUGCUUUU-iB-3'

(SEQ ID NO.: 10)
    3'-UUUGCUGAUCAAGUCAACGAA-5'

AUGC—Ribose
iB—Inverted deoxy abasic
UC—2' Fluoro
AGT—2' Deoxy
AGU—2' OCH₃
UsA—phophorothioate linkage Oligonucleotide synthesis is well known in the art. (See US patent applications: US 2006/0083780, US 2006/0240554, US 2008/0020058, US 2009/0263407 and US 2009/0285881 and PCT patent applications: WO 2009/086558, WO2009/127060, WO2009/132131, WO2010/042877, WO2010/054384, WO2010/054401, WO2010/054405 and WO2010/054406). The siRNAs disclosed and utilized in the Examples were synthesized via standard solid phase procedures.

Example 1

Mouse In Vivo Evaluation of Efficacy

Figure 11:
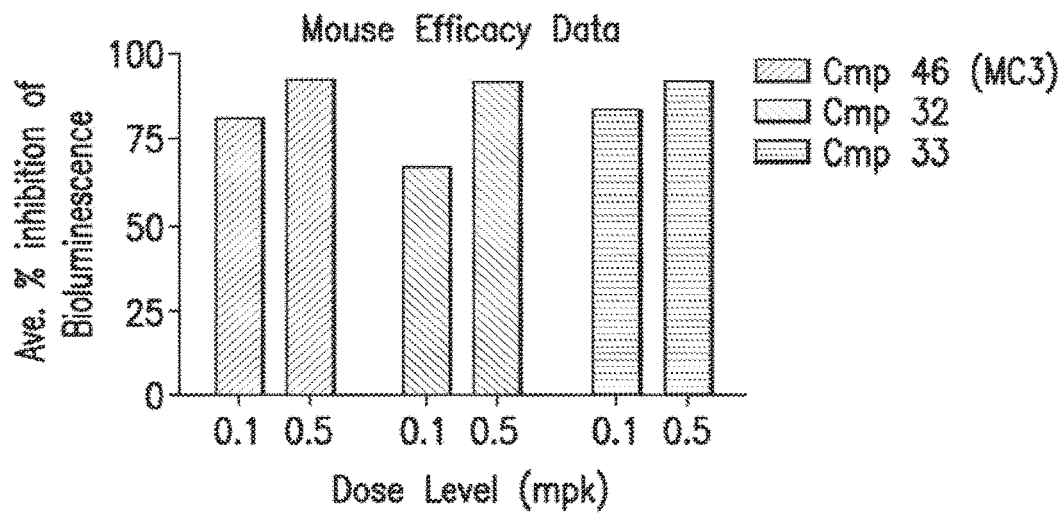
FIG. 11. LNP (Compounds 32 and 33) efficacy in mice.

LNPs utilizing Compounds 1-44, in the nominal compositions described immediately above, were evaluated for in vivo efficacy. The siRNA targets the mRNA transcript for the firefly (*Photinus pyralis*) luciferase gene (Accession #M15077). The primary sequence and chemical modification pattern of the luciferase siRNA is displayed above. The in vivo luciferase model employs a transgenic mouse in which the firefly luciferase coding sequence is present in all cells. ROSA26-LoxP-Stop-LoxP-Luc (LSL-Luc) transgenic mice licensed from the Dana Farber Cancer Institute are induced to express the Luciferase gene by first removing the LSL sequence with a recombinant Ad-Cre virus (Vector Biolabs). Due to the organo-tropic nature of the virus, expression is limited to the liver when delivered via tail vein injection. Luciferase expression levels in liver are quantitated by measuring light output, using an IVIS imager (Xenogen) following administration of the luciferin substrate (Caliper Life Sciences). Pre-dose luminescence levels are measured prior to administration of the RDVs. Luciferin in PBS (15 mg/mL) is intraperitoneally (IP) injected in a volume of 150 µL. After a four minute incubation period mice are anesthetized with isoflurane and placed in the IVIS imager. The RDVs (containing siRNA) in PBS vehicle were tail vein injected in a volume of 0.2 mL. Final dose levels ranged from 0.1 to 0.5 mg/kg siRNA. PBS vehicle alone was dosed as a control. Mice were imaged 48 hours post dose using the method described above. Changes in luciferin light output directly correlate with luciferase mRNA levels and represent an indirect measure of luciferase siRNA activity. In vivo efficacy results are expressed as % inhibition of luminescence relative to pre-dose luminescence levels. Systemic administration of the luciferase siRNA RDVs decreased luciferase expression in a dose dependant manner. Greater efficacy was observed in mice dosed with Compound 1 containing RDVs than with the RDV containing the octyl-CLinDMA (OCD) cationic lipid (FIG. 1). OCD is known and described in WO2010/021865. Similar efficacy was observed in mice dosed with Compound 32 and 33 containing RDVs relative to the RDV containing the MC3 (Compound 46) cationic lipid (FIG. 11).

Example 2

In vitro ApoE Binding Assay

LNPs are incubated at 37° C. in 90% rhesus serum at a final LNP concentration of 4 ug/mL. Incubation is for 20 minutes with orbital rotation. After incubation, the samples are diluted 1:20 in PBS and 100 uL of each diluted sample is aliquoted to wells of an anti-PEG antibody coated 96-well plate (Life Diagnostics Cat. No. P-0001PL. After incubation at room temperature for 1 hour, the plate is washed 5× with 300 uL PBS. After washing, 50 uL of 0.2% Triton X-100 is added to each well and the plate incubated at 37° C. for 10 minutes, followed by shaking on a plate shaker for 1 minute at 750 rpm. Samples are frozen prior to performing the ApoE ELISA and stem loop PCR analysis of samples.

An ApoE ELISA assay is performed to quantitate ApoE bound to the LNPs after incubation in rhesus serum. Anti-ApoE antibody (Milipore, Cat No. AB947) is diluted 1:1000 in PBS and 100 uL of diluted antibody is added to each well of a polystyrene high binding plate. The plate with antibody is incubated overnight at 4° C., after which the plate is washed 2× with 200 uL of PBS. Next, 200 uL of buffer containing 1% BSA and 0.05% Tween-20 in PBS (Incubation Buffer) is added to each well followed by incubation at room temperature for 1 hour. Plates are washed 5× with PBS containing 0.05% Tween-20. Frozen Triton lysis test samples are thawed and diluted 1:6 with incubation buffer and 100 uL of test sample is aliquoted to wells of the ApoE antibody plate. Incubation is for 1 hour at room temperature followed by a 5× wash with PBS containing 0.05% Tween-20. After washing, 100 uL of biotinylated anti-ApoE antibody (Mabtech, Cat. ANo. E887-biotin), diluted 1:500 in incubation buffer, is added to each well and incubated for 1 hour at room temperature, followed by a 5× wash with 0.05% Tween-20 in PBS. 100 uL per well, of Streptavidin-HPR (Thermo, Cat. No. TS-125-HR), is then added and incubated for 1 hour at room temperature. After washing 5× with 0.05% Tween-20 in PBS, 100 uL of TMB Substrate (Thermo, Cat. No. 34028) is added to each well, followed by incubation at room temperature for 20 minutes in the dark. The calorimetric reaction is slopped with 100 uL of TMB Stop Solution (KPL, Cat. No. 50-85-04) and absorbance at 450 nm is determined. An ApoE standard curve is prepared by diluting rhesus Recombinant ApoE in incubation buffer with 0.03% Triton X-100 with concentrations ranging from 100 ng/mL to 0.78 ng/mL. ApoE standards are evaluated in the ELISA in parallel to the test samples. A rhesus serum only (no LNP) control is utilized to obtain a background subtraction for non-LNP dependent ApoE signal in the ELISA.

Stem Loop RT-PCR Protcol

To normalize to the ApoE bound to the amount of LNP bound to the anti-PEG antibody plate, the amount of siRNA retained in the anti-PEG antibody well is quantitated by stem-loop PCR and related to the number of siRNAs encapsulated per LNP, to give an approximate measure of total LNP particles bound per well.

Preparation of the Spiked Standard Curve Samples:

The standard curve is prepared using the molecular weight of the siRNA (13693 g/mol for ApoB 17063) to calculate the copy number. The high standard should contain $10^{11}$ copies per 3 µl. A 10-fold serial dilution is performed across a row of an assay plate until the lowest standard contains $10^2$ copies per 3 µl. Dilute 0.2% Triton X-100 1:80 in water and pipette 20 uL of the diluted Triton X-100 into 10 wells of a 96 well plate. 30 uL of the serial diluted standard curve and mix are added to each well of the plate. 10 uL of the spiked standard curve is used in the reverse transcription reaction.

Stem Loop RT-PCR—Test Samples and Standard Curve:

Triton lysates from the PEG antibody plate capture are diluted 1 to 2000 in nuclease free water. 10 uL of 'RT-Primer Mix' (Applied Biosystem's TaqMan MicroRNA Reverse Transcription Kit Cat. No. 4366596) is added to each well of a 96-well Micro-Amp QPCR plate (ABI Cat #N801-0560).

| RT Primer Mix Components | uL/rxn | Final conc. |
|---|---|---|
| ApoB RT-primer (10 uM) | 0.6 | 200 nM |
| 10× buffer | 2 | |
| Water | 7.4 | |

ApoB RT primer sequence:
(SEQ. ID. NO.: 11)
5' GTCGTATCCAGTGCAGGGTCCGAGGTATTCGCACTGGATACGACCT
TTAACA3'

10 mL of each test sample (diluted 1 to 2000) or spiked standard curve (above) are aliquoted into the 96-well plate. The plate is covered with a mat (ABI Cat. No. N801-0550), to minimize evaporation. The plate is briefly centrifuged at 800 rpm for 1 minute. Next, the plate is run on a thermocycler using the following cycling parameters:

| Cycling: | 94° C. | 10 minutes |
|---|---|---|
| | 75° C. | 2 minutes |
| | 60° C. | 3 minutes |
| | 50° C. | 3 minutes |
| | 40° C. | 3 minutes |
| | 30° C. | 3 minutes |
| | 4° C. | hold |

Next, 10 uL of 'RT Mix' is added to each well (Applied Biosystem's TaqMan MicroRNA Reverse Transcription Kit Cat. No. 4366596)

| RT Primer Mix Compppents | uL/rxn |
|---|---|
| 100 mM dNTP | 0.3 |
| 10× RT buffer | 1 |
| Rnase Inhibitor | 0.38 |
| Multiscribe RT enzyme | 1 |
| Water | 7.32 |

The RT cycling reaction is composed of 10 uL test sample, 10 uL of RT primer mix and 10 uL of RT Mix components for a total volume of 30 uL. The final concentration of the RT-primer in the total 30 uL total RT mix is 200 nM. The plate is then sealed with the same plate mat, briefly centrifuged at 800 rpm for 1 minute, then run on the thermocycler using the following cycling parameters:

| Cycling: | 16° C. | 30 minutes |
|---|---|---|
| | 42° C. | 30 minutes |
| | 85° C. | 5 minutes |
| | 4° C. | hold |

Next, 15 uL of Fast Enzyme/primer-probe mix is added to each well of a new Fast 96-well plate (Applied Biosystem's TaqMan Fast Universal PCR Master Mix, Cat. No. 4352042)

| ApoB PCR Master Mix Components | uL/rxn | Final Conc. |
|---|---|---|
| Fast Enzyme Mix (2× stock) | 10 | |
| forward primer (100 uM) | 0.18 | 900 nM |
| reverse primer (100 uM) | 0.18 | 900 nM |
| probe (10 uM) | 0.05 | 250 nM |
| Water | 4.59 | |

ApoB primers and probe sequence:
(SEQ. ID. NO.: 12)
17063DC F3 GGCGCGAAATTTCAGGAATTGT (SEQ. ID. NO.: 13)
17063DC Pr2 CACTGGATACGACCTTTAACA (SEQ. ID. NO.: 14)
Universal R2 AGTGCAGGGTCCGAG 5 uL of each RT reaction is added to the Fast Enzyme Mix plate. The plate is centrifuged for 1 minute at 1000 rpm and the QPCR analysis is performed on an ABI7900 with Fast Block. Cycling parameters are: 1 cycle—95° C. for 20 seconds, followed by 40 Cycles—95° C. for 1 seconds, 60° C. for 20 seconds.

The QPCR result is utilized to calculate the siRNA concentration in the PEG antibody capture plate Triton lysates. Based on an estimate of 500 siRNA per LNP particle, the number of LNPs retained in each well of the anti-PEG antibody plate can be calculated. Using the ApoE concentration per well, as determined by the ApoE ELISA and the number of LNP particles per well, an approximate ApoE molecules bound per LNP particle can be calculated.

ApoE Molecules Bound Per LNP

| Compound | ApoE Molecules/LNP |
|---|---|
| 8 | 4.9 |
| 16 | 3.3 |
| 24 | 1.2 |
| 25 | 13.7 |
| 28 | 4.7 |
| 29 | 38 |
| 32 | 12.8 |
| 33 | 18.1 |
| 34 | 2.3 |
| 45 (KC2) | 32.5 |
| 46 (MC3) | 14.5 |

Example 3

Heparin Sepharose HI-TRAP™ Binding Assay

Lipid nanoparticles (LNP) with neutral surface charge are not retained after injection onto heparin sepharose with 1× Dulbecco's phosphate buffered saline (DPBS) as the running buffer but elute in the column void volume. Serum apolipoprotein E (ApoE) exhibits high affinity binding with heparin sulfate and it was shown that LNPs bind to heparin sepharose to an extent dependent on their intrinsic ability to bind ApoE (depending on both lipid nanoparticle composition and ApoE concentration) after incubation with purified and/or recombinant human ApoE or serum samples. Lipid nanoparticles with surface bound ApoE bind to heparin sepharose with high affinity and are eluted only at high salt (1M NaCl).

A heparin sepharose binding assay was developed to assess serum ApoE binding to lipid nanoparticles based on the high affinity interaction that ApoE-LNP complexes exhibit toward heparin sepharose.

Incubations

Lipid nanoparticles were incubated at 37° C. for 20 min at a final siRNA concentration of 50 µg/mL with various concentrations of either purified or recombinant human apolipoprotein E or 0.1-50% rat/mouse/rhesus monkey/human serum in 1× Dulbecco's phosphate buffered saline (DPBS). After incubation with ApoE or serum LNP samples were diluted 10-fold using 1×DPBS and analyzed by heparin sepharose chromatography. Peak area of retained LNP (after subtraction of appropriate blank signals) is compared to total peak area of LNP control without ApoE and/or serum incubation to determine the percentage of the LNP which undergoes shift to high affinity heparin interaction after incubation with ApoE/serum.

Heparin Sepharose HI-TRAP™ Chromatographic Conditions

A heparin sepharose HI-TRAP™ chromatography column (GE Healthcare; 1 mL bed volume) is equilibrated with either 1× or 2× Dulbecco's PBS; the higher 2× salt concentration is used for LNPs with higher intrinsic retention on heparin sepharose (presumably due to higher positive surface charge).

Mobile Phase A: 1× or 2×DPBS
Mobile Phase B: 1M NaCl in 10 mM sodium phosphate buffer, pH 7.0

100% A delivered isocratically for 10 min followed by step gradient to 100% B; hold for additional 10 min; step gradient back to 100% A and reequilibrate for additional 10 min prior to injection of next sample Flow rate: 1 mL/min
Sample injection volume: 50 µL.
Detection: UV @260 nm HI-TRAP™ Binding Results Upon Rhesus Serum Incubation (2×DPBS Conditions)

| Compound | % Bound |
|---|---|
| 32 | 100 |
| 33 | <5 |
| 45 (KC2) | 58 |
| 46 (MC3) | 7 |

Example 4

Rat In Vivo Evaluation of Efficacy and Toxicity

Figure 2:
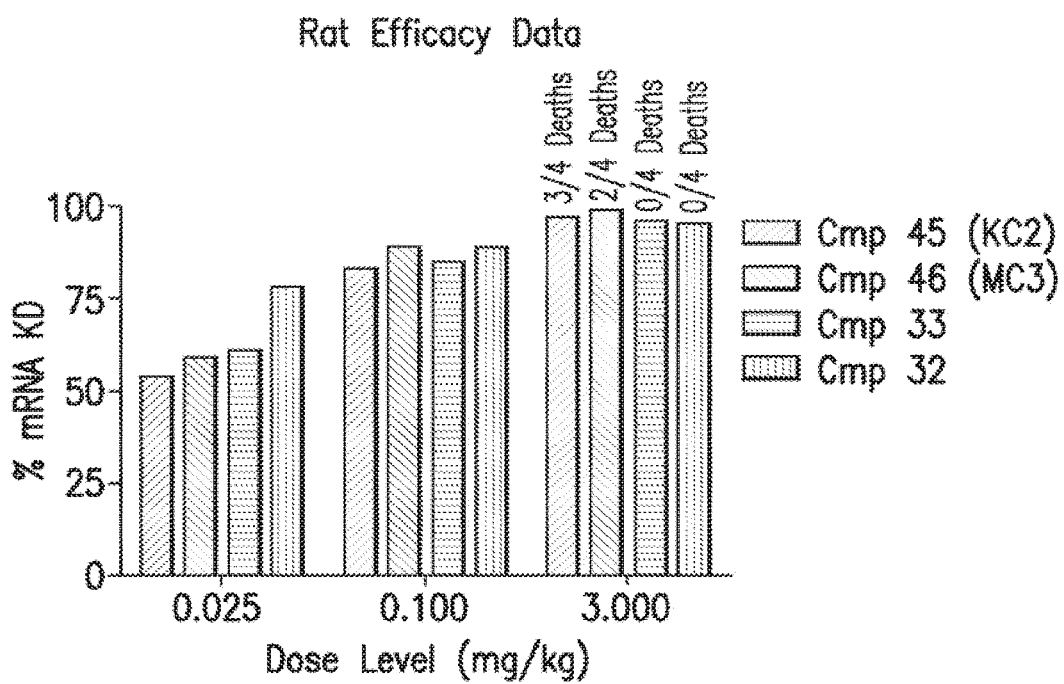
FIG. 2. LNP (Compounds 32 and 33) efficacy in rat (ApoB siRNA).

LNPs utilizing compounds in the nominal compositions described above, were evaluated for in vivo efficacy and increases in alanine amino transferase and aspartate amino transferase in Sprague-Dawley (Crl:CD(SD) female rats (Charles River Labs). The siRNA targets the mRNA transcript for the ApoB gene (Accession #NM 019287). The primary sequence and chemical modification pattern of the ApoB siRNA is displayed above. The RDVs (containing siRNA) in PBS vehicle were tail vein injected in a volume of 1 to 1.5 mL. Infusion rate is approximately 3 ml/min. Five rats were used in each dosing group. After LNP administration, rats are placed in cages with normal diet and water present. Six hours post dose, food is removed from the cages. Animal necropsy is performed 24 hours after LNP dosing. Rats are anesthetized under isoflurane for 5 minutes, then maintained under anesthesia by placing them in nose cones continuing the delivery of isoflurane until ex-sanguination is completed. Blood is collected from the vena cava using a 23 gauge butterfly venipuncture set and aliquoted to serum separator vacutainers for serum chemistry analysis. Punches of the excised caudate liver lobe are taken and placed in RNALater (Ambion) for mRNA analysis. Preserved liver tissue was homogenized and total RNA isolated using a Qiagen bead mill and the Qiagen miRNA-Easy RNA isolation kit following the manufacturer's instructions. Liver ApoB mRNA levels were determined by quantitative RT-PCR. Message was amplified from purified RNA utilizing a rat ApoB commercial probe set (Applied Biosystems Cat #RN01499054_m1). The PCR reaction was performed on an ABI 7500 instrument with a 96-well Fast Block. The ApoB mRNA level is normalized to the housekeeping PPIB (NM 011149) mRNA. PPIB mRNA levels were determined by RT-PCR using a commercial probe set (Applied Bisytems Cat. No. Mm00478295_m1). Results are expressed as a ratio of ApoB mRNA/PPIB mRNA. All mRNA data is expressed relative to the PBS control dose. Serum ALT and AST analysis were performed on the Siemens Advia 1800 Clinical Chemistry Analyzer utilizing the Siemens alanine aminotransferase (Cat #03039631) and aspartate aminotransferase (Cat #03039631) reagents. Similar efficacy and improved tolerability were observed in rats dosed with Compound 32 or 33 containing RDV than with the RDV containing the cationic lipid DLinKC2DMA (Compound 45) or MC3 (Compound 46, FIG. 2).

Example 5

Determination of Cationic Lipid Levels in Rat/Monkey Liver

Liver tissue was weighed into 20-ml vials and homogenized in 9 v/w of water using a GenoGrinder 2000 (OPS Diagnostics, 1600 strokes/min, 5 min). A 50 µL aliquot of each tissue homogenate was mixed with 300 µL of extraction/protein precipitating solvent (50/50 acetonitrile/methanol containing 500 nM internal standard) and the plate was centrifuged to sediment precipitated protein. A volume of 200 µL of each supernatant was then transferred to separate wells of a 96-well plate and 10 µl samples were directly analyzed by LC/MS-MS.

Standards were prepared by spiking known amounts of a methanol stock solution of compound into untreated rat liver homogenate (9 vol water/weight liver). Aliquots (50 µL) each standard/liver homogenate was mixed with 300 µL of extraction/protein precipitating solvent (50/50 acetonitrile/methanol containing 500 nM internal standard) and the plate was centrifuged to sediment precipitated protein. A volume of 200 µL of each supernatant was transferred to separate wells of a 96-well plate and 10 µl of each standard was directly analyzed by LC/MS-MS.

Absolute quantification versus standards prepared and extracted from liver homogenate was performed using an Aria LX-2 HPLC system (Thermo Scientific) coupled to an API 4000 triple quadrupole mass spectrometer (Applied Biosystems). For each run, a total of 10 µL sample was injected onto a BDS Hypersil C8 HPLC column (Thermo, 50×2 mm, 3 µm) at ambient temperature.

Mobile Phase A: 95% $H_2O$/5% methanol/10 mM ammonium formate/0.1% formic acid Mobile Phase B: 40% methanol/60% n-propanol/10 mM ammonium formate/0.1% formic acid. The flow rate was 0.5 mL/min and gradient elution profile was as follows: hold at 80% A for 0.25 min, linear ramp to 100% B over 1.6 min, hold at 100% B for 2.5 min, then return and hold at 80% A for 1.75 min. Total run time was 5.8 min. API 4000 source parameters were CAD: 4, CUR: 15, GS1: 65, GS2: 35, IS: 4000, TEM: 550, CXP: 15, DP: 60, EP: 10.

Figure 3:
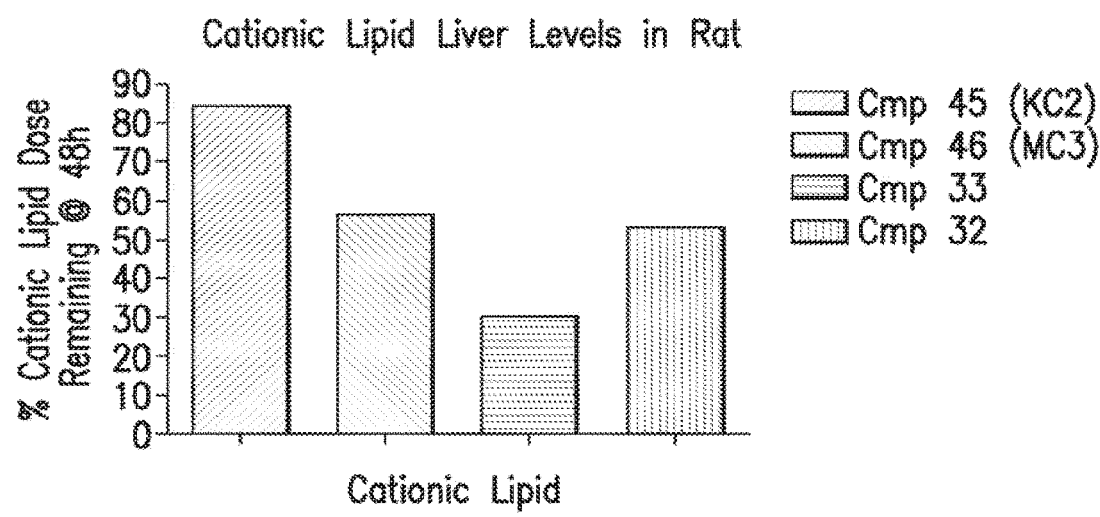
FIG. 3. Cationic lipid (Compounds 32 and 33) levels in rat liver.
Figure 7:
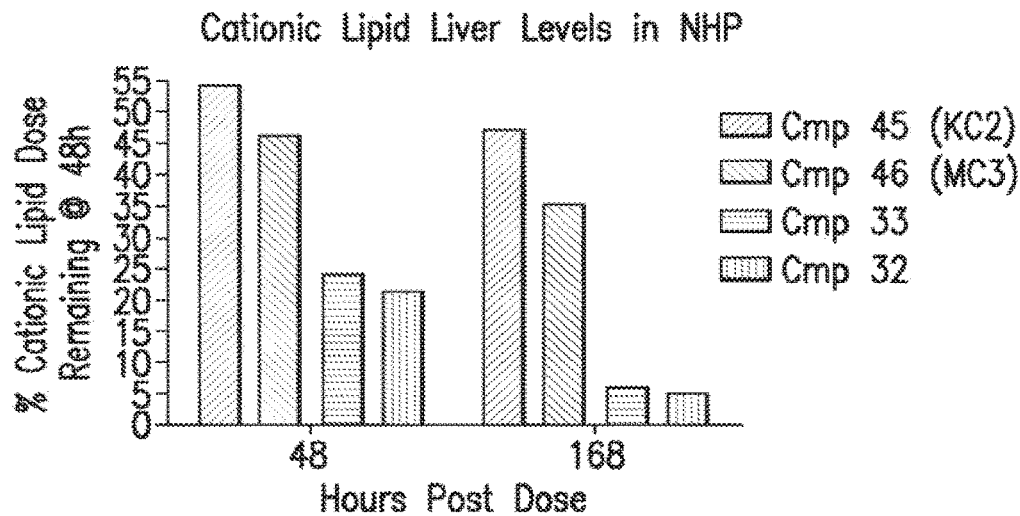
FIG. 7. Cationic lipid (Compounds 32 and 33) levels in NHP liver.

In rats dosed with Compound 32 or 33 containing RDV, liver levels were either similar to or lower than the RDV containing the cationic lipid DLinKC2DMA (Compound 45) or MC3 (Compound 46, FIG. 3). In monkeys dosed with Compound 32 or 33 containing RDV, liver levels were lower than the RDV containing the cationic lipid DLinKC2DMA (Compound 45) or MC3 (Compound 46, FIG. 7).

Example 6

Rhesus Monkey In Vivo Evaluation of ApoB Efficacy

Figure 4:
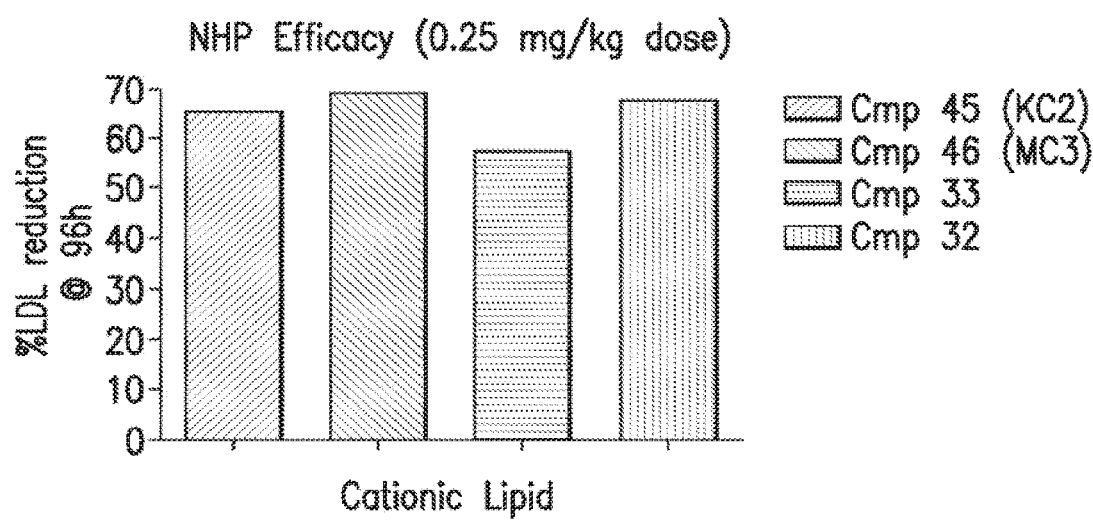
FIG. 4. LNP (Compound 32 and 33, ApoB siRNA) efficacy in NHP.

LNPs utilizing compounds in the nominal compositions described above, were evaluated for in vivo efficacy in male or female *Macaca mulatta* (rhesus) monkeys. The siRNA targets the mRNA transcript for the ApoB gene (Accession #XM 001097404). The primary sequence and chemical modification pattern of the ApoB siRNA is displayed above. The RDVs (containing siRNA) in PBS vehicle were administered by intravenous injection in the saphenous vein at an injection rate of 20 mL/minute to a dose level of 0.25 mg/kilogram siRNA. The injection volumes were from 1.9 to 2.1 mL/kilogram and monkeys ranged in weight from 2.5 to 4.5 kilograms. The RDV or PBS control were administered to three monkeys. At multiple days post dose, 1 mL blood samples were drawn from the femoral artery for serum chemistry analysis. Monkeys were fasted overnight prior to blood draws. As a measure of efficacy, LDL-C was monitored as a downstream surrogate marker of ApoB mRNA reduction. At 4 days post systemic administration of RDVs containing compounds 32 and 33 (0.25 mg/kg), serum levels of LDL-C were reduced to less than 30% of pre-dose levels (FIG. 4).

Example 7

Rhesus Monkey In Vivo Evaluation of β-Catenin Efficacy

On study day −7 predose liver biopsy samples (~0.5-1 gram/sample) were collected from male rhesus monkeys by laparoscopic surgical resection (resection of one biopsy sample from outer edge of one randomly selected liver lobe per monkey). A 5 mm tissue punch was used to sample three non-adjacent ~50 mg samples from each predose biopsy. Samples were preserved in RNAlater™ (Ambion) for later CTNNB1 mRNA analysis.

On study day 0 monkeys were administered suspensions of the lipid nanoparticle (LNP) test articles in phosphate buffered saline (0.05-0.1 mg siRNA/mL) via single-dose intravenous bolus injection at target doses of 0.67, 1.34 or 3.34 mg siRNA/$m^2$. For dosing purposes, body surface area ($m^2$) was estimated from body weight according to the established aliometric scaling relationship given below (1):

$$BSA(m^2)=0.11*BW(in\ kg)^{0.65}$$

On study days 7, 48 hours and 168 hrs post LNP administration, liver biopsy samples (~0.5-1 gram/sample) were collected from monkeys by laparoscopic surgical resection (2 separate randomly selected liver lobes were resected per monkey). A 5 mm tissue punch was used to sample three non-adjacent ~50 mg samples per each 48 hr and 168 hr surgical biopsy sample. Samples were preserved in RNAlater™ (Ambion) for later CTNNB1 mRNA analysis.

CTNNB1 mRNA levels were measured by relative quantitative RT-PCR using a primer/probe set validated for CTNNB1 and normalized against mRNA levels of peptidyl-prolyl isomerase B (also known as PPIB or cyclophilin B) and RNA levels of 18S ribosomal RNA (18S rRNA). Change in CTNNB1 mRNA liver expression was measured as the difference in PCR threshold cycle number (ΔΔCt) between post-dose samples and each corresponding monkey's predose liver samples.

Calculation of CTNNB1 mRNA knockdown (with respect to pretreatment levels) was calculated from ΔΔCt using the following relationship:

$$mRNA\ (\%\ knockdown)=100-(100/2^{-\Delta\Delta Ct})$$

Figure 5:
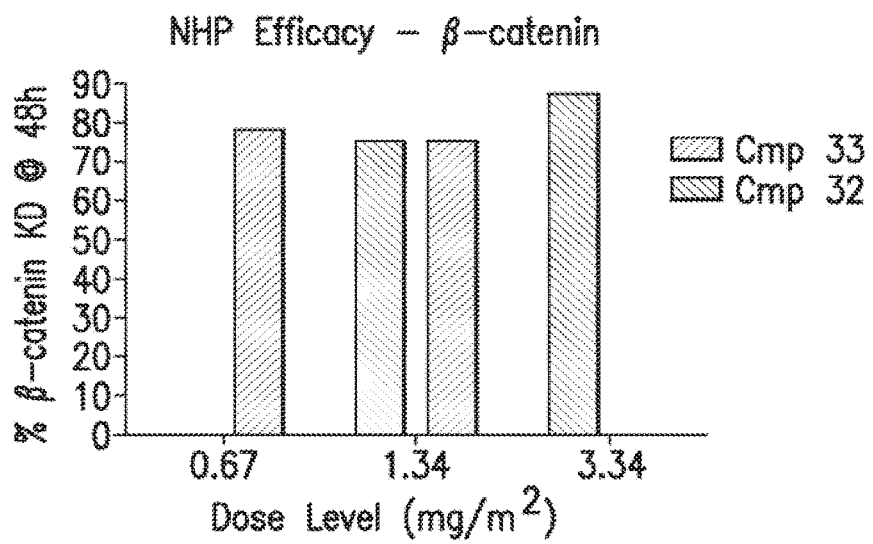
FIG. 5. LNP (Compound 32 and 33, β-catenin siRNA) efficacy in NHP.

Monkeys dosed with RDVs containing compounds 32 and 33 and beta-catenin siRNA demonstrated robust KD at doses ranging from 0.67-3.34 mg/$m^2$ (FIG. 5).

(1) FDA Guidance Document: "Guidance for Industry: Estimating the Maximum Safe Starting Dose in Initial Clinical Trials for Therapeutics in Adult Healthy Volunteers" July 2005. US Department of Health and Human Services, Food and Drug Administration—Center for Drug Evaluation and Research (CDER)

Example 8

Rhesus Monkey In Vivo Evaluation of ALT Increases

Alanine aminotransferase (ALT) is measured in serum that is harvested from clotted monkey whole blood after centrifugation. A Roche Modular System automated chemistry analyzer measures the enzymatic activity of ALT in the serum by using International Federation of Clinical Chemistry standardized procedures and reagents. The analyzer's computer uses absorbance measurements to calculated ALT activity in the sample as compared to a standard curve. The ALT activity is reported in International Units per Liter (IU/L).

Figure 6:
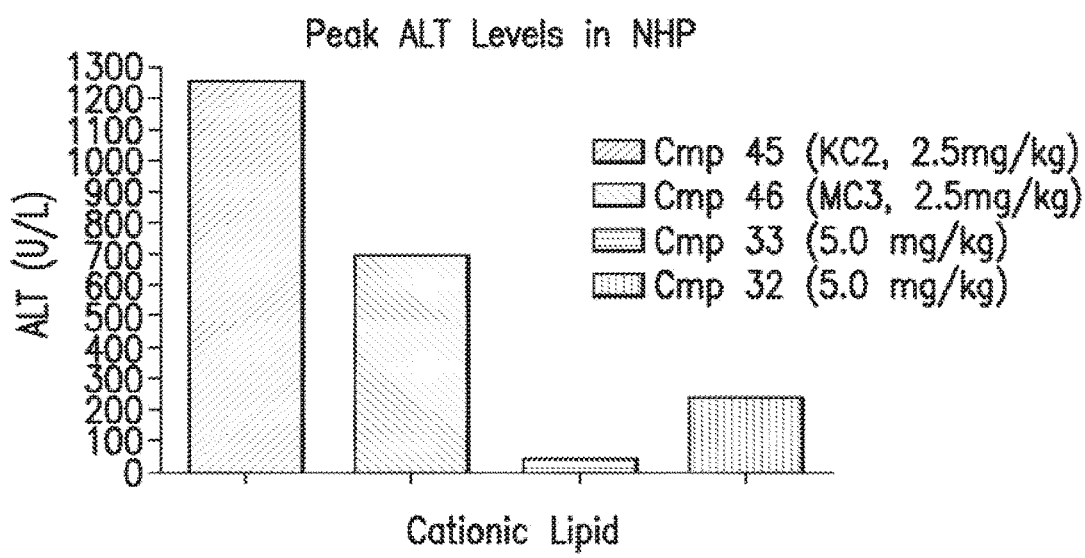
FIG. 6. Peak ALT levels in NHP post LNP dose (Compound 32 and 33).

Monkeys dosed with RDVs containing compounds 32 and 33 had lower peak ALT elevations than those dosed with the RDV containing the cationic lipid DLinKC2DMA (Compound 45) or MC3 (Compound 46, FIG. 6).

Example 9

Evaluation in Hepatocelluar Carcinoma Mouse Model

The activity LNPs in delivering a β-catenin siRNA (siRNAβ-cat) to hepatocellular carcinoma was evaluated in a mouse hepatocellular carcinoma (HCC) model, named TRE-MET. TRE-MET mice are transgenic mice in an FVB/N genetic background where the human MET transgene is expressed under an hCMV promoter with hepatamerized upstream tet-operators. When TRE-MET mice are crossed with the LAP-tTA line, the double transgenic (TRE-MET/LAP-tTA) mice express MET in a liver-specific manner which can be suppressed by administration of doxycycline. These mice develop HCC at 3 months of age with visually identifiable tumor nodules on the liver surface and the tumors display a diffuse trabecular growth pattern typical for HCC and express the HCC tumor marker alpha-fetoprotein (AFP). In addition, the mutation analysis in the tumor of TRE-MET mice has also identified activating mutations in the beta-catenin gene in approximately 95% of tumors. These features make the TRE-MET HCC mouse model suitable for evaluating LNP-mediated delivery of β-catenin siRNA and the resultant efficacy on tumor growth.

Figure 8:
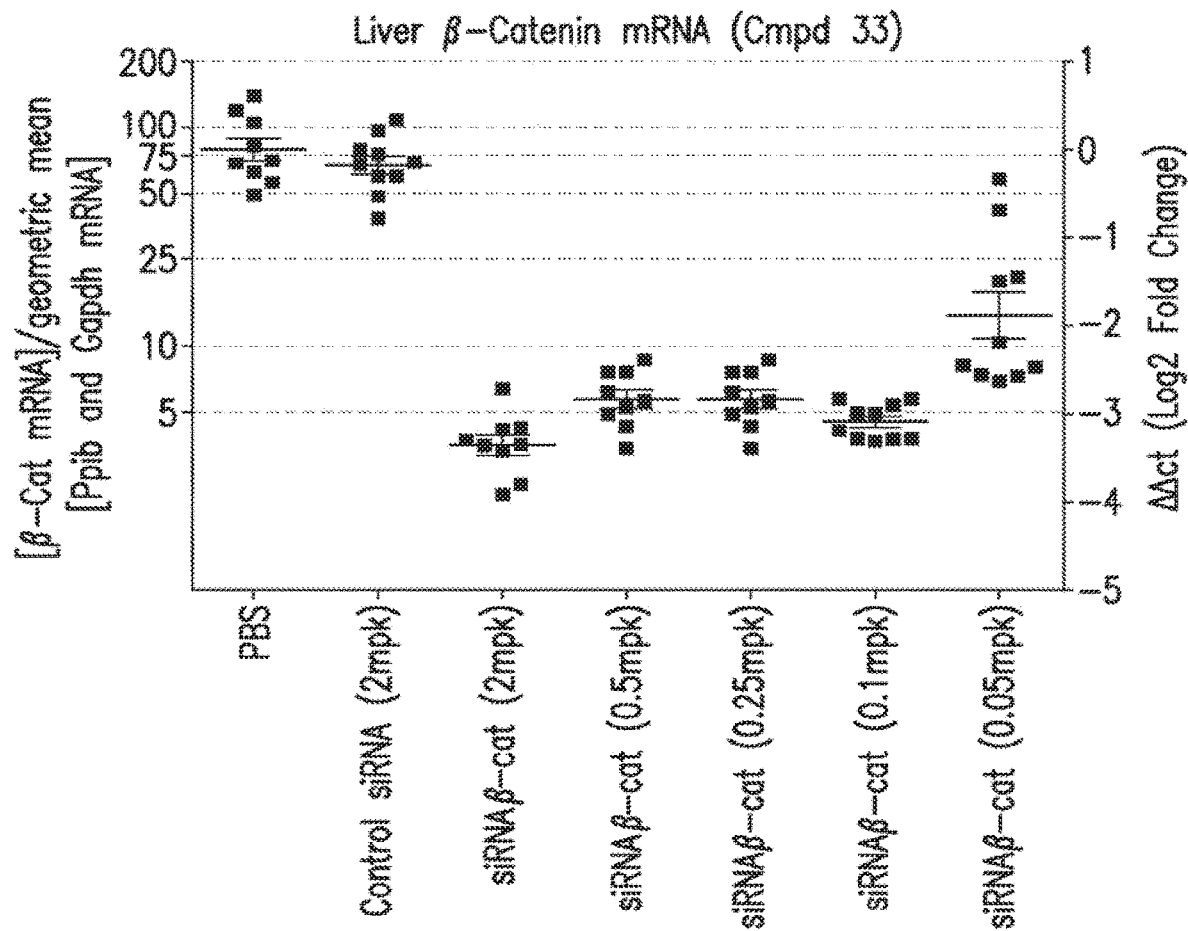
FIG. 8. Liver β-catenin mRNA KD in TRE-Met mice (Compound 33).
Figure 9:
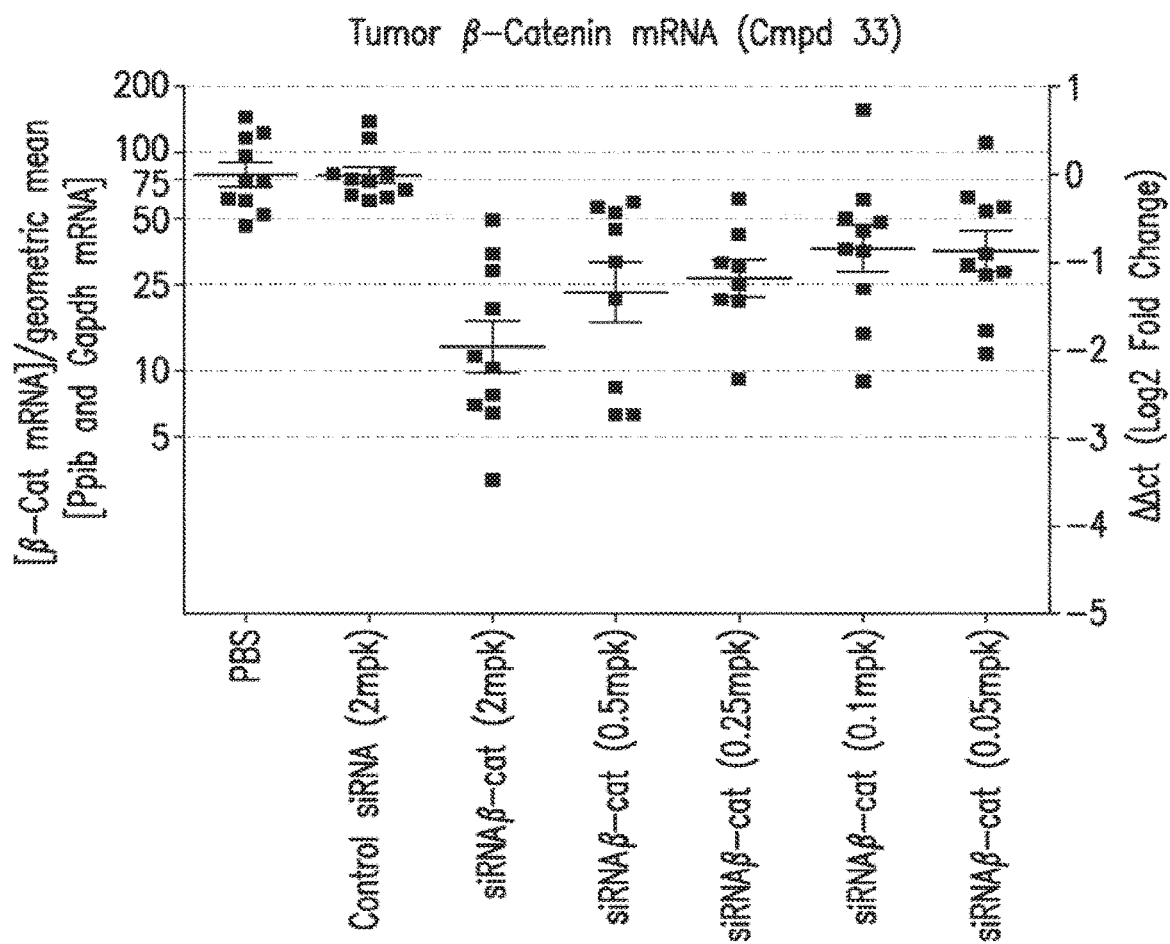
FIG. 9. Tumor β-catenin mRNA KD in TRE-Met mice (Compound 33).
Figure 12:
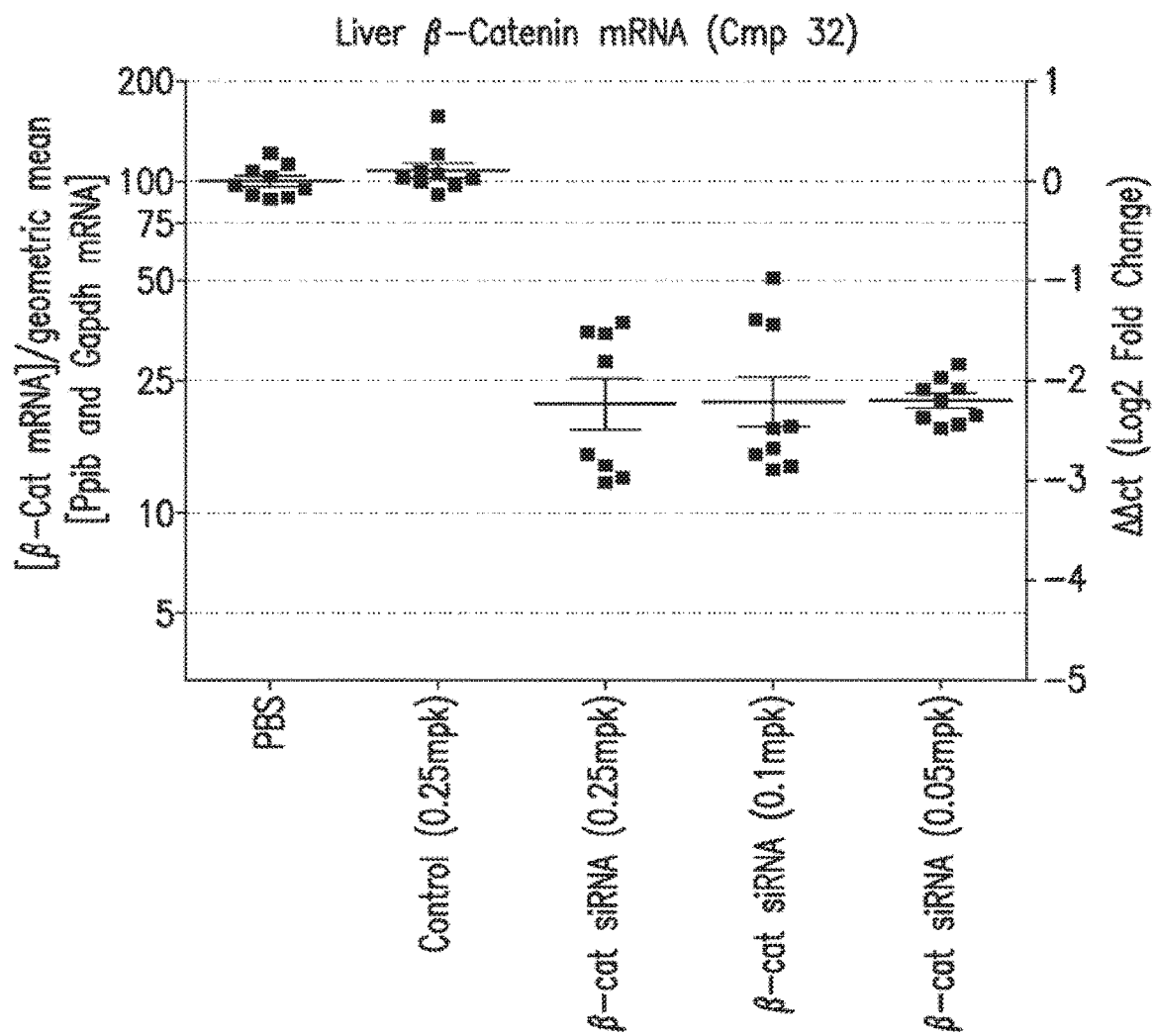
FIG. 12. Liver β-catenin mRNA KD in TRE-Met mice (Compound 32).
Figure 13:
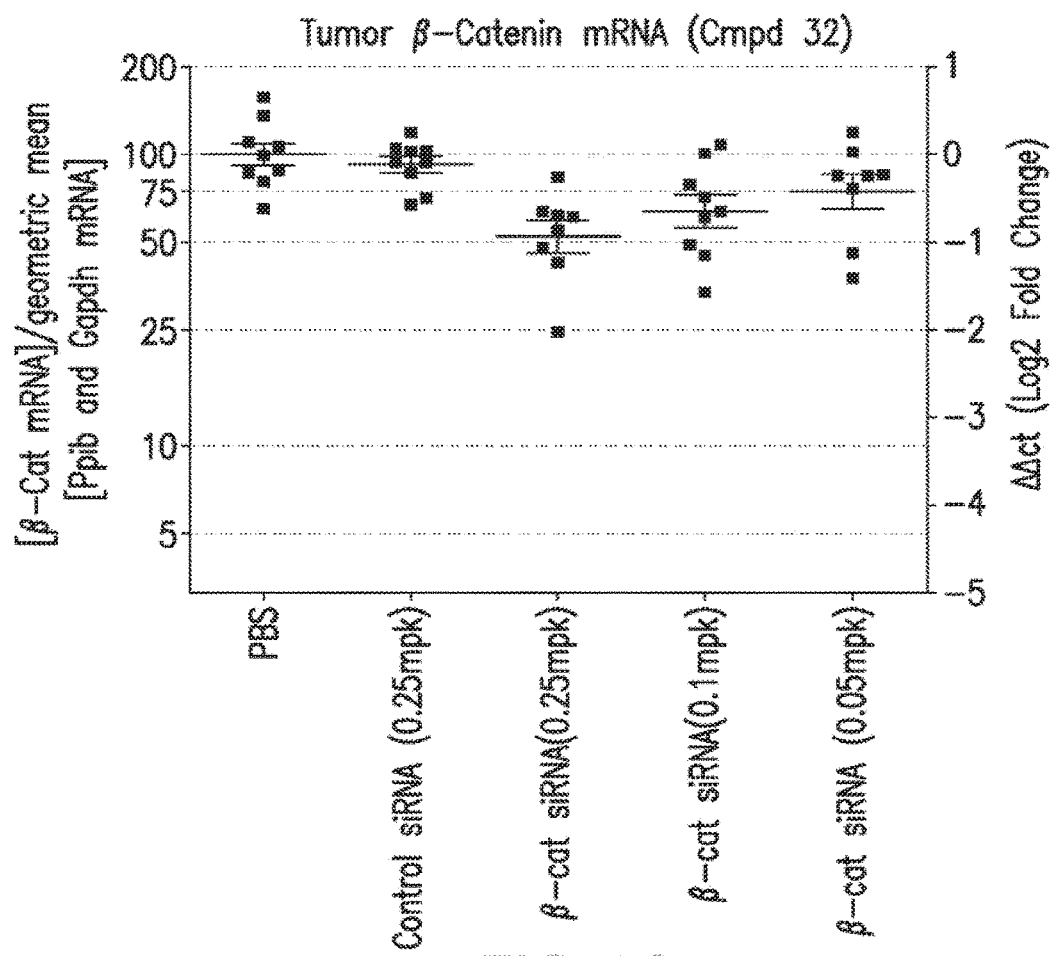
FIG. 13. Tumor β-catenin mRNA KD in TRE-Met mice (Compound 32).

The effect of β-catenin containing LNPs in silencing β-catenin mRNA in both liver and tumor tissues was first evaluated in a pharmacodynamic (PD) study in TRE-MET mice bearing tumors. Different doses of LNPs or a high dose of LNPcontrol siRNA were intravenously administered and 72 hours later, necropsy was performed to collect liver and tumor tissues for the determination of β-catenin mRNA levels by Taqman. As shown in FIGS. 8 and 9, Compound 33 induced robust and dose-dependent knockdown of β-catenin mRNA in both liver and tumor tissues, whereas no β-catenin knockdown was observed in animals receiving control siRNA or PBS. 0.1 mpk and 0.05 mpk of LNP induced 88% and 69% KD in normal liver respectively. The KD in tumors ranges from 70% (2 mpk) to about 40% (0.1 or 0.05 mpk). As shown in FIGS. 12 and 13, Compound 32 induced robust and dose-dependent knockdown of β-catenin mRNA in both liver and tumor tissues, whereas no β-catenin knockdown was observed in animals receiving control siRNA or PBS. 0.1 mpk and 0.05 mpk of LNP induced 76% and 78% KD in normal liver respectively. The KD in tumors ranges from 47% (0.25 mpk) to about 20-30% (0.1 or 0.05 mpk).

Figure 10:
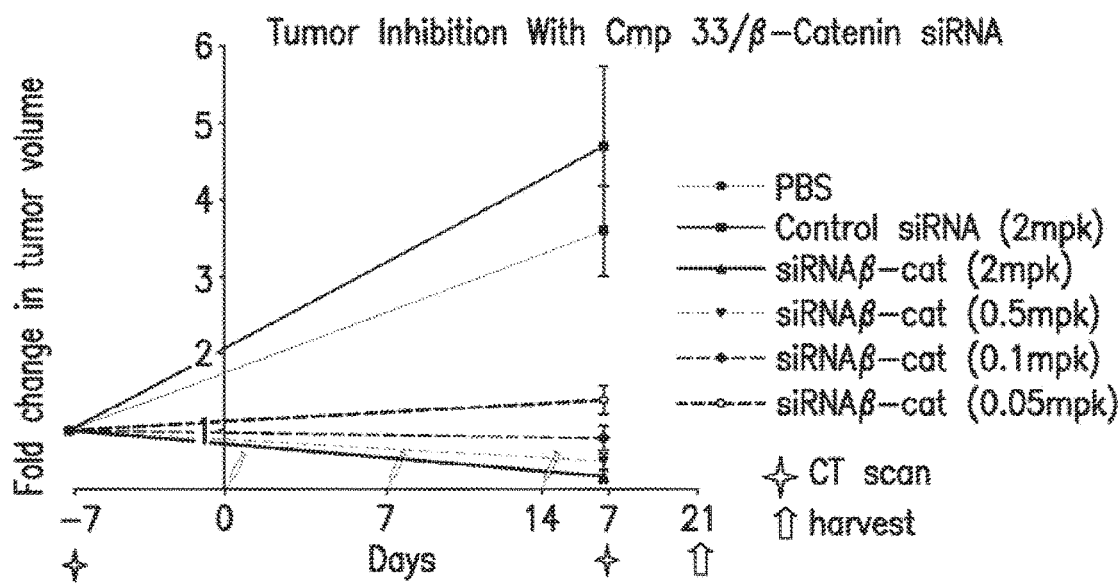
FIG. 10. Tumor growth inhibition (Compound 33) in TRE-met mice.
Figure 14:
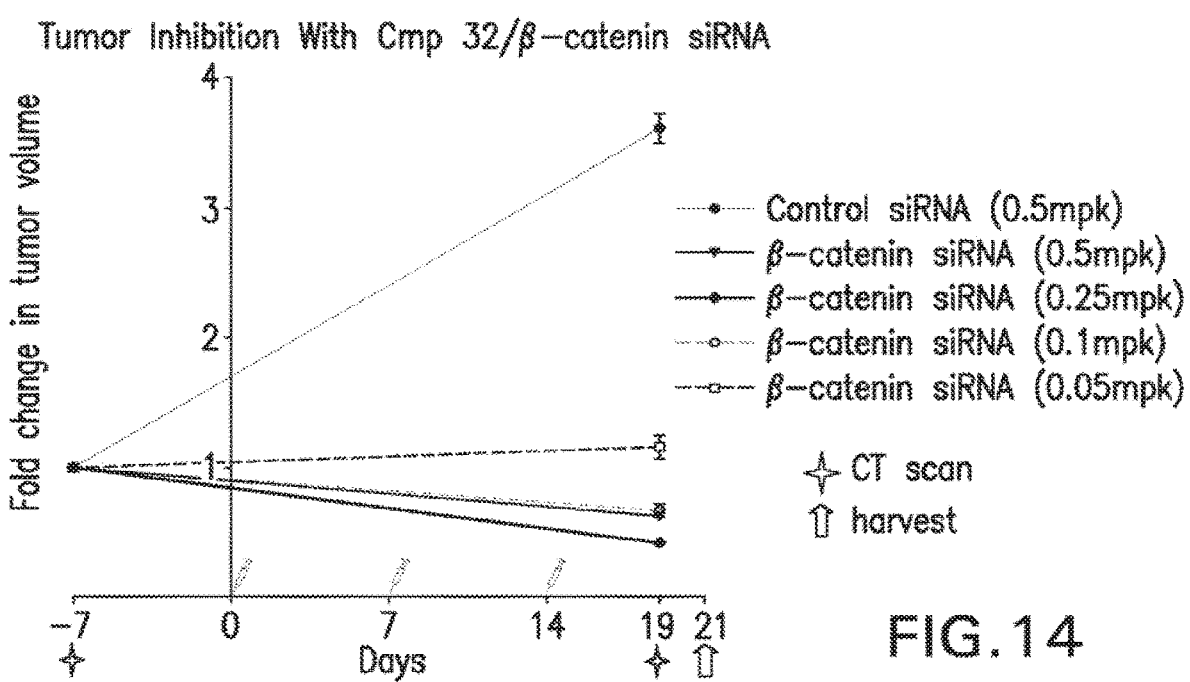
FIG. 14. Tumor growth inhibition (Compound 32) mTRE-met mice.

The effect of LNP on tumor growth was evaluated in multiple-dose efficacy study. TRE-MET HCC mice were dosed with Compound 33/siRNAβ-cat, Compound 32/siRNAb-cat, control siRNA or PBS weekly for 3 weeks (3 doses) and the tumor volume in each animal was determined 7 days prior to the $1^{st}$ dose and 3 days post the final dose by microCT scan (FIGS. 10 and 14). In addition, 7 days after the final dose, liver and tumor tissues were collected for the assessment of β-catenin mRNA levels. While mice receiving PBS or control siRNA showed 360-470% growth in tumor burden, mice treated with Compound 33/siRNAβ-cat exhibited profound tumor growth inhibition or regression in a dose-dependent manner (FIG. 10). 2 mpk and 0.5 mpk of Compound 33/si RNAβ-cat induced 60% and 40% tumor regression respectively and 0.05 mpk caused tumor stasis. While mice receiving PBS or control siRNA showed ~350% growth in tumor burden, mice treated with Compound 32/siRNAβ-cat exhibited profound tumor growth inhibition or regression, in a dose-dependent manner (FIG. 14). 0.5, 0.25 and 0.1 mg/kg of Compound 32/siRNAβ-cat induced 37, 58, and 37% tumor regression respectively and 0.05 mpk caused lumor stasis.

What is claimed is:

1. A cationic lipid of Formula A:

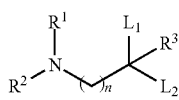

wherein:
$R^1$ and $R^2$ are each methyl;
$R^3$ is H;
n is 0;
$L_1$ is an alkyl selected from the following structures:

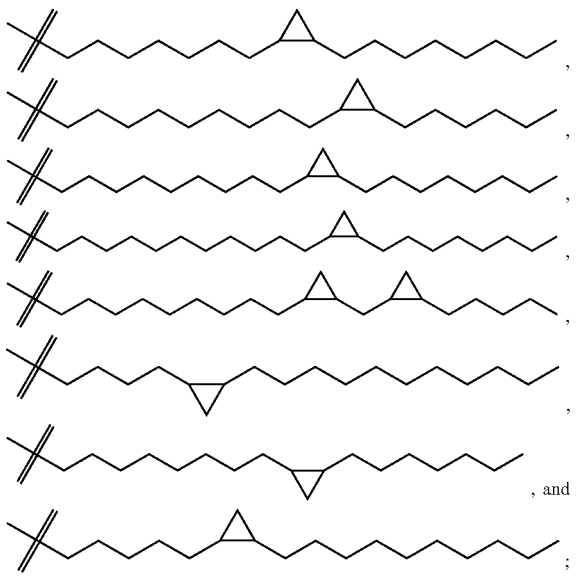

and
$L_2$ is $C_3$-$C_9$ alkyl or $C_3$-$C_9$ alkenyl;
or any pharmaceutically acceptable salt or stereoisomer thereof.

2. The cationic lipid of claim 1,
wherein:
$R^1$ and $R^2$ are each methyl;
$R^3$ is H;
n is 0;
and
$L_2$ is $C_3$-$C_9$ alkyl;
or any pharmaceutically acceptable salt or stereoisomer thereof.

3. The cationic lipid of claim 1, wherein the cationic lipid is selected from:
N,N-dimethyl-1-[(1S,2R)-2-octylcyclopropyl]heptadecan-8-amine (Compound 33);
1-[(1S,2R)-2-hexylcyclopropyl]-N,N-dimethylnonadecan-10-amine (Compound 34);
N,N-dimethyl-1-[(1S,2R)-2-octylcyclopropyl]nonadecan-10-amine (Compound 35);
N,N-dimethyl-21-[(1S,2R)-2-octylcyclopropyl]henicosan-10-amine (Compound 36);
N,N-dimethyl-1-[(1 S,2 S)-2-{[(1R,2R)-2-pentylcyclopropyl]methyl} cyclopropyl]nonadecan-10-amine (Compound 37);
N,N-dimethyl-1-[(1 S,2R)-2-octylcyclopropyl]hexadecan-8-amine (Compound 38);
N,N-dimethyH-[(1R,2S)-2-undecyl cyclopropyl]tetradecan-5-amine (Compound 39);
1-[(1R,2S)-2-heptylcyclopropyl]-N,N-dimethyloctadecan-9-amine (Compound 41);
1-[(1 S,2R)-2-decylcyclopropyl]-N,N-dimethylpentadecan-6-amine (Compound 42);
N,N-dimethyl-1-[(1S,2R)-2-octylcyclopropyl]pentadecan-8-amine (Compound 43);
or any pharmaceutically acceptable salt or stereoisomer thereof.

4. A lipid nanoparticle comprising a cationic lipid of Formula A:

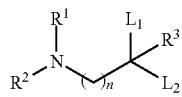

wherein:
$R^1$ and $R^2$ are independently methyl;
$R^3$ is H;
n is 0;
$L_1$ is $C_4$-$C_{24}$ alkenyl or an alkyl selected from the following structures:

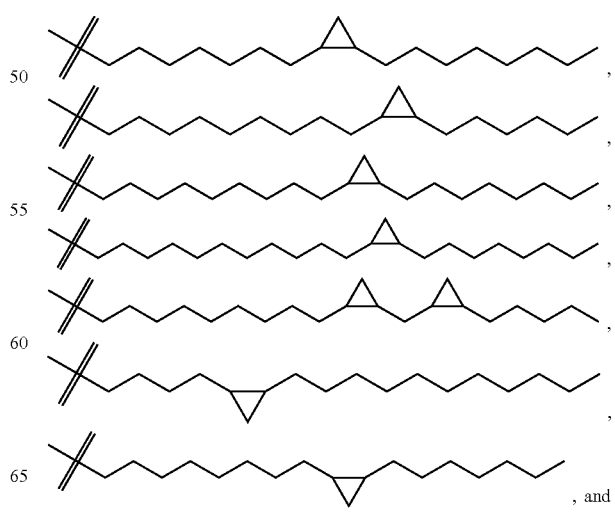

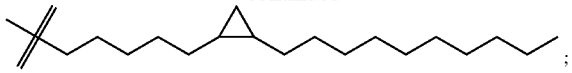

and

L$_2$ is C$_3$-C$_9$ alkyl or C$_3$-C$_9$ alkenyl, or any pharmaceutically acceptable salt or stereoisomer thereof.

5. The lipid nanoparticle of claim 4, wherein the lipid nanoparticle further comprises cholesterol, DSPC and PEG-DMG.

6. The lipid nanoparticle of claim 4, wherein the lipid nanoparticle further comprises an oligonucleotide.

7. The lipid nanoparticle of claim 6, wherein the oligonucleotide is siRNA.

8. A cationic lipid selected from the group consisting of:
(20Z,23Z)—N,N-dimethylnonacosa-20,23-dien-10-amine (Compound 1);
(17Z,20Z)—N,N-dimemylhexacosa-17,20-dien-9-amine (Compound 2);
(16Z, 19Z)—N,N~dimethylpentacosa-16,19-dien-8-amine (Compound 3);
(13Z,16Z)—N,N-dimethyldocosa-13,16-dien-5-amine (Compound 4);
(12Z,15Z)—N,N-dimethylhenicosa-12,15-dien-4-amine (Compound 5);
(14Z,17Z)—N,N-dimethyltricosa-14,17-dien-6-amine (Compound 6);
(15Z,18Z)—N,N-dimethyltetracosa-15,18-dien-7-amine (Compound 7);
(18Z,21Z)—N,N-dimethylheptacosa-18,21-dien-10-amine (Compound 8);
(15Z,18Z)—N,Ndimethylheptacosa-15,18-dien-5-amine (Compound 9);
(14Z,17Z)—N,N-dimethyltricosa-14,17-dien-4-amine (Compound 10);
(19Z,22Z)—N,N-dimethyloctacosa-19,22-dien-9-amine (Compound 11);
(18Z,21 Z)—N,N-dimethylheptacosa-18,21-dien-8-amine (Compound 12);
(17Z,20Z)—N,N-dimethylhexacosa-17,20-dien-7-amine (Compound 13);
(16Z;19Z)—N,N-dimethylpentacosa-16,19-dien-6-amine (Compound 14);
(22Z,25Z)—N,N-dimethylhentriaconta-22,25-dien-10-amine (Compound 15);
(21Z,24Z)—N,N-dimethyltriaconta-21,24-dien-9-amine (Compound 16);
(18Z)—N,N-dimetylheptacos-18-en-10-amine (Compound 17);
(17Z)—N,N-dimethylhexacos-17-en-9-amine (Compound 18);
(19Z,22Z)—N,N-dimethyloctacosa-19,22-dien-7-amine (Compound 19);
N,N-dimethylheptacosan-10-amine (Compound 20);
(20Z,23Z)—N-ethyl-N-methylnonacosa-20,23-dien-10-amine (Compound 21);
1-[(11Z,14Z)-1-nonylicosa-11,14-dien-1-yl] pyrrolidine (Compound 22);
(20Z)—N,N-dimethylheptacos-20-en-10-amine (Compound 23);
(15Z)—N,N-dimethylheptacos-15-en-10-amine (Compound 24);
(14Z)—N,N-dimethylnonacos-14-en-10-amine (Compound 25);
(17Z)—N,N-dimethylnonacos-17-en-10-amine (Compound 26);
(24Z)—N,N-dimethyltritriacont-24-en-10-amine (Compound 27);
(20Z)—N,N-dimethylnonacos-20-en-10-amine (Compound 28);
(22Z)—N,N-dimethylhentriacont-22-en-10-amine (Compound 29);
(16Z)—N,N-dimethylpentacos-16-en-8-amine (Compound 30);
(11E,20Z,23Z)—N,N-dimethylnonacosa-11,20,23-trien-10-amine (Compound 44)
or any pharmaceutically acceptable salt or stereoisomer thereof.

9. The lipid nanoparticle of claim 4, wherein L$_1$ is C$_4$-C$_{24}$ alkenyl.

10. The lipid nanoparticle of claim 4, wherein L$_1$ is C$_{12}$-C$_{24}$ alkenyl.

11. The lipid nanoparticle of claim 10, wherein Li a linear C$_{12}$-C$_{24}$ alkenyl.

12. The lipid nanoparticle of claim 11, wherein L$_2$ is C$_3$-C$_9$alkyl.

13. The lipid nanoparticle of claim 4, wherein Li is selected from the group consisting of:

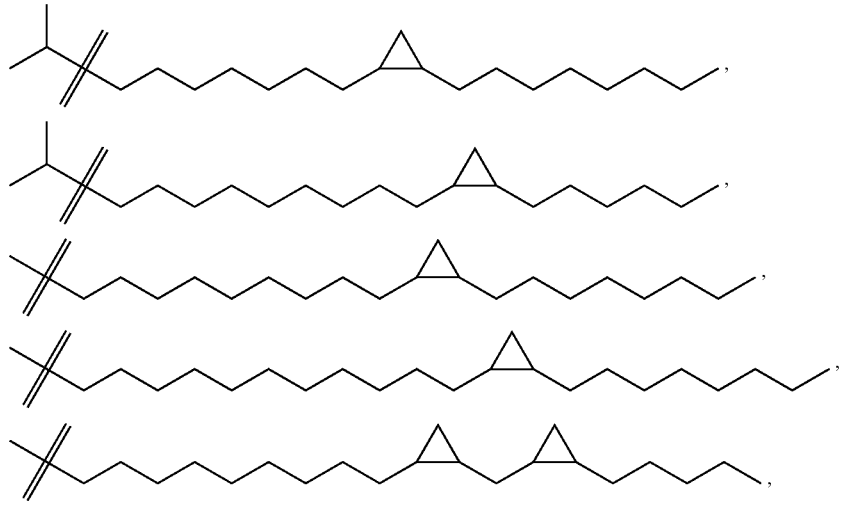

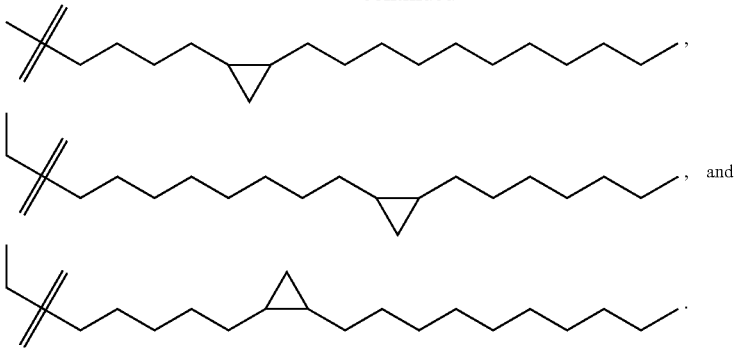

14. The lipid nanoparticle of claim 13, wherein $L_2$ is $C_3$-$C_9$ alkyl.

15. The lipid nanoparticle of claim 4, wherein the lipid nanoparticle further comprises cholesterol, DSPC, and a PEG lipid.

16. The lipid nanoparticle of claim 15, wherein the PEG lipid is PEG-C-DMA or PEG-DMG.

17. A lipid nanoparticle comprising a cationic lipid of claim 3.

18. The lipid nanoparticle of claim 17, wherein the lipid nanoparticle further comprises cholesterol, DSPC, and a PEG lipid.

19. The lipid nanoparticle of claim 18, wherein the PEG lipid is PEG-C-DMA or PEG-DMG.

20. A lipid nanoparticle comprising a cationic lipid of claim 8.

21. The lipid nanoparticle of claim 20, wherein the lipid nanoparticle further comprises cholesterol, DSPC, and a PEG lipid.

22. The lipid nanoparticle of claim 21, wherein the PEG lipid is PEG-C-DMA or PEG-DMG.

23. A lipid nanoparticle comprising N,N-dimethyl-1-[(1S, 2R)-2-octylcyclopropyl] heptadecan-8-amine (Compound 33).

24. The lipid nanoparticle of claim 23, wherein the lipid nanoparticle further comprises cholesterol, DSPC, and a PEG lipid.

25. The lipid nanoparticle of claim 24, wherein the PEG lipid is PEG-C-DMA or PEG-DMG.

* * * * *

SEQUENCE LISTING

```
<160> NUMBER OF SEQ ID NOS: 14

<210> SEQ ID NO 1
<211> LENGTH: 21
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(19)
<223> OTHER INFORMATION: ribonucleotide modified or unmodified as
      described for this sequence
<220> FEATURE:
<221> NAME/KEY: misc_feature
<222> LOCATION: (1)..(1)
<223> OTHER INFORMATION: inverted deoxy abasic
<220> FEATURE:
<221> NAME/KEY: misc_feature
<222> LOCATION: (1)..(1)
<223> OTHER INFORMATION: 2' deoxy
<220> FEATURE:
<221> NAME/KEY: misc_feature
<222> LOCATION: (2)..(2)
<223> OTHER INFORMATION: 2' fluoro
<220> FEATURE:
<221> NAME/KEY: misc_feature
<222> LOCATION: (3)..(6)
```

```
<223> OTHER INFORMATION: 2' deoxy
<220> FEATURE:
<221> NAME/KEY: misc_feature
<222> LOCATION: (7)..(8)
<223> OTHER INFORMATION: 2' fluoro
<220> FEATURE:
<221> NAME/KEY: misc_feature
<222> LOCATION: (9)..(9)
<223> OTHER INFORMATION: 2' deoxy
<220> FEATURE:
<221> NAME/KEY: misc_feature
<222> LOCATION: (10)..(10)
<223> OTHER INFORMATION: 2' fluoro
<220> FEATURE:
<221> NAME/KEY: misc_feature
<222> LOCATION: (11)..(17)
<223> OTHER INFORMATION: 2' deoxy
<220> FEATURE:
<221> NAME/KEY: misc_feature
<222> LOCATION: (18)..(18)
<223> OTHER INFORMATION: 2' fluoro
<220> FEATURE:
<221> NAME/KEY: misc_feature
<222> LOCATION: (19)..(21)
<223> OTHER INFORMATION: 2' deoxy
<220> FEATURE:
<221> NAME/KEY: misc_feature
<222> LOCATION: (21)..(21)
<223> OTHER INFORMATION: inverted deoxy abasic

<400> SEQUENCE: 1
auaaggcuau gaagagauat t                                               21

<210> SEQ ID NO 2
<211> LENGTH: 21
<212> TYPE: RNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(3)
<223> OTHER INFORMATION: ribose
<220> FEATURE:
<221> NAME/KEY: misc_feature
<222> LOCATION: (4)..(9)
<223> OTHER INFORMATION: 2' fluoro
<220> FEATURE:
<221> NAME/KEY: misc_feature
<222> LOCATION: (10)..(10)
<223> OTHER INFORMATION: 2' O-methyl
<220> FEATURE:
<221> NAME/KEY: misc_feature
<222> LOCATION: (11)..(11)
<223> OTHER INFORMATION: 2' fluoro
<220> FEATURE:
<221> NAME/KEY: misc_feature
<222> LOCATION: (12)..(13)
<223> OTHER INFORMATION: 2' O-methyl
<220> FEATURE:
<221> NAME/KEY: misc_feature
<222> LOCATION: (14)..(17)
<223> OTHER INFORMATION: 2' fluoro
<220> FEATURE:
<221> NAME/KEY: misc_feature
<222> LOCATION: (18)..(18)
<223> OTHER INFORMATION: 2' O-methyl
<220> FEATURE:
<221> NAME/KEY: misc_feature
<222> LOCATION: (19)..(19)
<223> OTHER INFORMATION: 2' fluoro
<220> FEATURE:
<221> NAME/KEY: misc_feature
<222> LOCATION: (20)..(21)
<223> OTHER INFORMATION: 2' O-methyl

<400> SEQUENCE: 2
```
uaucucuuca uagccuuauu u                                           21

<210> SEQ ID NO 3
<211> LENGTH: 21
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(1)
<223> OTHER INFORMATION: inverted deoxy abasic
<220> FEATURE:
<221> NAME/KEY: misc_feature
<222> LOCATION: (1)..(4)
<223> OTHER INFORMATION: 2' O-methyl
<220> FEATURE:
<221> NAME/KEY: misc_feature
<222> LOCATION: (5)..(6)
<223> OTHER INFORMATION: 2' fluoro
<220> FEATURE:
<221> NAME/KEY: misc_feature
<222> LOCATION: (7)..(7)
<223> OTHER INFORMATION: 2' O-methyl
<220> FEATURE:
<221> NAME/KEY: misc_feature
<222> LOCATION: (8)..(9)
<223> OTHER INFORMATION: 2' fluoro
<220> FEATURE:
<221> NAME/KEY: misc_feature
<222> LOCATION: (10)..(14)
<223> OTHER INFORMATION: 2' O-methyl
<220> FEATURE:
<221> NAME/KEY: misc_feature
<222> LOCATION: (15)..(18)
<223> OTHER INFORMATION: 2' fluoro
<220> FEATURE:
<221> NAME/KEY: misc_feature
<222> LOCATION: (19)..(19)
<223> OTHER INFORMATION: 2' O-methyl
<220> FEATURE:
<221> NAME/KEY: misc_feature
<222> LOCATION: (20)..(21)
<223> OTHER INFORMATION: 2' deoxy
<220> FEATURE:
<221> NAME/KEY: misc_feature
<222> LOCATION: (20)..(21)
<223> OTHER INFORMATION: phophorothioate linkage
<220> FEATURE:
<221> NAME/KEY: misc_feature
<222> LOCATION: (21)..(21)
<223> OTHER INFORMATION: inverted deoxy abasic

<400> SEQUENCE: 3
cuuuaacaau uccugaaaut t                                           21

<210> SEQ ID NO 4
<211> LENGTH: 21
<212> TYPE: RNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(3)
<223> OTHER INFORMATION: ribose
<220> FEATURE:
<221> NAME/KEY: misc_feature
<222> LOCATION: (1)..(4)
<223> OTHER INFORMATION: phophorothioate linkage
<220> FEATURE:
<221> NAME/KEY: misc_feature
<222> LOCATION: (4)..(5)
<223> OTHER INFORMATION: 2' O-methyl
<220> FEATURE:

```
<221> NAME/KEY: misc_feature
<222> LOCATION: (6)..(10)
<223> OTHER INFORMATION: 2' fluoro
<220> FEATURE:
<221> NAME/KEY: misc_feature
<222> LOCATION: (11)..(12)
<223> OTHER INFORMATION: 2' O-methyl
<220> FEATURE:
<221> NAME/KEY: misc_feature
<222> LOCATION: (13)..(14)
<223> OTHER INFORMATION: 2' fluoro
<220> FEATURE:
<221> NAME/KEY: misc_feature
<222> LOCATION: (15)..(15)
<223> OTHER INFORMATION: 2' O-methyl
<220> FEATURE:
<221> NAME/KEY: misc_feature
<222> LOCATION: (16)..(19)
<223> OTHER INFORMATION: 2' fluoro
<220> FEATURE:
<221> NAME/KEY: misc_feature
<222> LOCATION: (20)..(21)
<223> OTHER INFORMATION: phophorothioate linkage
<220> FEATURE:
<221> NAME/KEY: misc_feature
<222> LOCATION: (20)..(21)
<223> OTHER INFORMATION: 2' O-methyl

<400> SEQUENCE: 4
auuucaggaa uuguuaaagu u                                              21

<210> SEQ ID NO 5
<211> LENGTH: 21
<212> TYPE: RNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(1)
<223> OTHER INFORMATION: inverted deoxy abasic
<220> FEATURE:
<221> NAME/KEY: misc_feature
<222> LOCATION: (1)..(2)
<223> OTHER INFORMATION: ribose
<220> FEATURE:
<221> NAME/KEY: misc_feature
<222> LOCATION: (3)..(3)
<223> OTHER INFORMATION: 2' O-methyl
<220> FEATURE:
<221> NAME/KEY: misc_feature
<222> LOCATION: (4)..(5)
<223> OTHER INFORMATION: ribose
<220> FEATURE:
<221> NAME/KEY: misc_feature
<222> LOCATION: (6)..(8)
<223> OTHER INFORMATION: 2' O-methyl
<220> FEATURE:
<221> NAME/KEY: misc_feature
<222> LOCATION: (9)..(10)
<223> OTHER INFORMATION: ribose
<220> FEATURE:
<221> NAME/KEY: misc_feature
<222> LOCATION: (11)..(12)
<223> OTHER INFORMATION: 2' O-methyl
<220> FEATURE:
<221> NAME/KEY: misc_feature
<222> LOCATION: (13)..(14)
<223> OTHER INFORMATION: ribose
<220> FEATURE:
<221> NAME/KEY: misc_feature
<222> LOCATION: (15)..(21)
<223> OTHER INFORMATION: 2' O-methyl
<220> FEATURE:
<221> NAME/KEY: misc_feature
<222> LOCATION: (20)..(21)
<223> OTHER INFORMATION: phophorothioate linkage
```

```
<220> FEATURE:
<221> NAME/KEY: misc_feature
<222> LOCATION: (21)..(21)
<223> OTHER INFORMATION: inverted deoxy abasic

<400> SEQUENCE: 5 cguuggauu gauucgaaau u                                         21

<210> SEQ ID NO 6
<211> LENGTH: 21
<212> TYPE: RNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(4)
<223> OTHER INFORMATION: 2' fluoro
<220> FEATURE:
<221> NAME/KEY: misc_feature
<222> LOCATION: (5)..(6)
<223> OTHER INFORMATION: 2' O-methyl
<220> FEATURE:
<221> NAME/KEY: misc_feature
<222> LOCATION: (7)..(8)
<223> OTHER INFORMATION: 2' fluoro
<220> FEATURE:
<221> NAME/KEY: misc_feature
<222> LOCATION: (9)..(9)
<223> OTHER INFORMATION: ribose
<220> FEATURE:
<221> NAME/KEY: misc_feature
<222> LOCATION: (10)..(10)
<223> OTHER INFORMATION: 2' fluoro
<220> FEATURE:
<221> NAME/KEY: misc_feature
<222> LOCATION: (11)..(11)
<223> OTHER INFORMATION: 2' O-methyl
<220> FEATURE:
<221> NAME/KEY: misc_feature
<222> LOCATION: (12)..(12)
<223> OTHER INFORMATION: ribose
<220> FEATURE:
<221> NAME/KEY: misc_feature
<222> LOCATION: (13)..(13)
<223> OTHER INFORMATION: 2' O-methyl
<220> FEATURE:
<221> NAME/KEY: misc_feature
<222> LOCATION: (14)..(14)
<223> OTHER INFORMATION: 2' fluoro
<220> FEATURE:
<221> NAME/KEY: misc_feature
<222> LOCATION: (15)..(15)
<223> OTHER INFORMATION: ribose
<220> FEATURE:
<221> NAME/KEY: misc_feature
<222> LOCATION: (16)..(16)
<223> OTHER INFORMATION: 2' fluoro
<220> FEATURE:
<221> NAME/KEY: misc_feature
<222> LOCATION: (17)..(17)
<223> OTHER INFORMATION: 2' O-methyl
<220> FEATURE:
<221> NAME/KEY: misc_feature
<222> LOCATION: (18)..(18)
<223> OTHER INFORMATION: 2' fluoro
<220> FEATURE:
<221> NAME/KEY: misc_feature
<222> LOCATION: (19)..(19)
<223> OTHER INFORMATION: ribose
<220> FEATURE:
<221> NAME/KEY: misc_feature
<222> LOCATION: (20)..(21)
<223> OTHER INFORMATION: 2' O-methyl
<220> FEATURE:
<221> NAME/KEY: misc_feature
<222> LOCATION: (20)..(21)
```

<223> OTHER INFORMATION: phophorothioate linkage

<400> SEQUENCE: 6
uuucgaauca auccaacagu u                                                    21

<210> SEQ ID NO 7
<211> LENGTH: 21
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(1)
<223> OTHER INFORMATION: inverted deoxy abasic
<220> FEATURE:
<221> NAME/KEY: misc_feature
<222> LOCATION: (1)..(1)
<223> OTHER INFORMATION: 2' fluoro
<220> FEATURE:
<221> NAME/KEY: misc_feature
<222> LOCATION: (2)..(2)
<223> OTHER INFORMATION: 2' deoxy
<220> FEATURE:
<221> NAME/KEY: misc_feature
<222> LOCATION: (3)..(4)
<223> OTHER INFORMATION: 2' fluoro
<220> FEATURE:
<221> NAME/KEY: misc_feature
<222> LOCATION: (5)..(5)
<223> OTHER INFORMATION: 2' O-methyl
<220> FEATURE:
<221> NAME/KEY: misc_feature
<222> LOCATION: (6)..(7)
<223> OTHER INFORMATION: 2' deoxy
<220> FEATURE:
<221> NAME/KEY: misc_feature
<222> LOCATION: (8)..(9)
<223> OTHER INFORMATION: 2' fluoro
<220> FEATURE:
<221> NAME/KEY: misc_feature
<222> LOCATION: (10)..(10)
<223> OTHER INFORMATION: 2' O-methyl
<220> FEATURE:
<221> NAME/KEY: misc_feature
<222> LOCATION: (11)..(11)
<223> OTHER INFORMATION: ribose
<220> FEATURE:
<221> NAME/KEY: misc_feature
<222> LOCATION: (12)..(14)
<223> OTHER INFORMATION: 2' deoxy
<220> FEATURE:
<221> NAME/KEY: misc_feature
<222> LOCATION: (15)..(15)
<223> OTHER INFORMATION: ribose
<220> FEATURE:
<221> NAME/KEY: misc_feature
<222> LOCATION: (16)..(16)
<223> OTHER INFORMATION: 2' deoxy
<220> FEATURE:
<221> NAME/KEY: misc_feature
<222> LOCATION: (17)..(17)
<223> OTHER INFORMATION: ribose
<220> FEATURE:
<221> NAME/KEY: misc_feature
<222> LOCATION: (18)..(18)
<223> OTHER INFORMATION: 2' O-methyl
<220> FEATURE:
<221> NAME/KEY: misc_feature
<222> LOCATION: (19)..(19)
<223> OTHER INFORMATION: 2' deoxy
<220> FEATURE:
<221> NAME/KEY: misc_feature
<222> LOCATION: (20)..(21)
<223> OTHER INFORMATION: 2' O-methyl
<220> FEATURE:
<221> NAME/KEY: misc_feature

```
<222> LOCATION: (20)..(21)
<223> OTHER INFORMATION: phophorothioate linkage
<220> FEATURE:
<221> NAME/KEY: misc_feature
<222> LOCATION: (21)..(21)
<223> OTHER INFORMATION: inverted deoxy abasic

<400> SEQUENCE: 7
acgacuaguu caguugcuuu u                                              21

<210> SEQ ID NO 8
<211> LENGTH: 21
<212> TYPE: RNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(2)
<223> OTHER INFORMATION: 2' fluoro
<220> FEATURE:
<221> NAME/KEY: misc_feature
<222> LOCATION: (3)..(4)
<223> OTHER INFORMATION: 2' O-methyl
<220> FEATURE:
<221> NAME/KEY: misc_feature
<222> LOCATION: (5)..(5)
<223> OTHER INFORMATION: 2' fluoro
<220> FEATURE:
<221> NAME/KEY: misc_feature
<222> LOCATION: (6)..(6)
<223> OTHER INFORMATION: ribose
<220> FEATURE:
<221> NAME/KEY: misc_feature
<222> LOCATION: (7)..(7)
<223> OTHER INFORMATION: 2' fluoro
<220> FEATURE:
<221> NAME/KEY: misc_feature
<222> LOCATION: (8)..(11)
<223> OTHER INFORMATION: 2' O-methyl
<220> FEATURE:
<221> NAME/KEY: misc_feature
<222> LOCATION: (12)..(14)
<223> OTHER INFORMATION: 2' fluoro
<220> FEATURE:
<221> NAME/KEY: misc_feature
<222> LOCATION: (15)..(15)
<223> OTHER INFORMATION: 2' O-methyl
<220> FEATURE:
<221> NAME/KEY: misc_feature
<222> LOCATION: (16)..(17)
<223> OTHER INFORMATION: ribose
<220> FEATURE:
<221> NAME/KEY: misc_feature
<222> LOCATION: (18)..(21)
<223> OTHER INFORMATION: 2' O-methyl
<220> FEATURE:
<221> NAME/KEY: misc_feature
<222> LOCATION: (20)..(21)
<223> OTHER INFORMATION: phophorothioate linkage

<400> SEQUENCE: 8
aagcaacuga acuagucguu u                                              21

<210> SEQ ID NO 9
<211> LENGTH: 21
<212> TYPE: RNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(1)
<223> OTHER INFORMATION: inverted deoxy abasic
<220> FEATURE:
```

```
<221> NAME/KEY: misc_feature
<222> LOCATION: (1)..(1)
<223> OTHER INFORMATION: 2' fluoro
<220> FEATURE:
<221> NAME/KEY: misc_feature
<222> LOCATION: (2)..(2)
<223> OTHER INFORMATION: 2' deoxy
<220> FEATURE:
<221> NAME/KEY: misc_feature
<222> LOCATION: (3)..(4)
<223> OTHER INFORMATION: 2' fluoro
<220> FEATURE:
<221> NAME/KEY: misc_feature
<222> LOCATION: (6)..(7)
<223> OTHER INFORMATION: 2' deoxy
<220> FEATURE:
<221> NAME/KEY: misc_feature
<222> LOCATION: (8)..(9)
<223> OTHER INFORMATION: 2' fluoro
<220> FEATURE:
<221> NAME/KEY: misc_feature
<222> LOCATION: (10)..(10)
<223> OTHER INFORMATION: 2' O-methyl
<220> FEATURE:
<221> NAME/KEY: misc_feature
<222> LOCATION: (11)..(11)
<223> OTHER INFORMATION: ribose
<220> FEATURE:
<221> NAME/KEY: misc_feature
<222> LOCATION: (12)..(14)
<223> OTHER INFORMATION: 2' deoxy
<220> FEATURE:
<221> NAME/KEY: misc_feature
<222> LOCATION: (15)..(15)
<223> OTHER INFORMATION: ribose
<220> FEATURE:
<221> NAME/KEY: misc_feature
<222> LOCATION: (16)..(16)
<223> OTHER INFORMATION: ribose
<220> FEATURE:
<221> NAME/KEY: misc_feature
<222> LOCATION: (17)..(17)
<223> OTHER INFORMATION: ribose
<220> FEATURE:
<221> NAME/KEY: misc_feature
<222> LOCATION: (18)..(18)
<223> OTHER INFORMATION: 2' O-methyl
<220> FEATURE:
<221> NAME/KEY: misc_feature
<222> LOCATION: (19)..(19)
<223> OTHER INFORMATION: 2' deoxy
<220> FEATURE:
<221> NAME/KEY: misc_feature
<222> LOCATION: (20)..(21)
<223> OTHER INFORMATION: 2' O-methyl
<220> FEATURE:
<221> NAME/KEY: misc_feature
<222> LOCATION: (21)..(21)
<223> OTHER INFORMATION: inverted deoxy abasic

<400> SEQUENCE: 9
acgacuaguu caguugcuuu u                                              21

<210> SEQ ID NO 10
<211> LENGTH: 21
<212> TYPE: RNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(2)
<223> OTHER INFORMATION: 2' fluoro
<220> FEATURE:
<221> NAME/KEY: misc_feature
<222> LOCATION: (3)..(4)
<223> OTHER INFORMATION: 2' O-methyl
```

```
<220> FEATURE:
<221> NAME/KEY: misc_feature
<222> LOCATION: (5)..(5)
<223> OTHER INFORMATION: 2' fluoro
<220> FEATURE:
<221> NAME/KEY: misc_feature
<222> LOCATION: (6)..(6)
<223> OTHER INFORMATION: ribose
<220> FEATURE:
<221> NAME/KEY: misc_feature
<222> LOCATION: (7)..(7)
<223> OTHER INFORMATION: 2' fluoro
<220> FEATURE:
<221> NAME/KEY: misc_feature
<222> LOCATION: (8)..(11)
<223> OTHER INFORMATION: 2' O-methyl
<220> FEATURE:
<221> NAME/KEY: misc_feature
<222> LOCATION: (12)..(14)
<223> OTHER INFORMATION: 2' fluoro
<220> FEATURE:
<221> NAME/KEY: misc_feature
<222> LOCATION: (15)..(15)
<223> OTHER INFORMATION: 2' O-methyl
<220> FEATURE:
<221> NAME/KEY: misc_feature
<222> LOCATION: (16)..(17)
<223> OTHER INFORMATION: ribose
<220> FEATURE:
<221> NAME/KEY: misc_feature
<222> LOCATION: (18)..(21)
<223> OTHER INFORMATION: 2' O-methyl

<400> SEQUENCE: 10
aagcaacuga acuagucguu u                                          21

<210> SEQ ID NO 11
<211> LENGTH: 52
<212> TYPE: DNA
<213> ORGANISM: Artificial Sequence
<220> FEATURE:
<223> OTHER INFORMATION: Synthetic

<400> SEQUENCE: 11
gtcgtatcca gtgcagggtc cgaggtattc gcactggata cgacctttaa ca        52

<210> SEQ ID NO 12
<211> LENGTH: 22
<212> TYPE: DNA
<213> ORGANISM: Artificial Sequence
<220> FEATURE:
<223> OTHER INFORMATION: Synthetic

<400> SEQUENCE: 12
ggcgcgaaat tcaggaatt gt                                          22

<210> SEQ ID NO 13
<211> LENGTH: 21
<212> TYPE: DNA
<213> ORGANISM: Artificial Sequence
<220> FEATURE:
<223> OTHER INFORMATION: Synthetic

<400> SEQUENCE: 13
cactggatac gacctttaac a                                          21

<210> SEQ ID NO 14
<211> LENGTH: 15
<212> TYPE: DNA
<213> ORGANISM: Artificial Sequence
<220> FEATURE:
```

```
<223> OTHER INFORMATION: Synthetic

<400> SEQUENCE: 14
agtgcagggt ccgag                                          15
```